US012059457B2

(12) United States Patent
Grouard-Vogel et al.

(10) Patent No.: US 12,059,457 B2
(45) Date of Patent: Aug. 13, 2024

(54) IMMUNOGENIC PRODUCT COMPRISING IL-4 AND/OR IL-13 FOR TREATING DISORDERS ASSOCIATED WITH ABERRANT IL-4 AND/OR IL 13 EXPRESSION OR ACTIVITY

(71) Applicants: NEOVACS, Paris (FR); INSERM (INSTITUT NATIONAL DE LA SANTÉ ET DE LA RECHERCHE MÉDICALE), Paris (FR); INSTITUT PASTEUR, Paris (FR)

(72) Inventors: Géraldine Grouard-Vogel, Paris (FR); Eva Conde García, Paris (FR); Romain Bertrand, Paris (FR); Noémie Caillot, Paris (FR); Laurent Reber, Antony (FR); Pierre Bruhns, Paris (FR); Vincent Serra, Bondoufle (FR)

(73) Assignees: NEOVACS, Paris (FR); INSERM (INSTITUT NATIONAL DE LA SANTÉ ET DE LA RECHERCHE MÉDICALE), Paris (FR); INSTITUT PASTEUR, Paris (FR)

(*) Notice: Subject to any disclaimer, the term of this patent is extended or adjusted under 35 U.S.C. 154(b) by 0 days.

(21) Appl. No.: 17/058,318

(22) PCT Filed: May 29, 2019

(86) PCT No.: PCT/EP2019/064025
§ 371 (c)(1),
(2) Date: Nov. 24, 2020

(87) PCT Pub. No.: WO2019/229153
PCT Pub. Date: Dec. 5, 2019

(65) Prior Publication Data
US 2021/0205427 A1   Jul. 8, 2021

Related U.S. Application Data

(60) Provisional application No. 62/677,290, filed on May 29, 2018.

(30) Foreign Application Priority Data

May 29, 2018  (EP) ..................... 18305651
Jan. 4, 2019   (WO) ............. PCT/EP2019/050154

(51) Int. Cl.
A61P 17/00    (2006.01)
A61K 39/00    (2006.01)
A61K 47/54    (2017.01)
A61K 47/64    (2017.01)
A61P 11/00    (2006.01)
A61P 37/06    (2006.01)
A61P 37/08    (2006.01)

(52) U.S. Cl.
CPC ........ *A61K 39/0008* (2013.01); *A61K 47/545* (2017.08); *A61K 47/646* (2017.08); *A61P 11/00* (2018.01); *A61P 17/00* (2018.01); *A61P 37/06* (2018.01); *A61P 37/08* (2018.01); *A61K 2039/6037* (2013.01)

(58) Field of Classification Search
None
See application file for complete search history.

(56) References Cited

U.S. PATENT DOCUMENTS

| 4,912,094 A | 3/1990 | Myers et al. |
| 5,057,540 A | 10/1991 | Kensil et al. |
| 6,113,918 A | 9/2000 | Johnson et al. |
| 6,207,646 B1 | 3/2001 | Krieg et al. |
| 2016/0101191 A1 | 4/2016 | Jin |

FOREIGN PATENT DOCUMENTS

| EP | 1947116 A2 | 7/2008 | |
| EP | 1443960 B1 | 12/2008 | |
| WO | 9014837 A1 | 12/1990 | |
| WO | 9219265 A1 | 11/1992 | |
| WO | 9313302 A1 | 7/1993 | |
| WO | 0018434 A1 | 4/2000 | |
| WO | 02098368 A2 | 12/2002 | |
| WO | 02098369 A2 | 12/2002 | |
| WO | 2004019974 A2 | 3/2004 | |
| WO | WO-2004019979 A2 * | 3/2004 | ......... A61K 39/0005 |
| WO | 2009052081 A2 | 4/2009 | |
| WO | 2013179302 A1 | 12/2013 | |

OTHER PUBLICATIONS

Vingtdeaux, V., et al. Mol. Med .; 22:841-849 (Year: 2016).*
Mantile, F., et al. PLOS One;9(7):1-10 (Year: 2014).*
Renshaw, S. (ed.) Immunohistochemistry and Immunocytochemistry (2nd.ed.), Wiley Blackwell (Year: 2017).*
Naina Gour & Marsha Wills-Karp, "IL-4 and IL-13 Signaling in Allergic Airway Disease", HHS Public Access Author Manuscript, Cytokine, Sep. 2015, vol. 75, No. 1, 26 pages, doi: 10.1016/j.cyto.2015.05.014.
John M. Hickey, et al., "Analytical Comparability Assessments of 5 Recombinant CRM 197 Proteins From Different Manufacturers and Expression Systems", Journal of Pharmaceutical Sciences, Jul. 2018, vol. 107, No. 7, pp. 1806-1819 (14 pp.), doi: 10.1016/j.xphs.2018.03.002.
Tsuyoshi Uchida, et al., "Diphteria Toxin and Related Proteins. Isolation and properties of mutant proteins serologically related to diphtheria toxin", Journal of Biological Chemistry, Jun. 10, 1973, vol. 248, No. 11, pp. 3838-3844 (7 pp.).

(Continued)

Primary Examiner — G. R. Ewoldt
(74) Attorney, Agent, or Firm — Maier & Maier, PLLC

(57) ABSTRACT

An immunogenic product including a cytokine conjugated with a carrier protein, wherein the cytokine is selected from the group including IL-4, IL-13 and mixtures thereof, and wherein the carrier protein is $CRM_{197}$. Further, a method for manufacturing the immunogenic product. Also, the therapeutic use of the immunogenic product for treating an inflammatory disorder associated with aberrant IL-4 and/or IL-13 expression or activity.

8 Claims, 10 Drawing Sheets
Specification includes a Sequence Listing.

(56) References Cited

OTHER PUBLICATIONS

Ashwin Swaminathan, et al., "Keyhole limpet haemocyanin—a model antigen for human immunotoxicological studies", British Journal of Clinical Pharmacology, Nov. 2014, vol. 78, No. 5, pp. 1135-1142 (8 pp.), doi: 10.1111/bcp.12422.

Gopalan Soman, et al., "MTS dye based colorimetric CTLL-2 cell proliferation assay for product release and stability monitoring of interleukin-15: Assay qualification, standardization and statistical analysis", HHS Public Access Author Manuscript, Journal of Immunological Methods, Aug. 31, 2009, vol. 348, No. 1-2, 25 pages, doi: 10.1016/j.iim.2009.07.010.

C. H. Meyer, et al., "Comparison of the levels of the major allergens Der p I and Der p II in standardized extracts of the house dust mite, Dermatophagoides pteronyssinus", Clinical & Experimental Allergy, Nov. 1994, vol. 24, No. 11, pp. 1041-1048 (8 pp.), doi: 10.1111/j.1365-2222.1994.tb02741.x.

E. Hamelmann, et al., "Noninvasive Measurement of Airway Responsiveness in Allergic Mice Using Barometric Plethysmography", American Journal of Respiratory and Critical Care Medicine, Sep. 1997, vol. 156, No. 3 Part 1, pp. 766-775 (10 pp.), doi: 10.1164/ajrccm.156.3.9606031.

Oliver T. Burton, et al., "Inhibition of Immunoglobulin E signals during allergen ingestion leads to reversal of established food allergy and induction of regulatory T cells", HHS Public Access Author Manuscript, Immunity, Jul. 17, 2014, vol. 41, No. 1, 27 pages, doi: 10.1016/j.immuni.2014.05.017.

Tomoaki Ando, et al., "Mast cells are required for full expression of allergen/SEB-induced skin inflammation", HHS Public Access Author Manuscript, Journal of Investigative Dermatology, Dec. 2013, vol. 133, No. 12, 20 pages, doi: 10.1038/jid.2013.250.

Sho Shibata, et al., "Basophils trigger emphysema development in a murine model of COPD through IL-4-mediated generation of MMP-12-producing macrophages", Proceedings of the National Academy of Sciences, Dec. 18, 2018, vol. 115, No. 51, pp. 13057-13062 (6 pp.), doi: 10.1073/pnas.1813927115.

Laurent L. Reber, et al., "Mast Cells Contribute to Bleomycin-Induced Lung Inflammation and Injury in Mice through a Chymase/Mast Cell Protease 4-Dependent Mechanism", Journal of Immunology, Feb. 15, 2014, vol. 192, No. 4, pp. 1847-1854 (8 pp.), doi: 10.4049/jimmunol.1300875.

Hélène Le Buanec, et al., "Control of allergic reactions in mice by an active anti-murine IL-4 immunization", Vaccine, Oct. 10, 2007, vol. 25, No. 41, pp. 7206-7216 (11 pp.), doi: 10.1016/j.vaccine.2007.07.029.

D. Zagury, et al., "Active versus passive anti-cytokine antibody therapy against cytokine-associated chronic diseases", Cytokine and Growth Factor Reviews, Apr. 2003, vol. 14, No. 2, pp. 123-137 (15 pp.), doi: 10.1016/s1359-6101(03)00004-2.

Hai-Long Zhang, et al., "A novel combined conjugate vaccine: Enhanced immunogenicity of bFGF with CRM197 as a carrier protein", Molecular Medicine Reports, Sep. 2011, vol. 4, No. 5, pp. 857-863 (7 pp.), doi: 10.3892/mmr.2011.521.

Yanbing Ma, et al., "A potential immunotherapy approach: Mucosal immunization with an IL-13 peptide-based virus-like particle vaccine in a mouse asthma model", Vaccine, Nov. 19, 2007, vol. 25, No. 47, pp. 8091-8099 (9 pp.), doi: 10.1016/j.vaccine.2007.09.009.

Yanbing Ma, et al., "Sustained Suppression of IL-13 by a Vaccine Attenuates Airway Inflammation and Remodeling in Mice", American Journal of Respiratory Cell and Molecular Biology, May 2013, vol. 48, No. 5, pp. 540-549 (10 pp.), doi: 10.1165/rcmb.2012-0060OC.

Diego Bagnasco, et al., "A Critical Evaluation of Anti-IL-13 and Anti-IL-4 Strategies in Severe Asthma", International Archives of Allergy and Immunology, 2016, vol. 170, No. 2, pp. 122-131 (10 pp.), doi: 10.1159/000447692.

Clinical Trial NCT02665364, "Phase IIb Study of IFN-K in Systemic Lupus Erythematosus". Available at https://www.clinicaltrials.gov/ct2/show/study/NCT02665364. First posted Jan. 27, 2016. 9 pages.

Jing et al., "Interleukin-13 peptide kinoid vaccination attenuates allergic inflammation in a mouse model of asthma", International Journal of Molecular Medicine, 2012, vol. 30, No. 3, pp. 553-560.

Francis, "Carriers for Peptides: Theories and Technology", Department of Virology and Process Development, New Generation Vaccines, Springer, Boston, MA, 1993, pp. 33-42.

Tobias et al., "Enhanced and long term immunogenicity of a Her-2/neu multi-epitope vaccine conjugated to the carrier CRM197 in conjunction with the adjuvant Montanide", BMC Cancer, 2017, vol. 17, No. 1, pp. 1-13.

Scaria et al., "Protein-protein conjugate nanoparticles for malaria antigen delivery and enhanced immunogenicity", PLOS ONE, vol. 12, Dec. 27, 2017, Article e0190312, doi: 10.1371/journal.pone.0190312, 19 pages.

\* cited by examiner

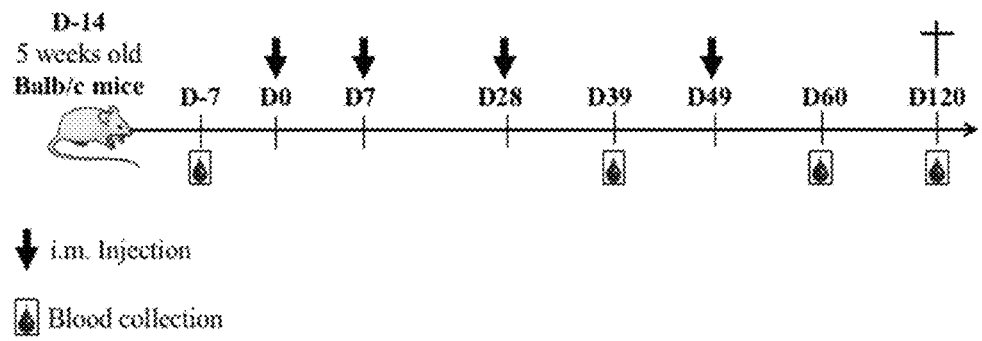
FIG. 3
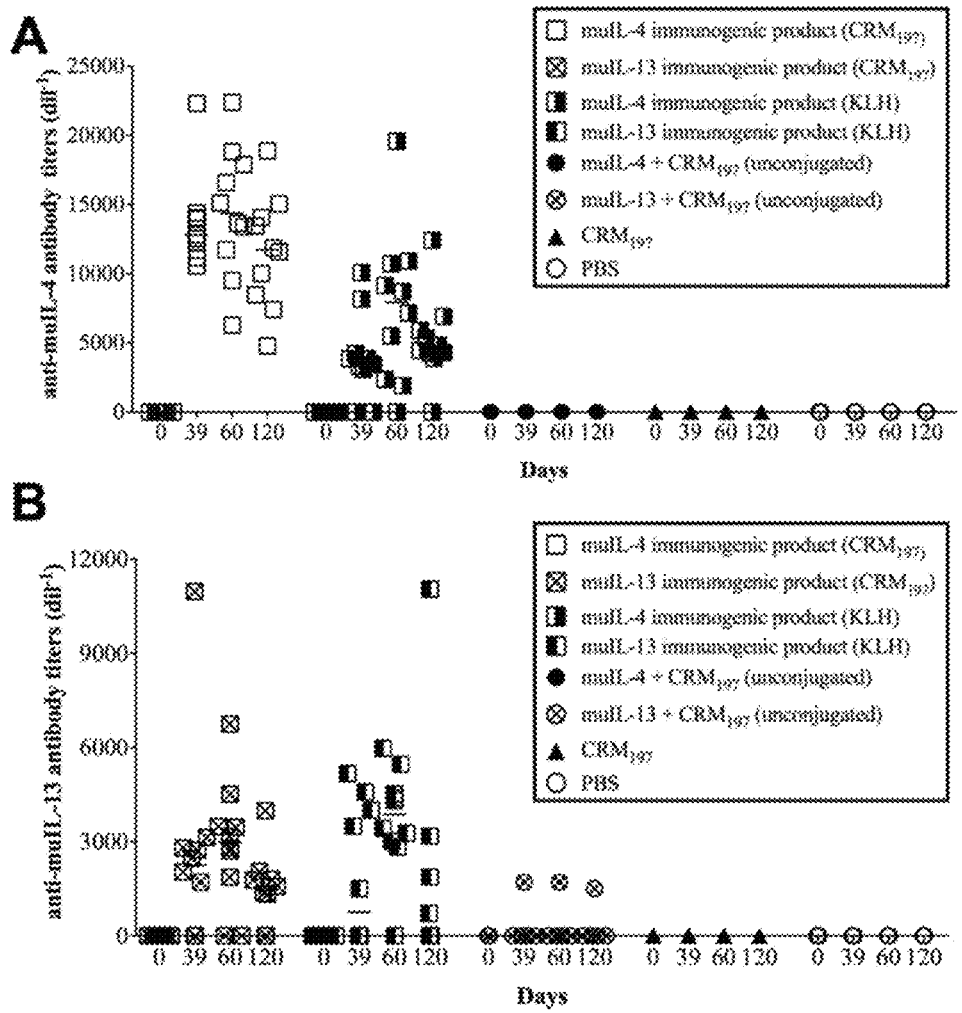
FIG. 4A-B

FIG. 4C-D

IMMUNOGENIC PRODUCT COMPRISING IL-4 AND/OR IL-13 FOR TREATING DISORDERS ASSOCIATED WITH ABERRANT IL-4 AND/OR IL 13 EXPRESSION OR ACTIVITY

FIELD

The present invention relates to an immunogenic product and to the use thereof for treating disorders associated with aberrant IL-4 and/or IL-13 expression or activity, in particular asthma, atopic dermatitis and allergic disorders.

BACKGROUND

Allergic disorders are complex diseases resulting from interactions between multiple genetic and environmental factors. The increase in allergies observed in the past decades is explained mostly by environmental changes occurring in the same period. Among all allergies, allergic asthma, allergic rhinitis and food allergies are major public health problems, now each affecting at least 300 million peoples worldwide. Moreover, it is estimated that half of the global population will be affected by an allergic disease by 2050. In terms of annual mortality, globally, there are almost 300,000 avoidable allergy-related deaths caused by asthma, food allergy, or anaphylaxis. Thus, the increase in allergic diseases has become an important health issue throughout the globe resulting in significant socioeconomic burden and for which there is still no efficient long-term therapy.

Pathogenesis of allergic disorders results from the exposure of the immune system to allergens. Such exposures are considered to be responsible of a breakdown of tolerance, resulting in type 2 immune responses characterized by the production of T helper cell type 2 (Th2) cytokines such as interleukin 4 (IL-4) and interleukin 13 (IL-13), high levels of immunoglobulin E (IgE) antibodies, and infiltration and expansion of immune cells within the inflamed tissue. Mast cells, basophils, and eosinophils are especially involved in the release of cytoplasmic granules containing preformed inflammatory mediators such as histamine. Upon exposure to an allergen, such allergen is recognized by IgE and bound to receptors on mast cell basophil and eosinophil surfaces, which promotes the degranulation of these cells and therefore the appearance of clinical symptoms. Of note, for these reasons, clinical diagnoses of allergies are largely based on measurements of allergen-specific IgE.

Interestingly, IL-4 and IL-13 cytokines play key roles in the pathogenesis of allergic disorders. Both cytokines have long been associated with the pathogenesis of allergic disorders and are therapeutically important cytokines based on their biological functions. These two cytokines present similar structure, and share one receptor subunit (IL-4Rα). However, despite their many similarities, IL-4 and IL-13 are also thought to play some non-redundant functions in allergy.

IL-4 is a pleiotropic cytokine that is involved in the development of allergy (Gour N. & Wills-Karp M., 2015), as increased IL-4 levels have been observed in serum and in bronchoalveolar lavage of asthmatic patients. IL-4 is considered to specifically act in the early phase of allergy development. The crucial role of IL-4 lies in its multiple effects which drive to allergy such as induction of IgE production, up-regulation of IgE receptor expression and differentiation of naïve T helper cell type 0 (Th0) into Th2 lymphocytes.

Type 2 immune cells play a pivotal role in allergy process by controlling humoral immunity and B cell switch in antibody response to IgE class. Thus, Th2 cells are mediators of Ig production (e.g., IgE, IgG) and produce various cytokine as well as IL-4 and IL-13.

In contrast, IL-13 is more involved in effector and late phases of allergic reactions (Gour N. & Wills-Karp M., 2015). It has been shown that IL-13 is sufficient to induce the main manifestations of allergic diseases including, without limitation, airways hyperresponsiveness, mucus production, airway smooth muscle alterations and sub-epithelial fibrosis.

Given the range of cells involved in asthma on which IL-4 and IL-13 are known to act, and the pathogenic functions associated with these interleukins, neutralization of one or both cytokines is a credible approach to the treatment of allergic inflammatory disorders. Therefore, as IL-4 and IL-13 are promising therapeutic targets for the treatment of allergies, there is a clear need to improve current strategies to block these molecules, in order to reach long-term therapeutic effects.

Recently, novel therapies have been developed to treat allergies. These treatments, based on passive immunization, specifically target pathogenic factors involved in allergy. For example, the use of recombinant antibodies directed to IL-4 and IL-13 or their receptors was described in the art. However, use of recombinant antibodies is limited by high cost, the need to perform repeated injections, and potential risks of appearance of anti-drug antibodies (ADAs) or other adverse reactions.

The Applicant herein provide a novel immunogenic product, based on the combination of a cytokine selected from IL-4 and IL-13 with $CRM_{197}$. This novel immunogenic product is of particular interest for treating inflammatory disorders, such as, in particular asthma, atopic dermatitis and allergic disorders.

SUMMARY

The present invention relates to an immunogenic product comprising at least one cytokine conjugated with a carrier protein, wherein the at least one cytokine is selected from the group comprising IL-4, IL-13 and mixtures thereof, and wherein the carrier protein is $CRM_{197}$.

In one embodiment, the at least one cytokine is IL-4.

In one embodiment, wherein the at least one cytokine is IL-13.

In one embodiment, the immunogenic product of the invention comprises $CRM_{197}$ coupled with both IL-4 and IL-13.

The present invention further relates to a composition comprising at least one immunogenic product as described hereinabove.

In one embodiment, the composition comprises a mixture of at least two immunogenic products as described hereinabove.

In one embodiment, the composition comprises a mixture of an immunogenic product comprising IL-4 and $CRM_{197}$ with an immunogenic product comprising IL-13 and $CRM_{197}$.

In one embodiment, the composition comprises a mixture of an immunogenic product comprising IL-4 and $CRM_{197}$ with an immunogenic product comprising IL-13 and $CRM_{197}$ at a weight ratio ranging from about 10:1 to about 1:10.

In one embodiment, the composition further comprises at least one pharmaceutically acceptable excipient and/or at least one adjuvant.

In one embodiment, the composition is an emulsion.

The present invention further relates to a method for producing an immunogenic product as described herein, the method comprising steps of:
- a) contacting the at least one cytokine with a heterobifunctional crosslinker containing a NHS-ester, preferably N-[γ-maleimidobutyryloxy]-succinimide ester (sGMBS);
- b) contacting the carrier protein with a heterobifunctional crosslinker containing a NHS-ester, preferably N-succinimidyl-S-acetylthioacetate (SATA) to generate a carrier-SATA complex;
- c) contacting the sGMBS-cytokine complex obtained at step (a) with the carrier SATA complex obtained at step (b).

The present invention further relates to an immunogenic product as described herein or a composition as described herein, for treating an inflammatory disorder.

In one embodiment, the inflammatory disorder is a disorder associated with aberrant IL-4 and/or IL-13 expression or activity.

In one embodiment, the inflammatory disorder is selected from the group comprising asthma (either allergic or non-allergic), allergic conditions (such as, for example, food allergies, venom allergy, allergy to animals, drug allergy, hyper IgE syndrome, allergic rhinitis, allergic conjunctivitis and allergic enterogastritis), atopic disorders (such as, for example, atopic dermatitis, urticaria (including chronic idiopathic urticaria and chronic spontaneous urticaria), eczema), bullous pemphigoid, respiratory disorders (such as allergic and nonallergic asthma, chronic obstructive pulmonary disease (COPD)), nasal polyposis and other conditions involving airway inflammation (such as, for example, eosinophilia, fibrosis and excess mucus production including cystic fibrosis and pulmonary fibrosis, systemic sclerosis (SSc)); inflammatory and/or autoimmune disorders or conditions, gastrointestinal disorders or conditions (such as, for example, inflammatory bowel diseases (IBD) and eosinophilic esophagitis (EE), and eosinophilic-mediated gastrointestinal disease, ulcerative colitis and Crohn's disease); systemic lupus erythematosus, liver disorders or conditions (such as, for example, cirrhosis, and hepatocellular carcinoma), scleroderma; fibrotic diseases or disorders (such as, for example, fibrosis of the liver (such as, for example, fibrosis caused by a hepatitis B and/or C virus)), scleroderma; solid tumors or cancers such as leukemia (such as, for example, B cell chronic lymphocytic leukaemia), glioblastoma, lymphoma (such as, for example, Hodgkin's lymphoma) and mastocytosis.

In one embodiment, the inflammatory disorder is selected from the group comprising asthma (e.g., allergic asthma), atopic dermatitis, chronic obstructive pulmonary disease (COPD), pulmonary fibrosis, food allergy, nasal polyposis and eosinophilic esophagitis.

In one embodiment, the inflammatory disorder is selected from the group comprising asthma (e.g., allergic asthma), atopic dermatitis, chronic obstructive pulmonary disease (COPD), pulmonary fibrosis and food allergy.

In one embodiment, the inflammatory disorder is allergy, asthma, or atopic dermatitis.

In one embodiment, the immunogenic product or composition as described herein induces desensitization of an allergic subject toward an allergen.

The present invention further relates to an immunogenic product or to a composition as described herein, for inducing desensitization of a subject allergic to a specific antigen, wherein said immunogenic product or composition and said specific antigen are to be administered to the allergic subject.

The present invention further relates to a method for inducing desensitization of a subject allergic to a specific antigen, wherein said method comprises administering to the subject an immunogenic product or composition as described herein and said specific antigen.

The present invention also further relates to a method for increasing the efficacy and/or for decreasing the duration of a desensitization of a subject allergic to a specific allergen, wherein said subject is administered with an immunogenic product or composition as described herein and is further treated by desensitization.

BRIEF DESCRIPTION OF THE DRAWINGS

FIG. 3 is a study scheme of immunizations in Balb/c mice. Four immunizations at days 0, 7, 28 and 49 of immunogenic product (with $CRM_{197}$ or KLH as carrier protein), unconjugated muIL-4 or muIL-13+$CRM_{197}$ and $CRM_{197}$ alone and PBS, all emulsified in squalene adjuvant and i.m. injected in 10 mice per group except for control group only 5 mice. Blood samples were performed before dosing and at day 39 and day 120.

Figure 12:
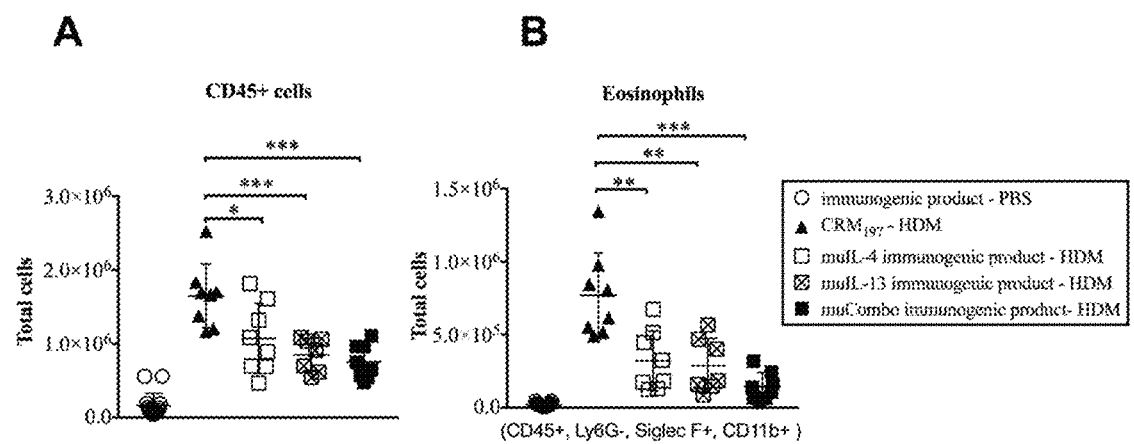

FIG. 12 is a combination of graphs showing the levels of CD45+ cells (A) and eosinophils (B) in BAL collected 24 h after the last challenge with HDM. Data were obtained using 7-8 mice per group for HDM sensitized/challenged mice and n=16 for PBS controls. * or  or *: P<0.5 or 0.1 or 0.001 vs. $CRM_{197}$-HDM group, using unpaired Mann-Whitney U test.

Figure 13:
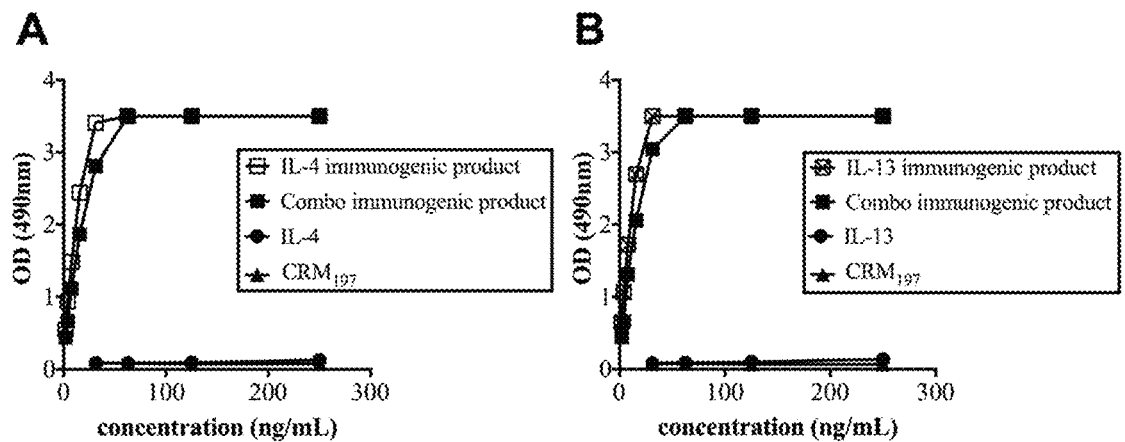

FIG. 13 is a combination of graphs showing the antigenicity of IL-4 immunogenic product (A), IL-13 immunogenic product (B) and Combo immunogenic product (A and B). Capture was performed with anti-$CRM_{197}$ antibody and detection with biotinylated polyclonal anti-huIL-4 antibody (A) or biotinylated polyclonal anti-huIL-13 antibody (B). Represented OD values are OD means of duplicates.

Figure 14:
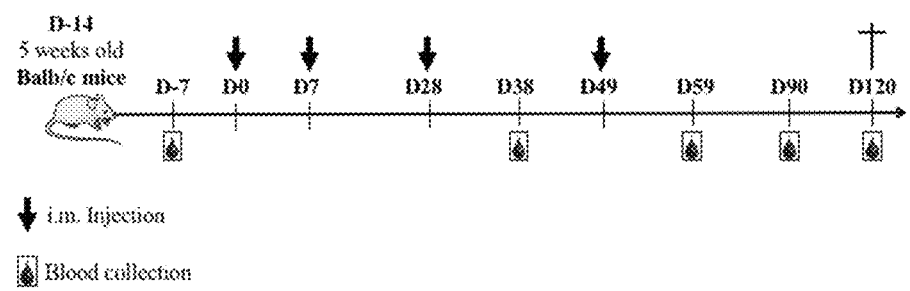

FIG. 14 is a study scheme of immunization in Balb/c mice.

Figure 15:
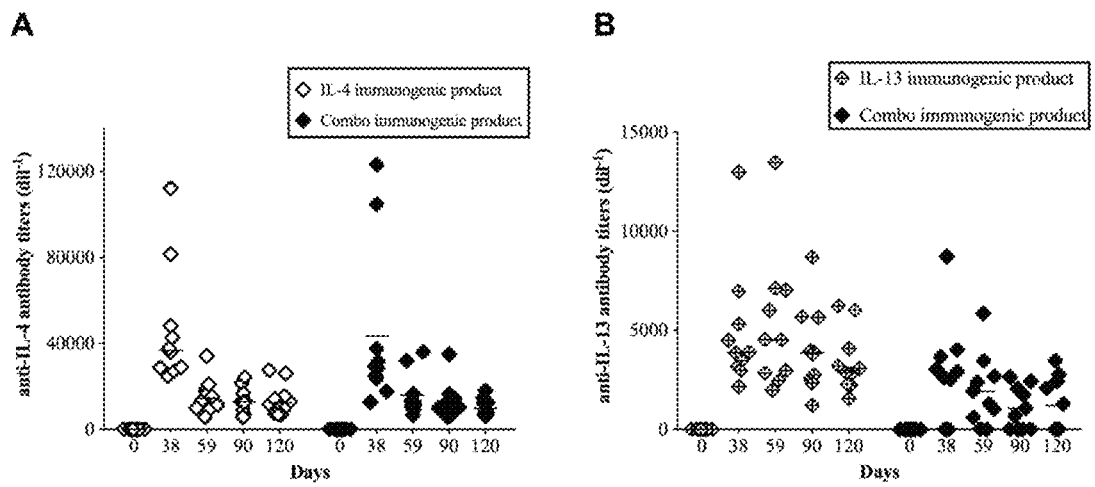

FIG. 15 is a combination of graphs showing the anti-IL-4 (A) and anti-IL-13 (B) antibody titers in mice sera. Ten mice per group. Bars represent median.

Figure 16:
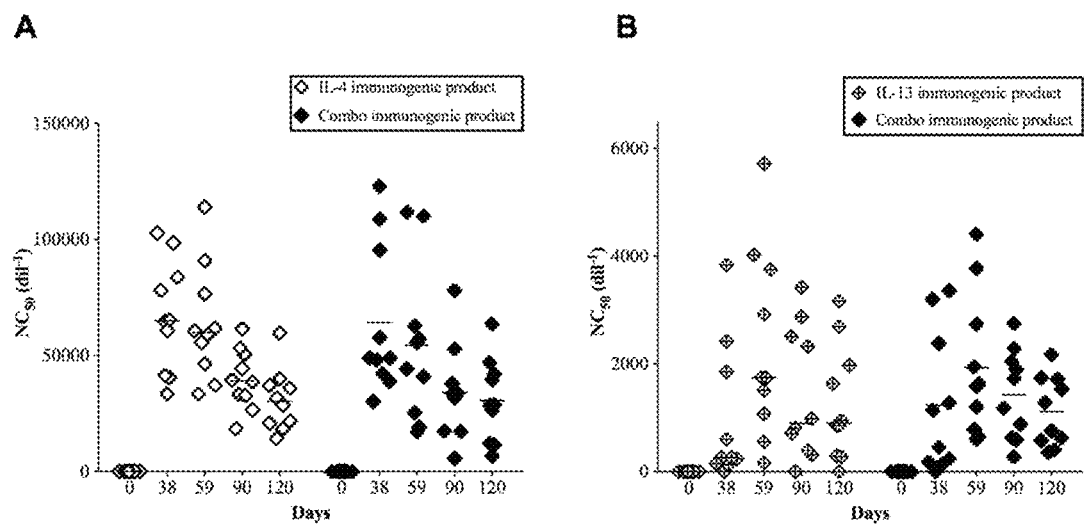

FIG. 16 is a combination of graphs showing the anti-IL-4 (A) and anti-IL-13 (B) neutralizing capacities in mice sera. Ten mice per group. Bars represent median.

DEFINITIONS DETAILED DESCRIPTION

In the present invention, the following terms have the following meanings:

As used herein, the term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

As used herein, an "adjuvant" is a substance that enhances the immunogenicity of an immunogenic product of this invention. Adjuvants are often given to boost the immune response and are well known to the skilled artisan.

As used herein, the term "carrier protein molecule" refers to a protein or a peptide of at least 15, 30 or 50 amino acids long which, when it is partially covalently associated to at least one cytokine selected from IL-4; IL-13 and mixtures thereof for forming heterocomplexes, allows for a large number of antigens of said at least one cytokine to be presented to the B lymphocytes.

As used herein, the term "immune response" refers to the action, for example of lymphocytes, antigen presenting cells, phagocytic cells and macromolecules produced by the above cells or the liver (including antibodies, cytokines and complement).

As used herein, the term "immunogenic product" refers to at least one cytokine coupled to a carrier protein that induces an immune response in a subject, preferably a mammal, to whom said immunogenic product is administered, including a humoral immune response, i.e., the production of antibodies that neutralize the properties, such as, for example, the biological activity of the endogenous cytokine.

As used herein, an antibody that "inhibits the biological activity" or "neutralizes the biological activity" of at least one cytokine selected from IL-4, IL-13 or mixtures thereof is intended to refer to an antibody that inhibits the activity of that cytokine by at least 10%, 20%, 30%, 40%, 50%, 60%, 70%, or 80% or more, as compared to the level of activity of the cytokine in the absence of the antibody, for example by using a functional assay such as those described in the Examples.

As used herein, the term "pharmaceutically acceptable excipient" refers to an excipient that does not produce an adverse, allergic or other untoward reaction when administered to a mammal, preferably a human. It includes any and all solvents, dispersion media, coatings, antibacterial and antifungal agents, isotonic and absorption delaying agents and the like. A pharmaceutically acceptable carrier or excipient refers to a non-toxic solid, semi-solid or liquid filler, diluent, encapsulating material or formulation auxiliary of any type. For human administration, preparations should meet sterility, pyrogenicity, general safety and purity standards as required by the regulatory offices such as the FDA or EMA.

As used herein, the term "recombinant protein" refers to a protein (e.g., a cytokine or a carrier protein $CRM_{197}$) which is generated using recombinant DNA technology, such as, for example, a protein (e.g., a cytokine or a carrier protein $CRM_{197}$) expressed in prokaryote cells (using a bacteriophage or a plasmid expression system) or in eukaryotic cells (such as for example yeast, insect or mammalian expression system). This term should also be construed to mean a protein (e.g., a cytokine or a carrier protein $CRM_{197}$) which has been generated by the synthesis of a DNA molecule encoding the protein (e.g., the cytokine or a carrier protein $CRM_{197}$) and which DNA molecule expresses a protein (e.g., a cytokine or a carrier protein $CRM_{197}$), or an amino acid sequence specifying the protein (e.g., the cytokine or a carrier protein $CRM_{197}$), wherein the DNA or amino acid sequence has been obtained using recombinant DNA or amino acid sequence technology which is available and well known in the art.

As used herein, the term "subject" is intended to include living organisms in which an immune response can be elicited (e.g., mammals, in particular human, primates, dogs, cats, horses, sheep and the like). Preferably, the subject is a human. In one embodiment, a subject may be a "patient", i.e. a warm-blooded animal, preferably a human, who/which is awaiting the receipt of, or is receiving medical care or was/is/will be the object of a medical procedure or is monitored for the development of the targeted disease or condition, such as, for example, an inflammatory disorder. In one embodiment, the subject is an adult (for example a subject above the age of 18). In another embodiment, the subject is a child (for example a subject below the age of 18). In one embodiment, the subject is a male. In another embodiment, the subject is a female. In one embodiment, the subject is affected, preferably is diagnosed, with an inflammatory disorder. In one embodiment, the subject is at risk of developing an inflammatory disorder. Examples of risks factor include, but are not limited to, genetic predisposition, or familial history of inflammatory disorders.

As used herein, the terms "therapeutically effective amount" refer to an amount of the immunogenic product as described herein, effective to achieve a particular biological result. Thus, the terms "therapeutically effective amount" mean a level or amount of immunogenic product that is aimed at, without causing significant negative or adverse side effects to the target, (1) delaying or preventing the onset of the targeted disease or condition; (2) slowing down or stopping the progression, aggravation, or deterioration of one or more symptoms of the targeted disease or condition; (3) bringing about ameliorations of the symptoms of the targeted disease or condition; (4) reducing the severity or incidence of the targeted disease or condition; or (5) curing the targeted disease or condition. A therapeutically effective amount may be administered prior to the onset of the targeted disease or condition, for a prophylactic or preventive action. Alternatively, or additionally, the therapeutically effective amount may be administered after initiation of the targeted disease or condition, for a therapeutic action.

As used herein, the term "treatment" or "treating" refers to both therapeutic treatment and prophylactic or preventative measures; wherein the object is to prevent or slow down (lessen) the targeted disease or condition. Those in need of treatment include those already with the condition as well as those prone to have the condition or those in whom the condition is to be prevented. A subject is successfully "treated" for a disease or condition if, after receiving a therapeutic amount of an immunogenic product as described herein, the subject shows observable and/or measurable improvement in one or more of the following: reduction in the number of pathogenic cells; reduction in the percent of total cells that are pathogenic; relief to some extent of one or more of the symptoms associated with the specific condition; reduced morbidity and mortality, and/or improvement in quality of life issues. The above parameters for assessing successful treatment and improvement in the condition are readily measurable by routine procedures familiar to a physician.

The present invention relates to an immunogenic product comprising at least one cytokine conjugated with a carrier protein, wherein the at least one cytokine is selected from the group comprising IL-4, IL-13 and mixtures thereof, and wherein the carrier protein is $CRM_{197}$.

The Inventors herein demonstrated that an immunogenic product of the invention presents advantages as compared to the same immunogenic product comprising KLH instead of $CRM_{197}$, in particular in terms of immunogenicity.

$CRM_{197}$ is a non-toxic mutant of diphtheria toxin having the sequence SEQ ID NO: 1, without toxic activity due to a single base substitution (mutation from glycine to glutamate in position 52).

SEQ ID NO: 1
GADDVVDSSKSFVMENFSSYHGTKPGYVDSIQKG-IQKPKSGTQGNYDDDWKEFYST DNKYDAAGYSVD-NENPLSGKAGGVVKVTYPGLTKVLALKVDNAETIK-KELGLSLTE PLMEQVGTEEFIKRFGDGASRVVLSLP-FAEGSSSVEYINNWEQAKALSVELEINFETR GKRG-QDAMYEYMAQACAGNRVRRSVGSSLSCINLDWD-VIRDKTKTKIESLKEHGPI KNKMSESPNKTVSEEK-AKQYLEEFHQTALEHPELSELKTVTGTNPVFAGAN-YAAWA VNVAQVIDSETADNLEKTTAALSILPGIGSV-MGIADGAVHHNTEEIVAQSIALSSLMV AQAIPLVG-ELVDIGFAAYNFVESIINLFQVVHNSYNRPAYSPGHK-TQPFLHDGYAVS WNTVEDSIIRTGFQGESGHDIKI-TAENTPLPIAGVLLPTIPGKLDVNKSKTHISVNGRKI RMRCRAIDGDVTFCRPKSPVYVGNGVHANLHVA-FHRSSSEKIHSNEISSDSIGVLGYQKTVDHTKVNSK-LSLFFEIKS

In one embodiment, $CRM_{197}$ may be obtained by conventional methods known in the art in autologous (C. diphtheriae) or heterologous systems (E. coli and P. fluorescens) as described by Hickey in 2018 (Hickey et al. 2018). For example, recombinant $CRM_{197}$ may be obtained by culturing cells containing an expression vector comprising the gene of $CRM_{197}$, harvesting inclusion bodies and purifying $CRM_{197}$. $CRM_{197}$ could also be extracted from culture of Corynebacterium diphtheriae from bacteria strain purchased at ATCC (ATCC39255). In one embodiment, $CRM_{197}$ is commercially available, and may be purchased, for example, from Reagent Proteins (San Diego, CA, US).

In one embodiment, the immunogenic product of the invention comprises a variant of $CRM_{197}$, wherein said variant presents at least about 70%, 75, 80, 85, 90, 95% or more identity with SEQ ID NO: 1. In one embodiment, said variant of $CRM_{197}$ comprises the mutation from glycine to glutamate in position 52 and is thus non-toxic.

The term "identity" or "identical", when used in a relationship between the sequences of two or more nucleic acid sequences or of two or more polypeptides, refers to the degree of sequence relatedness between nucleic acid sequences or polypeptides, as determined by the number of matches between strings of two or more nucleic or amino acid residues, respectively. "Identity" measures the percent of identical matches between the smaller of two or more sequences with gap alignments (if any) addressed by a particular mathematical model or computer program (i.e., "algorithms"). Identity of related nucleic acid sequences or polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include ClustalO (Sievers F., et al 2011), the GCG program package, including, GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

In one embodiment, $CRM_{197}$ is full-length $CRM_{197}$.

In one embodiment, the immunogenic product of the invention comprises a fragment of $CRM_{197}$, such as, for example, a fragment comprising at least about 50, 100, 150, 200, 250, 300, 350, 400, 450, or 500 amino acids (preferably contiguous amino acids) from SEQ ID NO: 1.

In one embodiment, the at least one cytokine is IL-4.

In one embodiment, IL-4 is recombinant. Recombinant IL-4 may be obtained by conventional methods known in the art using the nucleic sequence encoding IL-4. For example, recombinant IL-4 may be obtained by culturing cells containing an expression vector comprising the gene of IL-4, harvesting inclusion bodies and purifying the IL-4 cytokine. Recombinant IL-4 is commercially available and may be purchased, for example, from PeproTech (Rocky Hill, NJ, US).

In one embodiment of the present invention, IL-4 is derived from a mammal.

In one embodiment, IL-4 is a variant of a mammal IL-4, wherein said variant presents at least about 70%, 75, 80, 85, 90, 95% or more identity with the mammal IL-4 from which it derives.

In one embodiment, IL-4 is full-length IL-4.

In another embodiment, the at least one cytokine is a fragment of IL-4, such as, for example, a fragment of IL-4 comprising at least about 50, 55, 60, 65, 70, 75, 80, 85, 90, 95, 100, 105, 110, 115, 120 or 125 amino acids (preferably contiguous amino acids) of the IL-4 from which it derives.

In one embodiment, said fragment comprises at least one specific epitope of IL-4.

In one embodiment of the present invention, IL-4 is human IL-4, preferably recombinant human IL-4. Human IL-4 has a sequence SEQ ID NO: 2 (UniProt ID: P05112-1).

SEQ ID NO: 2
HKCDITLQEIIKTLNSLTEQKTLCTELTVTDIFAA-SKNTTEKETFCRAATVLRQFYSHH EKDTRCLGATA-QQFHRHKQLIRFLKRLDRNLWGLAGLNSCPVKEA-NQSTLENFLER LKTIMREKYSKCSS

In one embodiment, IL-4 is a variant of SEQ ID NO: 2, wherein said variant presents at least about 70%, 75, 80, 85, 90, 95% or more identity with SEQ ID NO: 2.

In one embodiment, IL-4 is full-length human IL-4.

In another embodiment, the at least one cytokine is a fragment of human IL-4, such as, for example, a fragment of human IL-4 comprising at least about 50, 55, 60, 65, 70, 75, 80, 85, 90, 95, 100, 105, 110, 115, 120 or 125 amino acids (preferably contiguous amino acids) of SEQ ID NO: 2.

In one embodiment, said fragment comprises at least one specific epitope of human IL-4.

In one embodiment, said fragment comprises or consists in the following sequence: AQQFHRHKQLIRFLKRL-DRNLW (SEQ ID NO: 3).

In one embodiment of the present invention, IL-4 is murine IL-4, preferably recombinant murine IL-4. Murine IL-4 has a sequence SEQ ID NO: 4 (UniProt ID: P07750-1).

SEQ ID NO: 4
HIHGCDKNHLREIIGILNEVTGEGTPCTEMDVPN-VLTATKNTTESELVCRASKVLRIF YLKHGKTPCLKK-NSSVLMELQRLFRAFRCLDSSISCTMNESKSTSLKD-FLESLKSIMQ MDYS

In one embodiment, IL-4 is a variant of SEQ ID NO: 4, wherein said variant presents at least about 70%, 75, 80, 85, 90, 95% or more identity with SEQ ID NO: 4.

In one embodiment, IL-4 is full-length murine IL-4.

In another embodiment, the at least one cytokine is a fragment of murine IL-4, such as, for example, a fragment of murine IL-4 comprising at least about 50, 55, 60, 65, 70, 75, 80, 85, 90, 95, 100, 105, 110, or 115 amino acids (preferably contiguous amino acids) of SEQ ID NO: 4.

In one embodiment, said fragment comprises at least one specific epitope of murine IL-4.

In one embodiment of the present invention, IL-4 is canine IL-4, preferably recombinant canine IL-4. Canine IL-4 has a sequence SEQ ID NO: 5 (UniProt ID: O77762-1).

SEQ ID NO: 5
HNFNITIKEIIKMLNILTARNDSCMELTVKDVFTA-PKNTSDKEIFCRAATVLRQIYTHNCSNRYLRGLYR-NLSSMANKTCSMNEIKKSTLKDFLERLKVI-MQKKYYRH

In one embodiment, IL-4 is a variant of SEQ ID NO: 5, wherein said variant present at least about 70%, 75, 80, 85, 90, 95% or more identity with SEQ ID NO: 5.

In one embodiment, IL-4 is full-length canine IL-4.

In another embodiment, the at least one cytokine is a fragment of canine IL-4, such as, for example, a fragment of canine IL-4 comprising at least about 50, 55, 60, 65, 70, 75, 80, 85, 90, 95, 100, or 105 amino acids (preferably contiguous amino acids) of SEQ ID NO: 5.

In one embodiment, said fragment comprises at least one specific epitope of canine IL-4.

In one embodiment, the immunogenic product of the invention comprises IL-4 coupled to $CRM_{197}$ at a molar ratio IL-4:$CRM_{197}$ ranging from about 16:1 to about 1:2, preferably from about 8:1 to about 2:1, more preferably of about 4:1.

In one embodiment, the immunogenic product of the invention comprises IL-4 coupled to $CRM_{197}$ and is recognized by anti-IL-4 antibodies.

The fact that the immunogenic product comprises IL-4 coupled to $CRM_{197}$ and is recognized by anti-IL-4 antibodies may be verified by conventional methods known in the art. An example of such methods is a sandwich ELISA anti-cytokine/carrier protein, using for example a detection antibody labelled with biotin, streptavidin HRP amplification system and an o-phenylenediamine dihydrochloride (OPD) substrate solution.

In one embodiment, the TEST $A^{IL-4}$ described herein may be used for verifying that the immunogenic product of the invention comprises IL-4 coupled to $CRM_{197}$ and is recognized by anti-IL-4 antibodies. TEST $A^{IL-4}$ is an ELISA test anti-IL-4/$CRM_{197}$.

TEST $A^{IL-4}$ is carried out as follows:

- Coating a plate with a capture antibody directed to $CRM_{197}$, such as, for example anti-*diphtheriae* toxin antibodies from Abcam (AB53828) or Bio-Rad (3710-0956, 3710-0150 or 3710-0100),
- Blocking the plate with a blocking buffer (such as, for example, casein 2% (w/v) in PBS for example) during about 90 min at about 37° C.,
- Incubating during about 90 min at about 37° ° C. the plate with a two-fold-serial dilution of the immunogenic product starting at 250 ng/mL or with negative controls such as, for example, IL-4 and $CRM_{197}$,
- Incubating during about 90 min at about 37° ° C. the plate with a biotinylated detection antibody directed to IL-4, such as, for example anti-IL-4 biotinylated antibodies from Abcam (AB84278), R&D systems (BAF204) or PeproTech (500-P24BT) or murine anti-IL-4 biotinylated antibodies from Southern Biotech (10204-08), R&D systems (BAF404) or PeproTech (500-P54BT),
- Incubating the plate with streptavidin-HRP during about 30 min at about 37° C. and developing the complex with an OPD substrate solution during about 30 min,
- After stopping the enzymatic reaction, the intensity of the resulting color is determined by spectrophotometric methods at 490 nm.

In one embodiment, when the optical density of wells containing the immunogenic product of the invention at about 25 ng per well is at least about 3-fold, preferably at least about 5-fold, and more preferably at least about 10-fold the optical density of wells containing a negative control, the person skilled in the art may conclude that the immunogenic product of the invention (i) is recognized by anti-IL-4 antibodies and (ii) comprises IL-4 coupled to $CRM_{197}$.

In one embodiment, the immunogenic product of the invention comprises IL-4 coupled to $CRM_{197}$, and is strongly inactivated, which means that the immunogenic product shows less than about 10% of IL-4 initial activity, preferably less than about 5% and preferably less than about 1% of IL-4 initial activity in the condition of hereunder cited TEST $B^{IL-4}$. TEST $B^{IL-4}$ is a colorimetric T cell proliferation assay or a reporter gene bioassay, using a cell line expressing an IL-4Rα that may be functionally activated by the IL-4 comprised in the immunogenic product of the invention (i.e., which may bind the IL-4 comprised in the immunogenic product of the invention, and be activated following this binding).

In one embodiment, the immunogenic product of the invention comprises murine IL-4, and TEST $B^{IL-4}$ is a colorimetric T cell proliferation assay carried out using CTLL-2 cells (from ECACC cell lines, provided by Sigma-Aldrich, reference 93042610-1VL) in the following method:

- CTLL-2 cells are grown in presence of IL-2 at 10 ng/mL final with RPMI supplemented with 2 mM glutamine, 1 mM sodium pyruvate, 1 mM HEPES, 100 U/mL penicillin, 100 μg/mL streptomycin (completed RMPI or RPMIc), and 10% (v/v) FBS,
- The immunogenic product of the invention (IL-4/$CRM_{197}$) and muIL-4 control are two-fold serially diluted in RPMIc+10% (v/v) FBS in 96-well plates beginning at 1000 ng/ml until 4 ng/mL final for the immunogenic product and 10 ng/mL until 0.04 ng/ml final for muIL-4,
- As a positive control, six wells with muIL-4 at 10 ng/mL were added and used as the maximum cell proliferation control,
- These samples are added to 20,000 CTLL-2 cells per well and plates are incubated for about 48 h at about 37° C., 5% $CO_2$ in a humidified incubator,
- At the end of the culture, cell viability is assessed using methods well-known in the art. One example of such methods is the following: 40 μL/well of a solution of MTS/PMS (Promega, Madison, Wi, US) (wherein MTS stands form 3-(4,5-dimethylthiazol-2-yl)-5-(3-carboxymethoxyphenyl)-2-(4-sulfophenyl)-2H-tetrazolium, inner salt; and PMS stands for phenazine methosulfate) are added to the wells and the plate is incubated for another 4 h at 37° C. 5% $CO_2$, according to the manufacturer instruction. The plate is then read at 490 nm on a spectrophotometer.

In another embodiment, the immunogenic product of the invention comprises human IL-4, and TEST $B^{IL-4}$ is a reporter gene assay carried out using a HEK-Blue™ IL-4/IL-13 cell line purchased from InvivoGen (San Diego, CA, US). In these cells, stimulation with IL-4 or IL-13 activates the JAK/STAT6 pathway with the subsequent production of SEAP. IL-4 biological activity comprised in the immunogenic product of the invention can then be evaluated by assessing SEAP levels in the supernatant.

According to this embodiment, TEST $B^{IL-4}$ comprises the following steps:

- HEK-Blue™ IL-4/IL-13 cells are cultured in an assay medium composed of DMEM GlutaMAX™ supplemented with 10% (v/v) FBS, 10 mM HEPES, 50 U/mL penicillin and 50 μg/mL streptomycin,
- Immunogenic product (IL-4/$CRM_{197}$) and IL-4 control are two-fold serially diluted in assay medium at 8000 and 1 ng/mL final, respectively.
- These dilution samples are then transferred to pre-seeded plates containing 40,000 cells per well HEK-Blue™ IL-4/IL-13 cells. Plates are incubated for about 24 h about 37° C., in a 5% $CO_2$ humidified incubator.
- At the end of the culture, activation pathway is assessed using methods well-known in the art. One example of such methods is the following: 90 μL/well of QUANTI-Blue™ solution (purchased from InvivoGen) are added to 10 L/well of cell supernatant. Then, the plate is incubated for about 1 h at about 37°C, in a 5% $CO_2$ humidified incubator. The plate is then read at 625 nm on a spectrophotometer.

The effective dose 50 ($ED_{50}$) value corresponds to the amount of immunogenic product or cytokine resulting in 50% of maximum cell signal. This value is determined by interpolating the 50% of maximum cell signal onto the abscissa axis using the y=ax+b formula from the curve passing by the dilution points surrounding the 50% inflexion point.

In TEST $B^{IL-4}$, the inactivation factor is calculated by dividing the $ED_{50}$ of the tested immunogenic product by the mean $ED_{50}$ of the IL-4 control standard curves. A result with an inactivation factor >100 means that for the same amount of protein, the IL-4 activity in the immunogenic product corresponds to less than 1% of native IL-4 activity. In one embodiment, an inactivation factor superior to about 2, 2.5, 3.33, 5 or 10, preferably to about 20, more preferably to about 100, indicates that the immunogenic product is strongly inactivated. In one embodiment, a residual activity inferior to about 50%, 40%, 30%, 20% or 10%, preferably inferior to about 5%, and more preferably inferior to about 1% of native IL-4 activity indicates that the immunogenic product is strongly inactivated.

In one embodiment, the immunogenic product of the invention comprises IL-4 coupled to $CRM_{197}$, and is immunogenic, which means that the immunogenic product is capable of inducing anti-IL-4 antibodies in vivo in the conditions of TEST $C^{IL-4}$. In one embodiment, the immunogenic product of the invention is capable of inducing polyclonal anti-IL-4 antibodies in vivo, such as, for example, in the conditions of TEST $C^{IL-4}$.

TEST $C^{IL-4}$ is carried out according to the following method:

Specific amounts of total proteins (as determined, for example, by a Bradford protein assay) of the immunogenic product are injected in mice (older than 3 weeks of age), three to four times in 120 days. In one embodiment, TEST $C^{IL-4}$ is a heterologous system for example an immunogenic product comprising a non-murine IL-4 is injected in a mouse, and the test comprises administering a dose of total proteins ranging from about 0.3 to 30 μg. In another embodiment, TEST $C^{IL-4}$ is a homologous system, i.e., an immunogenic product comprising a murine IL-4 is injected in a mouse, and the test comprises administering a dose of total proteins ranging from about 5 to about 30 μg. Serum samples are obtained before immunization (pre-immune serum sample) and between day 39 and day 120 (test serum sample). ELISA anti-IL-4 are carried out as explained below.

Briefly, a 96 wells plate is coated with 1 μg/mL of IL-4 used for preparing the immunogenic product and incubated overnight at a temperature ranging from about 2° C. to about 8° C. The plate is then blocked with a blocking buffer during about 90 min at about 37° ° C. 100 μL of pre-immune sample and serum samples (pre-immune and test) are added to the wells at two-fold-serial dilution, such as, for example, starting at 500 $dil^{-1}$ until 256,000 $dil^{-1}$. An anti-mouse immunoglobulin labeled secondary antibody (such as, for example, an HRP conjugated antibody) is finally added to the wells and the ELISA is developed using any colorimetric means known in the art such as, for example, an OPD substrate solution.

In one embodiment, when the optical density of wells (490 nm) containing the test serum sample is at least about 1.5-fold, preferably at least about 2-fold superior to the optical density of wells containing the pre-immune serum sample, the immunogenic product is considered as immunogenic, which means that it has induced anti-IL-4 antibodies in vivo.

In this test, the titers were defined as the dilution of the serum where 50% of the ODmax minus OD of corresponding preimmune sample in the assay is reached. This mode of calculation is much more stringent than looking at the well-known seroconversion titers but provides more robust analysis and less false positive. Titers were expressed as serum dilution factors ($dil^{-1}$).

In another embodiment, in TEST $C^{IL-4}$, a titer value $\geq 250$ $dil^{-1}$, preferably $\geq 500$ $dil^{-1}$ indicates that the immunogenic product of the invention allows the production of binding antibodies against IL-4.

In one embodiment, the immunogenic product of the invention comprises IL-4 coupled to $CRM_{197}$ and is capable of neutralizing IL-4 activity in condition of hereunder cited TEST $D^{IL-4}$. According to the invention, TEST $D^{IL-4}$ is performed to evaluate the neutralizing capacity of the serum obtained from mice immunized with the immunogenic product. Such evaluation may be assessed by a colorimetric T cell proliferation assay for the murine product or a reporter gene bioassay for the human product, using HEK-Blue™ IL-4/IL-13 cells. In these cells, stimulation with IL-4 or IL-13 activates the JAK/STAT6 pathway with the subsequent production of SEAP. Neutralizing antibodies anti-IL-4 induced by immunization with the immunogenic products can then be evaluated by assessing SEAP levels in the supernatant.

In one embodiment, the immunogenic product of the invention comprises murine IL-4, and TEST $D^{IL-4}$ is a colorimetric T cell proliferation assay carried out using CTLL-2 cells in the following method:
CTLL-2 cells are grown in presence of IL-2 at 10 ng/mL final with RPMIc and 10% (v/v) FBS,
Serum samples are added at 1/200 final and positive control polyclonal anti-IL-4 antibody at 1 g/mL final and 2-fold serially diluted in 25 μL per well RPMIc+ 10% (v/v) FBS in culture plates.
muIL-4 is then added at 2 ng/mL final to serum samples and control are then incubated for 1 hour at room temperature.
Then, 20,000 CTLL-2 cells per well are added to pre-incubated samples. Plates are then incubated for about 48 h at about 37° C., 5% $CO_2$ in a humidified incubator.
At the end of the culture, cell viability is assessed using methods well-known in the art. One example of such methods is the following: 40 μL/well of a solution of MTS/PMS are added to the wells and the plate is incubated for another 4 h at 37° ° C. 5% $CO_2$. The plate is then read at 490 nm on a spectrophotometer.

In another embodiment, the immunogenic product of the invention comprises human IL-4, and TEST $D^{IL-4}$ is a reporter gene bioassay carried out using HEK-Blue™ IL-4/IL-13 cells and comprises the following steps:
HEK-Blue™ IL-4/IL-13 cells are plated in an assay medium composed of DMEM GlutaMAX™ supplemented with 10% (v/v) FBS, 10 mM HEPES, 50 U/mL penicillin and 50 μg/mL streptomycin.
Serum samples, control antibody (polyclonal goat anti-IL-4 antibody) were diluted in assay medium at 1/200 and 1 μg/mL final, respectively. Serum samples or control antibody were two-fold serially diluted in a 96 round-bottomed well plates in the presence of 0.25 ng/ml final of IL-4 for one hour incubation at room temperature.
These mixes were then added to pre-seeded plates containing 40,000 HEK-Blue™ IL-4/IL-13 cells per well. Plates were incubated for about 24 h at about 37° C., in a 5% $CO_2$ humidified incubator.
At the end of the culture, activation pathway is assessed using methods well-known in the art. One example of such methods is the following: 90 μL/well of QUANTI-Blue™ solution are added to 10 μL/well of cell supernatant. Then, plates are incubated for 1 h at 37° C., in a 5% $CO_2$ humidified incubator. Plates are then read at 625 nm on a spectrophotometer.

$NC_{50}$ results were expressed as the serum dilution factor ($dil^{-1}$) neutralizing 50% of muIL-4 or IL-4 activity. The $NC_{50}$ is determined by interpolating the serum dilution resulting in a 50% of IL-4 activity on the abscissa axis.

In TEST $D^{IL-4}$, a $NC_{50}$ value $\geq 100$ $dil^{-1}$, preferably $\geq 200$ $dil^{-1}$ indicates that the immunogenic product of the invention allows the production of neutralizing antibodies against IL-4. In one embodiment, the neutralizing antibodies against IL-4 induced by the administration of the immunogenic product of the invention are polyclonal.

In one embodiment, the at least one cytokine is IL-13.
In one embodiment, IL-13 is recombinant. Recombinant IL-13 may be obtained by conventional methods known in the art using the nucleic sequence encoding IL-13. For example, recombinant IL-13 may be obtained by culturing cells containing an expression vector comprising the gene of IL-13, harvesting inclusion bodies and purifying the IL-13 cytokine. Recombinant IL-13 is commercially available and may be purchased, for example, from PeproTech (Rocky Hill, NJ, US).

In one embodiment of the present invention, IL-13 is derived from a mammal.

In one embodiment, IL-13 is a variant of a mammal IL-13, wherein said variant present at least about 70%, 75, 80, 85, 90, 95% or more identity with the mammal IL-13 from which it derives. In one embodiment, IL-13 is full-length IL-13.

In another embodiment, the at least one cytokine is a fragment of IL-13, such as, for example, a fragment of IL-13 comprising at least about 50, 55, 60, 65, 70, 75, 80, 85, 90, 95, 100, 105, 110, 115, or 120 amino acids (preferably contiguous amino acids) of the IL-13 from which it derives.

In one embodiment, said fragment comprises at least one specific epitope of IL-13.

In one embodiment of the present invention, IL-13 is human IL-13, preferably recombinant human IL-13. Human IL-13 has a sequence SEQ ID NO: 6 (UniProt ID: P35225-1).

SEQ ID NO: 6
LTCLGGFASPGPVPPSTALRELIEELVNITQNQK-APLCNGSMVWSINLTAGMYCAAL ESLINVSGCSAIE-KTQRMLSGFCPHKVSAGQFSSLHVRDTKIEVAQFV-KDLLLHLKKL FREGREN

In one embodiment, IL-13 is a variant of SEQ ID NO: 6, wherein said variant presents at least about 70%, 75, 80, 85, 90, 95% or more identity with SEQ ID NO: 6.

In one embodiment, IL-13 is full-length human IL-13.

In another embodiment, the at least one cytokine is a fragment of human IL-13, such as, for example, a fragment of human IL-13 comprising at least about 50, 55, 60, 65, 70, 75, 80, 85, 90, 95, 100, 105, 110, 115, or 120 amino acids (preferably contiguous amino acids) of SEQ ID NO: 6.

In one embodiment, said fragment comprises at least one specific epitope of human IL-13.

In one embodiment of the present invention, IL-13 is murine IL-13, preferably recombinant murine IL-13. Murine IL-13 has a sequence SEQ ID NO: 7 (UniProt ID: P20109-1).

SEQ ID NO: 7
PVPRSVSLPLTLKELIEELSNITQDQTPLCNGSMV-WSVDLAAGGFCVALDSLTNISNCNAIYRTQRIL HGL-CNRKAPTTVSSLPDTKIEVAHFITKLLSYTKQL-FRHGPF

In one embodiment, IL-13 is a variant of SEQ ID NO: 7, wherein said variant presents at least about 70%, 75, 80, 85, 90, 95% or more identity with SEQ ID NO: 7.

In one embodiment, IL-13 is full-length murine IL-13.

In another embodiment, the at least one cytokine is a fragment of murine IL-13, such as, for example, a fragment of murine IL-13 comprising at least about 50, 55, 60, 65, 70, 75, 80, 85, 90, 95, 100, or 105 amino acids (preferably contiguous amino acids) of SEQ ID NO: 7.

In one embodiment, said fragment comprises at least one specific epitope of murine IL-13.

In one embodiment of the present invention, IL-13 is canine IL-13, preferably recombinant canine IL-13. Canine IL-13 has a sequence SEQ ID NO: 8 (UniProt ID: Q9N0W9-1).

SEQ ID NO: 8
SPSPVTPSPTLKELIEELVNITQNQASLCNGSMVW-SVNLTAGMYCAALESLINVSDCS AIQRTQRMLKAL-CSQKPAAGQISSERSRDTKIEVIQLVKNLLTYVRGV-YRHGNFR

In one embodiment, IL-13 is a variant of SEQ ID NO: 8, wherein said variant presents at least about 70%, 75, 80, 85, 90, 95% or more identity with SEQ ID NO: 8.

In one embodiment, IL-13 is full-length canine IL-13.

In another embodiment, the at least one cytokine is a fragment of canine IL-13, such as, for example, a fragment of canine IL-13 comprising at least about 50, 55, 60, 65, 70, 75, 80, 85, 90, 95, 100, 105 or 110 amino acids (preferably contiguous amino acids) of SEQ ID NO: 8.

In one embodiment, said fragment comprises at least one specific epitope of canine IL-13.

In one embodiment, the immunogenic product of the invention comprises IL-13 coupled to $CRM_{197}$ at a molar ratio IL13:$CRM_{197}$ ranging from about 16:1 to about 1:2, preferably from about 8:1 to about 2:1, more preferably of about 4:1.

In one embodiment of the invention, the immunogenic product comprises IL-13 coupled to $CRM_{197}$ and is recognized by anti-IL-13 antibodies.

The fact that the immunogenic product comprises IL-13 coupled to $CRM_{197}$ and is recognized by anti-IL-13 antibodies may be verified by conventional methods known in the art. An example of such methods is a sandwich ELISA anti-cytokine/carrier protein, using for example a detection antibody labelled with biotin, a streptavidin HRP amplification system and/or an OPD substrate solution.

In one embodiment, the TEST $A^{IL-13}$ described herein may be used for verifying that the immunogenic product of the invention comprises IL-13 coupled to $CRM_{197}$ and is recognized by anti-IL-13 antibodies. TEST $A^{IL-13}$ is an ELISA test anti-IL-13/$CRM_{197}$.

TEST $A^{IL-13}$ is carried out as follows:
Coating a plate with a capture antibody directed to $CRM_{197}$, such as, for example anti-*diphtheriae* toxin antibodies from Abcam (AB53828) or Bio-Rad (3710-0956, 3710-0150 or 3710-0100), Blocking the plate with a blocking buffer (such as, for example, casein 2% (w/v) in PBS for example) during about 90 min at about 37° C., Incubating during about 90 min at about 37° ° C. the plate with a two-fold-serial dilution of the immunogenic product starting at 250 ng/ml or with negative controls such as, for example, IL-13 and $CRM_{197}$, Incubating during about 90 min at about 37° ° C. the plate with a biotinylated detection antibody directed to IL-13, such as, for example anti-IL-13 biotinylated antibodies from SouthernBiotech (10126-08), Pepro-Tech (500-P13BT) or R&D systems (BAF213), or murine anti-IL-13 biotinylated antibodies from Bio-Rad (AAM34B), PeproTech (500-P178BT) or R&D systems (BAF413), Incubating the plate with streptavidin-HRP during about 30 min at about 37° C. and developing the complex with an OPD substrate solution during about 30 min, After stopping the enzymatic reaction, the intensity of the resulting color is determined by spectrophotometric methods at 490 nm.

In one embodiment, when the optical density of wells containing the immunogenic product of the invention at 25 ng per well is at least about 3-fold, preferably at least about 5-fold, and more preferably at least about 10-fold the optical density of wells containing a negative control, the person skilled in the art may conclude that the immunogenic product of the invention (i) is recognized by anti-IL-13 antibodies and (ii) comprises IL-13 coupled to $CRM_{197}$.

In another embodiment, the immunogenic product of the invention comprises IL-13 coupled to $CRM_{197}$, and is strongly inactivated, which means that the immunogenic product shows less than about 15% of residual activity in condition of hereunder cited TEST $B^{IL-13}$, preferably less than about 10% of residual activity, and more preferably less than about 5% of residual activity. TEST $B^{IL-13}$ is a reporter gene bioassay using HEK-Blue™ IL-4/IL-13 cells. In these cells, stimulation with IL-4 or IL-13 activates the JAK/STAT6 pathway with the subsequent production of SEAP. IL-13 biological activity comprised in the immunogenic product of the invention can then be evaluated by assessing SEAP levels in the supernatant.

In one embodiment, TEST $B^{IL-13}$ uses a HEK-Blue™ IL-4/IL-13 cell line purchased from InvivoGen. In presence of IL-13 murine or human, the STAT6 pathway of HEK-Blue™ IL-4/IL-13 cell line is activated and produces SEAP which can be quantified using methods well-known in the art.

TEST $B^{IL-13}$ comprises the following steps:
HEK-Blue™ IL-4/IL-13 cells are plated in an assay medium composed of DMEM GlutaMAX™ supplemented with 10% (v/v) FBS, 10 mM HEPES, 50 U/mL penicillin and 50 μg/mL streptomycin, Human immunogenic product (IL-13/$CRM_{197}$) and IL-13 control are two-fold serially diluted in assay medium at 8000 and 10 ng/mL final, respectively.

Murine immunogenic product (muIL-13/$CRM_{197}$) and muIL-13 control are two-fold serially diluted in assay medium at 250 and 10 ng/mL final, respectively.

The samples are then transferred to pre-seeded plates containing 40,000 of HEK-Blue™ IL-4/IL-13 cells per well. Plates are incubated for about 24 h about 37° C., in a 5% $CO_2$ humidified incubator.

At the end of the culture, activation pathway is assessed using methods well-known in the art. One example of such methods is the following: 90 μL/well of QUANTI-Blue™ solution (purchased from InvivoGen) are added to 10 μL/well of cell supernatant. Then, plates are incubated for about 1 h at about 37°C, in a 5% $CO_2$ humidified incubator. Plates are then read at 625 nm on a spectrophotometer.

The effective dose 50 ($ED_{50}$) value, corresponding to the amount of the immunogenic product (or IL-13) resulting in 50% of maximum signal recorded for the considered samples, is determined by interpolating the ODmax/2 values to the corresponding sample concentrations using a four parameter logistic (4PL) nonlinear regression from the whole dilution points.

In TEST $B^{IL-13}$, the inactivation factor is calculated by dividing the $ED_{50}$ of the tested immunogenic product of the invention by the corresponding $ED_{50}$ of the IL-13 control standard curves. A result with an inactivation factor >20 means that for the same amount of protein, the IL-13 activity in the immunogenic product correspond to less than 5% of native IL-13 activity. In one embodiment, an inactivation factor superior to about 2, 2.5, 3.33, 5 or 10, preferably to about 20, indicates that the immunogenic product is strongly inactivated. In one embodiment, a residual activity inferior to about 50%, 40%, 30%, 20% or 10%, preferably inferior to about 5% of native IL-13 activity indicates that the immunogenic product is strongly inactivated.

In one embodiment, the immunogenic product of the invention comprises IL-13 coupled to $CRM_{197}$, and is immunogenic, which means that the immunogenic product is capable of inducing antibodies anti-IL-13 in vivo in the conditions of TEST $C^{IL-13}$. In one embodiment, the immunogenic product of the invention is capable of inducing polyclonal anti-IL-13 antibodies in vivo, such as, for example, in the conditions of TEST $C^{IL-13}$.

TEST $C^{IL-13}$ is carried out according to the following method:

Specific amounts of total proteins (as determined, for example, by a Bradford protein assay) of the immunogenic product is injected in mice (older than 3 week of age), at least three times in 120 day. In one embodiment, TEST $C^{IL-13}$ is a heterologous system for example an immunogenic product comprising a non-murine IL-13 is injected in a mouse, and the test comprises administering a dose of total proteins ranging from about 0.3 to 10 μg. In another embodiment, TEST $C^{IL-13}$ is a homologous system for example an immunogenic product comprising a murine IL-13 is injected in a mouse, and the test comprises administering a dose of total proteins ranging from about 5 to about 30 μg. Serum samples are obtained before immunization (pre-immune serum sample) and between day 39 and day 120 (test serum sample). ELISA anti-IL-13 are carried out as explained below.

Briefly, a 96-well plate is coated with 1 μg/mL of IL-13 used for preparing the immunogenic product and incubated overnight at a temperature ranging from about 2° ° C. to about 8° C. The plate is then blocked with a blocking buffer during about 90 min at about 37° C. 100 μL of pre-immune sample and serum samples (pre-immune and test) are added to the wells at two-fold-serial dilution, such as, for example, starting at 500 $dil^{-1}$ until 256,000 $dil^{-1}$. An anti-mouse immunoglobulin labeled secondary antibody (such as an HRP conjugated antibody) is finally added to the wells and the ELISA is developed using any colorimetric means known in the art, such as, for example, OPD substrate solution.

In one embodiment, when optical density of wells containing the test serum sample is at least about 1.5-fold, preferably at least about 2-fold superior to the optical density of wells containing the pre-immune serum sample, the immunogenic product is considered as immunogenic, which means that it has induced anti-IL-13 antibodies in vivo.

In this test, the titers were defined as the dilution of the serum where 50% of the ODmax minus OD of corresponding pre-immune sample in the assay is reached. This mode of calculation is much more stringent than looking at the well-known seroconversion titers but provides more robust analysis and less false positive. Titers were expressed as serum dilution factors ($dil^{-1}$).

In another embodiment, in TEST $C^{IL-13}$, a titer value ≥250 $dil^{-1}$, preferably ≥500 $dil^{-1}$ indicates that the immunogenic product of the invention allows the production of binding antibodies against IL-13.

In one embodiment, the immunogenic product of the invention comprises IL-13 coupled to $CRM_{197}$ and is capable of neutralizing IL-13 activity in condition of hereunder cited TEST $D^{IL-13}$. According to the invention, TEST $D^{IL-13}$ is performed to evaluate the neutralizing capacity of the serum obtained from mice immunized with the immunogenic product using the reporter cell line HEK-Blue™ IL-4/IL-13. In these cells, stimulation with IL-4 or IL-13 activates the JAK/STAT6 pathway with the subsequent production of SEAP. Neutralizing antibodies anti-IL-13 induced by immunization with the immunogenic products can then be evaluated by assessing SEAP levels in the supernatant.

TEST $D^{IL-13}$ is carried out using HEK-Blue™ IL-4/IL-13 cells in the following method:

In presence of bioactive IL-13, the STAT6 pathway of HEK-Blue™ IL-4/IL-13 cell line is activated and produces SEAP which can be quantified using methods well-known in the art. This assay is carried to the following method:

HEK-Blue™ IL-4/IL-13 cells are cultured in an assay medium composed of DMEM GlutaMAX™ supplemented with 10% (v/v) FBS, 10 mM HEPES, 50 U/mL penicillin and 50 μg/mL streptomycin.

Serum samples obtained following human immunogenic product administration and control antibody (polyclonal goat anti-IL-13 antibody such as, for example, AF-213-NA) were diluted in assay medium at 1/100 and 4 μg/mL final respectively and added to 2 ng/ml of IL-13.

Serum samples obtained following murine immunogenic product administration and control antibody (polyclonal goat anti-muIL-13 antibody such as AF-413-NA) were diluted in assay medium at 1/100 and 1 μg/mL final respectively and added to 2 ng/ml of muIL-13.

These mixes were then incubated 1 h at room temperature before being added to 40,000 HEK-Blue™ IL 4/IL-13 cells per well. Plates were incubated for about 24 h at about 37° C., in a 5% $CO_2$ humidified incubator.

At the end of the culture, activation pathway is assessed using methods well-known in the art. One example of such methods is the following: 90 μL/well of QUANTI-Blue™ solution are added to 10 μL/well of cell supernatant. Then, plates are incubated for 1 h at 37° C., in a 5% $CO_2$ humidified incubator. Plates are then read at 625 nm on a spectrophotometer.

$NC_{50}$ results were expressed as the serum dilution factor ($dil^{-1}$) neutralizing 50% of muIL-13 or IL-13 activity. The $NC_{50}$ is determined by interpolating the serum dilution resulting in a 50% of IL-13 activity on the abscissa axis.

In TEST $D^{IL-13}$, a $NC_{50}$ value ≥50, preferably a $NC_{50}$ value ≥100 $dil^{-1}$ indicates that the immunogenic product of the invention allows the production of neutralizing antibodies against IL-13. In one embodiment, the neutralizing antibodies against IL-13 induced by the administration of the immunogenic product of the invention are polyclonal.

In one embodiment, the immunogenic product of the invention comprises IL-4 and IL-13.

In one embodiment, IL-4, IL-13 or both are recombinant.

In one embodiment, IL-4 and IL-13 both originate from the same mammal. In one embodiment, IL-4, IL-13 or both are human.

In one embodiment, IL-4 is a variant of human IL-4, wherein said variant presents at least about 70%, 75, 80, 85, 90, 95% or more identity with human IL-4. In one embodiment, IL-13 is a variant of human IL-13, wherein said variant presents at least about 70%, 75, 80, 85, 90, 95% or more identity with human IL-13.

In one embodiment, IL-4, IL-13 or both are full-length.

In one embodiment, IL-4 is a fragment of full-length IL-4. In one embodiment, IL-13 is a fragment of full-length IL-13.

In one embodiment, the immunogenic product of the invention comprises IL-4 and IL-13, both coupled to $CRM_{197}$.

In one embodiment, the molar ratio cytokines (i.e., IL-4 and IL-13):$CRM_{197}$ ranges from about 16:1 to about 1:2, preferably from about 8:1 to about 2:1, more preferably of about 4:1.

In one embodiment, the molar ratio IL-4:$CRM_{197}$ ranges from about 8:1 to about 1:2, preferably from about 4:1 to about 1:1, more preferably of about 2:1.

In one embodiment, the molar ratio IL-13:$CRM_{197}$ ranges from about 8:1 to about 1:2, preferably from about 4:1 to about 1:1, more preferably of about 2:1.

In one embodiment, the molar ratio IL-4:IL-13 ranges from about 5:1 to about 1:5, preferably from about 2:1 to about 1:2, more preferably of about 1:1.

In one embodiment, the immunogenic product of the invention comprises IL-4 and IL-13 coupled to $CRM_{197}$ and is recognized by anti-IL-4 and anti-IL-13 antibodies.

The fact that the immunogenic product comprises IL-4 and IL-13 coupled to $CRM_{197}$ and is recognized by anti-IL-4 and anti-IL-13 antibodies may be verified by conventional methods known in the art. An example of such methods is a sandwich ELISA anti-cytokine/carrier protein, using for example a detection antibody labelled with biotin, a streptavidin HRP amplification system and/or an OPD substrate solution.

In one embodiment, the recognition of the immunogenic product by anti-IL-4 and anti-IL-13 antibodies may be verified using the TESTS A (TEST $A^{IL-4}$ and TEST $A^{IL-13}$) described herein.

In one embodiment, the immunogenic product of the invention comprises IL-4 and IL-13 coupled to $CRM_{197}$ and is strongly inactivated, which means that the immunogenic product shows less than about 10% of IL-4 initial activity, preferably less than about 5% and preferably less than about 1% of IL-4 initial activity and less than about 15% of IL-13 initial activity, preferably less than about 10% and preferably less than about 5% of IL-13 initial activity in condition of hereunder cited TESTS B (TEST $B^{IL-4}$ and TEST $B^{IL13}$).

In one embodiment, the immunogenic product comprises IL-4 and IL-13 coupled to $CRM_{197}$ and is immunogenic, which means that the immunogenic product is capable of (i) inducing anti-IL-4 antibodies in vivo in the conditions of TEST $C^{IL-4}$ and (i) inducing anti-IL-13 antibodies in vivo in the conditions of TEST $C^{IL-13}$. In one embodiment, the immunogenic product of the invention is capable of inducing polyclonal anti-IL-4 antibodies in vivo, such as, for example, in the conditions of TEST $C^{IL-4}$ and anti-IL-13 antibodies in vivo, such as, for example, in the conditions of TEST $C^{IL-13}$.

In one embodiment, the immunogenic product of the invention comprises IL-4 and IL-13 coupled to $CRM_{197}$ and is capable of (i) neutralizing IL-4 activity in condition of herein cited TEST $D^{IL-4}$ and (ii) neutralizing IL-13 activity in condition of hereunder cited TEST $D^{IL-13}$. In one embodiment, the neutralizing antibodies against IL-4 and IL-13 induced by the administration of the immunogenic product of the invention are polyclonal.

The present invention further relates to a method for producing an immunogenic product comprising at least one cytokine selected from IL-4, IL-13 and mixtures thereof, coupled with a carrier protein, preferably $CRM_{197}$, wherein the method comprises the following steps:
  a) contacting the at least one cytokine with a heterobifunctional crosslinker containing a NHS-ester, preferably N-[γ-maleimidobutyryloxy]-succinimide ester (sGMBS);
  b) contacting the carrier protein with a heterobifunctional crosslinker containing a NHS-ester, preferably N-succinimidyl-S-acetylthioacetate (SATA) to generate a carrier-SATA complex;
  c) contacting the sGMBS-cytokine complex obtained at step (a) with the carrier SATA complex obtained at step (b).

In one embodiment, in step a), the reaction buffer is in a liquid, preferably aqueous, solution.

In one embodiment, in step a), the reaction buffer is at a pH ranging from about 6 to about 8, preferably ranging from about 6.5 to about 7.5, more preferably at about pH 7.2.

In one embodiment, in step a), the cytokine is present in solution at a concentration ranging from about 0.1 to about 10 mg/mL, preferably from about 0.5 to about 5 mg/ml, more preferably of about 1 mg/mL.

In one embodiment, in step a), the heterobifunctional crosslinker containing a NHS-ester, preferably sGMBS, is prepared in reaction buffer at a concentration ranging from 1 mM to 100 mM, preferably from 5 mM to 50 mM and more preferably at 10 mM.

In one embodiment, in step a), IL-4 and the heterobifunctional crosslinker containing a NHS-ester, preferably sGMBS, are mixed at a IL-4:heterobifunctional crosslinker containing a NHS-ester, preferably sGMBS, molar ratio ranging from about 1:120 to about 1:1, preferably from about 1:50 to about 1:10.

In one embodiment, in step a), IL-13 and the heterobifunctional crosslinker containing a NHS-ester, preferably sGMBS, are mixed at a IL-13:heterobifunctional crosslinker containing a NHS-ester, preferably sGMBS, molar ratio ranging from about 1:120 to about 1:1, preferably from about 1:50 to about 1:10.

In one embodiment, in step a), the at least one cytokine is incubated with the heterobifunctional crosslinker containing a NHS-ester, preferably sGMBS, for a period ranging from about 30 min to about 120 min, preferably from about 45 to about 90 minutes and more preferably during at least 60 minutes.

In one embodiment, in step a), the contacting step of the at least one cytokine with the heterobifunctional crosslinker containing a NHS-ester, preferably sGMBS, is performed at a temperature ranging from about 15° C. to about 35° C., preferably from about 18° C. to about 27° C.

In one embodiment, following step a), small compounds having a molecular weight of less than about 10 kDa, less than about 5 kDa or less than about 3 kDa that are present in the reaction mixture are removed. These small compounds encompass mainly the excess of the heterobifunctional crosslinker containing a NHS-ester (and NHS-ester hydrolysis-related side-products), preferably sGMBS, and the excess molecules that have not reacted. Such removing may be performed by methods well known in the art.

In one embodiment, at the end of step a), the protein content is determined by Bradford assay or by any method well known in the art.

In one embodiment, in step b), the reaction buffer is in a liquid, preferably aqueous, solution.

In one embodiment, in step b), the reaction buffer is at a pH ranging from about 6 to about 8, preferably ranging from about 6.5 to about 7.5, more preferably at about pH 7.2.

In one embodiment, in step b), $CRM_{197}$ is present in solution at a concentration ranging from about 0.2 to about 20 mg/mL, preferably from about 1 to about 10 mg/ml, more preferably of about 2 mg/mL.

In one embodiment, in step b), the heterobifunctional crosslinker containing a NHS-ester, preferably SATA, is present in solution, preferably in DMSO, at a concentration ranging from 20 mM to about 500 mM, preferably from about 50 mM to about 200 mM and more preferably at a concentration of about 100 mM.

In on embodiment, in step b), $CRM_{197}$ and the heterobifunctional crosslinker containing a NHS-ester, preferably SATA, are mixed at a carrier:heterobifunctional crosslinker containing a NHS-ester, preferably SATA, molar ratio ranging from about 1:320 to about 1:10.

In one embodiment, in step b), $CRM_{197}$ is incubated with the heterobifunctional crosslinker containing a NHS-ester, preferably SATA, for a period of time ranging from about 10 min to about 60 min, preferably from about 15 minutes to about 45 minutes and more preferably during 30 minutes.

In one embodiment, the contacting step b) is performed at a temperature ranging from about 15° C. to about 35° C., preferably from about 18° ° C. to about 27° C.

In one embodiment, following step b), small compounds having a molecular weight of less than about 10 kDa, less than about 5 kDa or less than about 3 kDa that are present in the reaction mixture are removed. These small compounds encompass mainly the excess of the heterobifunctional crosslinker containing a NHS-ester (and NHS-ester hydrolysis-related side-products), preferably SATA, DMSO, and the excess molecules that have not reacted. Such removing may be performed by methods well known in the art.

In one embodiment, after step b), the complexes between $CRM_{197}$ and the heterobifunctional crosslinker containing a NHS-ester, preferably SATA, are deprotected to convert the protecting group (the heterobifunctional crosslinker containing a NHS-ester, preferably SATA) into a functional group. In one embodiment, said deprotecting step is carried out after a step of removing small compounds having a molecular weight of less than about 10 kDa, less than about 5 kDa or less than about 3 kDa that are present in the reaction mixture Examples of method for deprotecting a molecule are well known in the art and include, without limitation, the use of hydroxylamine, the use of methoxylamine, or the use of a base (such as, for example, NaOH, KOH, $K_2CO_3$, MeONa, $NH_3$ in methanol).

In one embodiment, the deprotecting step comprises the addition to the reaction mixture of a hydroxylamine solution, preferably at a final concentration ranging from about 10 mM to about 500 mM, preferably from about 20 mM to about 100 mM, more preferably at about 50 mM.

In one embodiment, the hydroxylamine solution is incubated with the reaction mixture for a period of time ranging from about 60 min to about 180 min, preferably from about 90 minutes to about 150 minutes, and more preferably during 120 minutes.

In one embodiment, the hydroxylamine solution is added at 50 mM during 120 minutes.

In one embodiment, the incubation of the hydroxylamine solution with the reaction mixture is performed at a temperature ranging from about 15° C. to about 35° C., preferably from about 18° C. to about 27° C.

In one embodiment, following the deprotection step, small compounds having a molecular weight of less than about 10 kDa, 5 kDa or 3 kDa that are present in the reaction mixture are removed. These small compounds encompass mainly the excess of hydroxylamine and potential residual SATA from the previous step. Such removing may be performed by methods well known in the art.

In one embodiment, at the end of step b), the protein content is determined by Bradford assay or by any method well known in the art.

Then, in step c) of the method of the invention, the final product of step a) is contacted with the final product of step b), thereby producing the immunogenic product of the invention.

In one embodiment, in step c), the final product of step a) comprising IL-4 and the final product of step b) comprising $CRM_{197}$ are contacted at a molar ratio IL-4:$CRM_{197}$ ranging from about 16:1 to about 1:2, preferably from about 8:1 to about 2:1, more preferably of about 4:1.

In one embodiment, in step c), the final product of step a) comprising IL-13 and the final product of step b) comprising $CRM_{197}$ are contacted at a ratio IL-13:$CRM_{197}$ ranging from about 16:1 to about 1:2, preferably from about 8:1 to about 2:1, more preferably of about 4:1.

In another embodiment of step c), a final product of step a) comprising IL-4, a final product of step a) comprising IL-13 and a final product of step b) are contacted. In one embodiment, said contacting step is carried out at a molar ratio cytokines (i.e., IL-4 and IL-13):$CRM_{197}$ ranging from about 16:1 to about 1:2, preferably from about 8:1 to about 2:1, more preferably of about 4:1. In one embodiment, said contacting step is carried out at a molar ratio IL-4:$CRM_{197}$ ranging from about 8:1 to about 1:2, preferably from about 4:1 to about 1:1, more preferably of about 2:1. In one embodiment, said contacting step is carried out at a molar ratio IL-13:$CRM_{197}$ ranging from about 8:1 to about 1:2, preferably from about 4:1 to about 1:1, more preferably of about 2:1. In one embodiment, said contacting step is carried out at a molar ratio IL-4:IL-13 ranging from about 5:1 to about 1:5, preferably from about 2:1 to about 1:2, more preferably of about 1:1.

In one embodiment, in step c), the reaction buffer is in a liquid, preferably aqueous, solution.

In one embodiment, in step c), the reaction buffer is at a pH ranging from about 6 to about 8, preferably ranging from about 6.5 to about 7.5, more preferably at about pH 7.2.

In one embodiment of step c), the contacting step is carried out for a period of time ranging from about 2 hours to about 26 hours, preferably from about 10 to 18 hours, more preferably from about 12 to about 18 hours.

In one embodiment, the incubation step c) is carried out at a temperature ranging from about 2° C. to 10° C., preferably from about 3° C. to about 7° C., and more preferably at about 4° C.

In one embodiment, following step c), small compounds having a molecular weight of less than about 100 kDa, less than about 50 kDa, less than about 25 kDa, less than about 10 kDa, less than about 5 kDa or less than about 3 kDa that are present in the reaction mixture are removed. These small compounds encompass mainly the excess molecules that have not reacted. Such removing may be performed by methods well known in the art.

In one embodiment, the immunogenic product obtained at step c) is concentrated. The concentration of the immunogenic product may be performed by the skilled artisan by any technique known in the art, such as, for example, by a centrifugal ultrafiltration method that may optionally be combined with sterile filtration.

In one embodiment, the immunogenic product obtained at step c) and optionally concentrated is lyophilized.

The present invention further relates to an immunogenic product susceptible to be obtained by the method of the present invention.

The present invention further relates to a composition comprising, consisting essentially of or consisting of at least one immunogenic product as described hereinabove. In one embodiment, said composition may be referred to as an immunogenic composition.

The present invention further relates to a pharmaceutical composition comprising, consisting essentially of or consisting of at least one immunogenic product as described hereinabove, and at least one pharmaceutically acceptable excipient.

Pharmaceutically acceptable excipients that may be used in the pharmaceutical composition of the invention include, but are not limited to, ion exchangers, alumina, aluminum stearate, lecithin, serum proteins, such as, for example, human serum albumin, buffer substances such as, for example, phosphates, glycine, sorbic acid, potassium sorbate, partial glyceride mixtures of saturated vegetable fatty acids, water, salts or electrolytes, such as, for example, protamine sulfate, disodium hydrogen phosphate, potassium hydrogen phosphate, sodium chloride, zinc salts, colloidal silica, magnesium trisilicate, polyvinyl pyrrolidone, cellulose-based substances (for example sodium carboxymethylcellulose), polyethylene glycol, polyacrylates, waxes, polyethylene-polyoxypropylene-block polymers, polyethylene glycol and wool fat.

The present invention further relates to a medicament comprising, consisting essentially of or consisting of at least one immunogenic product as described hereinabove.

As used herein, the term "consisting essentially of", with reference to a composition, pharmaceutical composition or medicament, means that the at least one immunogenic product of the invention is the only one therapeutic agent or agent with a biologic activity within said composition, pharmaceutical composition or medicament.

In one embodiment, the composition, pharmaceutical composition or medicament of the invention comprises or consists essentially of an immunogenic product comprising IL-4 coupled with $CRM_{197}$.

In one embodiment, the composition, pharmaceutical composition or medicament of the invention comprises or consists essentially of an immunogenic product comprising IL-13 coupled with $CRM_{197}$.

In one embodiment, the composition, pharmaceutical composition or medicament of the invention comprises or consists essentially of an immunogenic product comprising $CRM_{197}$ coupled with both IL-4 and IL-13.

In one embodiment, the composition, pharmaceutical composition or medicament of the invention comprises or consists essentially of a mixture of an immunogenic product comprising IL-4 coupled with $CRM_{197}$ and of an immunogenic product comprising IL-13 coupled with $CRM_{197}$, at a weight ratio ranging from about 10:1 to about 1:10, preferably at a weight ratio ranging from about 4:1 to 1:4.

In one embodiment, the composition, pharmaceutical composition or medicament of the invention is a vaccine composition. In one embodiment of the invention, the vaccine composition of the invention comprises at least one adjuvant.

This invention further relates to a formulation of the composition, pharmaceutical composition, medicament or vaccine of the invention, wherein the composition, pharmaceutical composition, medicament or vaccine is adjuvanted.

In one embodiment, the composition, pharmaceutical composition, medicament or vaccine of the invention thus comprise one or more adjuvants.

Suitable adjuvants that may be used in the present invention include, but are not limited to:

(1) aluminum salts (alum), such as, for example, aluminum hydroxide, aluminum phosphate, aluminum sulfate, etc.;

(2) oil-in-water emulsion formulations (with or without other specific immunostimulating agents such as, for example, muramyl peptides (defined below) or bacterial cell wall components), such as, for example, squalene-based emulsions (e.g., squalene-based oil-in-water emulsions) or squalane-based emulsions, such as, for example, (a) MF59 (a squalene-based oil-in-water adjuvant described in PCT Publ. No. WO 90/14837), containing 5% squalene, 0.5% Tween 80, and 0.5% span 85 (optionally containing various amounts of MTP-PE (see below, although not required)) formulated into submicron particles using a microfluidizer such as Model 110Y microfluidizer (Microfluidics, Newton, Mass.), (b) SAF, containing 10% Squalene, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Corixa, Hamilton, Mont.) containing 2% squalene, 0.2% Tween 80, and one or more bacterial cell wall components from the group consisting of 3-O-deaylated monophosphorylipid A (MPL™) described in U.S. Pat. No. 4,912,094 (Corixa), trehalose dimycolate (TDM), and cell wall skeleton (CWS), preferably MPL+CWS (Detox™);

(d) squalane based adjuvant comprising but not limited to the following composition: squalane 3.9%, w/v, sorbitan trioleate (0.47%, w/v), and polyoxyethylene (80) sorbitan monooleate (0.47%, w/v) dispersed in citrate buffer;

(3) water-in-oil emulsion formulations, such as, for example, ISA-51 or squalene-based water-in-oil adjuvant (e.g., ISA-720); Oil adjuvants suitable for use in water-in-oil emulsions may include mineral oils and/or metabolizable oils. Mineral oils may be selected from Bayol®, Marcol® and Drakeol, including Drakeol® 6VR (SEPPIC, France). ®. Metabolisable oils may be selected from SP oil (hereinafter described), Emulsigen (MPV Laboratories, Ralston, NZ), Montanide 264,266, 26 (Seppic SA, Paris, France), as well as vegetable oils, animal oils such as the fish oils squalane and squalene, and tocopherol and its derivatives.

(4) saponin adjuvants, such as Quil A or STIMULON™ QS-21 (Antigenics, Framingham, Mass.) (U.S. Pat. No. 5,057,540) may be used or particles generated therefrom such as ISCOMs (immunostimulating complexes);

(5) bacterial lipopolysaccharides, synthetic lipidA analogs such as aminoalkyl glucosamine phosphate compounds (AGP), or derivatives or analogs thereof, which are available from Corixa, and which are described in U.S. Pat. No. 6,113,918; one such AGP is 2-[(R)-3-Tetradecanoyloxytetradecanoylamino]ethyl 2-Deoxy-4-O-phosphono-3-Oi[(R)-3tetradecanoyloxytetradecanoyl]-2-[(R)-3-tetradecanoyloxytetradecanoyl amino]-b-Dglucopyranoside, which is also known as 529 (formerly known as RC529), which is formulated as an aqueous form or as a stable emulsion, synthetic polynudeotides such as oligonucleotides containing CpG motif(s) (U.S. Pat. No. 6,207,646);

(6) cytokines, such as interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), tumor necrosis factor (TNF), costimulatory molecules B7-1 and B7-2, etc.;

(7) detoxified mutants of a bacterial ADP-ribosylating toxin such as a cholera toxin (CT) either in a wild-type or mutant form, for example, where the glutamic acid at amino acid position 29 is replaced by another amino acid, preferably a histidine, in accordance with published international patent application number WO 00/18434 (see also WO 02/098368 and WO 02/098369), a pertussis toxin (PT), or an E. coli heat-labile toxin (LT), particularly LT-K63, LT-R72, CT-S109, PT-K9/G129 (see, e.g., WO 93/13302 and WO92/19265); and (8) other substances that act as immunostimulating agents to enhance the effectiveness of the composition. Muramyl peptides include, but are not limited to, N-acetylmuramyl-L-threonyl-D-isoglutamine (thr-MDP), N-acetylnormuramyl-L-alanine-2-(1'-2'dipalmitoyl-sn-glycero-3hydroxyphosphoryloxy)-ethylamine (MTP-PE), etc.

The adjuvant used may depend, in part, on the recipient organism. Moreover, the amount of adjuvant to administer will depend on the type and size of animal.

In one embodiment, the composition, pharmaceutical composition, medicament or vaccine composition of the invention is (or comprises) an emulsion further comprising one or more surfactant agents, and optionally at least one adjuvant as described hereinabove. In one embodiment, the emulsion is a water-in-oil emulsion or an oil-in-water emulsion.

Examples of surfactants that may be used in the present invention are well known in the art and include, but are not limited to, mannide monoleate such as Montanide® 80 marketed by Arlacel (SEPPIC, France), Tween 20, Tween 80, span 85, Triton X-100.

In one embodiment, the composition, pharmaceutical composition, medicament, vaccine composition of the invention comprises a therapeutically effective amount of at least one immunogenic product of the invention.

In one embodiment and for storage purposes, the immunogenic product or the composition, pharmaceutical composition, medicament, vaccine composition or emulsion of the invention is lyophilized.

In one embodiment, the composition, pharmaceutical composition, medicament, vaccine composition or emulsion of the invention may thus be presented in a freeze-dried (lyophilized) form. According to this embodiment, the immunogenic product of the invention is combined with one or more lyophilization auxiliary substances. Various lyophilization auxiliary substances are well known by the one skilled in the art and include, without limitation, sugars like lactose and mannitol.

In one embodiment, the composition, pharmaceutical composition, medicament, vaccine composition or emulsion of the invention may be mixed with stabilizers, e.g., to protect degradation-prone proteins from being degraded, to enhance the shelf-life of the immunogenic product, or to improve freeze-drying efficiency. Useful stabilizers include, but are not limited to, SPGA, carbohydrates (e.g., sorbitol, mannitol, trehalose, starch, sucrose, dextran or glucose), proteins (such as, for example, albumin or casein or degradation products thereof), mixtures of amino acids such as, for example, lysine or glycine, and buffers, such as, for example, alkali metal phosphates.

In one embodiment, the immunogenic product, composition, pharmaceutical composition, vaccine composition or emulsion of the invention may be administered by injection, topically (such as, for example, by transdermal delivery), rectally, nasally or vaginally.

In one embodiment, the immunogenic product, composition, pharmaceutical composition, medicament, vaccine composition or emulsion of the invention is in an adapted form for an injection. Thus, in one embodiment, the immunogenic product, composition, pharmaceutical composition, medicament, or vaccine composition of the invention is to be injected to the subject by intramuscular, intraperitoneal, or subcutaneous injection.

Examples of forms suitable for injectable use include, but are not limited to, sterile solutions or dispersions and sterile powders for the extemporaneous preparation of sterile injectable solutions or dispersions. The prevention against contamination by microorganisms can be brought about by adding in the composition preservatives such as, for example, various antibacterial and antifungal agents (for example, parabens, chlorobutanol, phenol, sorbic acid, thimerosal and the like). In an embodiment, it may be preferable to include isotonic agents, for example, sugars or sodium chloride, to reduce pain during injection. In one embodiment, prolonged absorption of the injectable compositions can be brought about by the use in the compositions of agents delaying absorption, for example, aluminum monostearate and gelatin.

In one embodiment, a lyophilized vaccine composition of the invention is solubilized in water for injection and gently mixed; then an immunoadjuvant as described hereinabove, is added; the mixture is gently mixed and charged into a suitable syringe. This invention thus also relates to a medical device, including a syringe filled or prefilled with a vaccine composition of the invention.

In one embodiment, the immunogenic product, composition, pharmaceutical composition, medicament, or vaccine composition of the invention is in an adapted form for topical administration. Examples of forms adapted for topical administration include, without being limited to, polymeric patch, or controlled-release patch, and the like.

In another embodiment, the immunogenic product, composition, pharmaceutical composition, medicament, vaccine composition or emulsion of the invention is in an adapted form for rectal administration. Examples of forms adapted for rectal administration include, without being limited to, suppository, micro enemas, enemas, gel, rectal foam, cream, ointment, and the like.

This invention also relates to the medical device which is the syringe filled or prefilled with the composition, pharmaceutical composition, medicament, or vaccine composition of the invention.

In one embodiment, said syringe is a dual chamber syringe, wherein one chamber comprises a solution with the immunogenic product of the invention and the other chamber comprises the adjuvant.

The invention also relates to a medical device comprising a vial prefilled with the immunogenic product of the invention or with the composition, pharmaceutical composition, medicament, or vaccine composition of the invention.

The present invention further relates to the immunogenic product, composition, pharmaceutical composition, medicament, or vaccine composition of the invention, for treating an inflammatory disorder in a subject.

The present invention thus further relates to a method for treating an inflammatory disorder in a subject, comprising administering to the subject the immunogenic product, composition, pharmaceutical composition, medicament, vaccine composition or emulsion of the invention.

The present invention further relates to a method for inducing an immune response against IL-4, IL-13 or both in a subject, comprising administering to the subject the immunogenic product, composition, pharmaceutical composition, medicament, or vaccine composition of the invention.

The present invention further relates to a method for inducing in a subject the production of antibodies that inhibits the biological activity or neutralizes the biological activity of IL-4, IL-13 or both, comprising administering to the subject the immunogenic product, composition, pharmaceutical composition, medicament, or vaccine composition of the invention. In one embodiment, the antibodies are polyclonal antibodies.

In one embodiment, the subject is affected, preferably is diagnosed, with an inflammatory disorder, in particular with a disorder associated with aberrant IL-4 and/or IL-13 expression or activity.

In one embodiment, the subject is a human. Preferably, according to this embodiment, the at least one cytokine comprised in the immunogenic product of the invention is human.

In one embodiment, the subject is a non-human mammal (such as, for example, a pet). Preferably, according to this embodiment, the at least one cytokine comprised in the immunogenic product of the invention originates from said non-human mammal.

In one embodiment, the inflammatory disorder is a disorder associated with aberrant IL-4 and/or IL-13 expression or activity.

Examples of inflammatory disorder include, but are not limited to, asthma (either allergic or non-allergic), allergic conditions (such as, for example, food allergies, venom allergy, cat allergy, drug allergy, hyper IgE syndrome, allergic rhinitis, allergic conjunctivitis and allergic enterogastritis), atopic disorders (such as, for example, atopic dermatitis, urticaria (including chronic idiopathic urticaria and chronic spontaneous urticaria), eczema), bullous pemphigoid, respiratory disorders (such as allergic and nonallergic asthma, chronic obstructive pulmonary disease (COPD)), nasal polyposis and other conditions involving airway inflammation (such as, for example, eosinophilia, fibrosis and excess mucus production including cystic fibrosis and pulmonary fibrosis, systemic sclerosis (SSc)); inflammatory and/or autoimmune disorders or conditions, gastrointestinal disorders or conditions (such as, for example, inflammatory bowel diseases (IBD) and eosinophilic esophagitis (EE), and eosinophilic-mediated gastrointestinal disease, ulcerative colitis, Crohn's disease and systemic lupus erythematosus); systemic lupus erythematosus, liver disorders or conditions (such as, for example, cirrhosis, and hepatocellular carcinoma), scleroderma; fibrotic diseases or disorders (such as, for example, fibrosis of the liver (such as, for example, fibrosis caused by a hepatitis B and/or C virus)), scleroderma; solid tumors or cancers such as leukemia (such as, for example, B cell chronic lymphocytic leukaemia), glioblastoma, lymphoma (such as, for example, Hodgkin's lymphoma) and mastocytosis.

In one embodiment, the inflammatory disorder is selected from the group comprising asthma (e.g., allergic asthma), atopic dermatitis, chronic obstructive pulmonary disease (COPD), pulmonary fibrosis, food allergy, nasal polyposis and eosinophilic esophagitis.

In one embodiment, the inflammatory disorder is selected from the group comprising asthma (e.g., allergic asthma), atopic dermatitis, chronic obstructive pulmonary disease (COPD), pulmonary fibrosis and food allergy.

In one embodiment, the inflammatory disorder is allergy, asthma, or atopic dermatitis.

In one embodiment, the inflammatory disorder is allergic asthma.

In one embodiment, the inflammatory disorder is a solid tumor. In one embodiment, the method of the present invention is for preventing metastasis from solid tumor.

The present invention further relates to a method for inducing desensitization of a subject allergic to a specific antigen, wherein said method comprises administering to the subject the immunogenic product, composition, pharmaceutical composition, medicament, or vaccine composition of the invention and said allergen.

As used herein, the term "desensitization", also known as allergen immunotherapy, desensitization or hypo-sensitization or allergy vaccination, refers to a medical treatment for environmental allergies, such as allergic asthma. Such treatment involves exposing people to larger and larger amounts of allergen in an attempt to reduce the immune system's response in presence of allergen.

Examples of allergens include, but are not limited to inhaled allergens, ingested allergens and contact allergens.

Examples of inhaled allergens include, but are not limited to, allergens from Astigmata (e.g., *Acarus siro* (Storage mite, Aca s 13), *Blomia tropicalis* (Mite, Blo t), *Dermatophagoides farinae* (American house dust mite, Der f), *Dermatophagoides microceras* (House dust mite, Der m), *Dermatophagoides pteronyssinus* (European house dust mite, Der p), *Euroglyphus maynei* (House dust mite, Eur m), *Glycyphagus domesticus* (Storage mite, Gly d 2), *Lepidoglyphus destructor* (Storage mite, Lep d), *Tyrophagus putrescentiae* (Storage mite, Tyr p)); Blattaria (e.g., *Blattella germanica* (German cockroach, Bla g), *Periplaneta americana* (American cockroach, Per a)); Coleoptera (e.g., *Harmonia axyridis* (Asian ladybeetle, Har a)), Diptera (e.g., *Aedes aegypti* (Yellow fever mosquito, Aed a), *Chironomus kiiensis* (Midge, Chi k), *Chironomus thummi thummi* (Midge, Chi t), *Forcipomyia taiwana* (Biting midge, For t), *Glossina morsitans* (Savannah Tsetse fly, Glo m), Hemidiptera: *Triatoma protracta* (California kissing bug, Tria p)), Hymenoptera (e.g., *Apis cerana* (Eastern hive bee, Api c), *Apis dorsata* (Giant honeybee, Api d), *Apis mellifera* (Honey bee, Api m), *Bombus pennsylvanicus* (Bumble bee, Bom p), *Bombus terrestris* (Bumble bee, Bom t), *Dolichovespula arenaria* (Yellow hornet, Dol a), *Dolichovespula maculata* (White face hornet, Dol m), *Myrmecia pilosula* (Australian jumper ant, Myr p), *Polistes annularis* (Wasp, Pol a), *Polistes dominulus* (Mediterranean paper wasp, Pol d), *Polistes exclamans* (Wasp, Pol e), *Polistes fuscatus* (Wasp, Pol f), *Polistes gallicus* (Wasp, Pol g), *Polistes metricus* (Wasp, Pol m), *Polybia paulista* (Wasp, Pol p), *Polybia scutellaris* (Wasp, Pol s), *Solenopsis geminata* (Tropical fire ant, Sol g), *Solenopsis invicta* (Red imported fire ant, Sol i), *Solenopsis richteri* (Black fire ant, Sol r), *Solenopsis saevissima* (Brazilian fire ant, Sol s), *Vespa crabro* (European hornet, Vesp c), *Vespa mandarinia* (Giant asian hornet, Vesp m), *Vespula fiavopilosa* (Yellow jacket, Vesp f), *Vespula germanica* (Yellow jacket, Vesp g), *Vespula maculifrons* (Yellow jacket, Vesp m), *Vespula pensylvanica* (Yellow jacket, Vesp p), *Vespula squamosa* (Yellow jacket, Vesp s), *Vespula vidua* (Wasp, Vesp vi), *Vespula vulgaris* (Yellow jacket, Vesp v)), Ixodida (e.g., *Argas reflexus* (Pigeon tick, Arg r)), Lepidoptera (e.g., *Bombyx niori* (Silk moth, Bomb n), *Plodia interpunctella* (Indianmeal moth, Plo i), *Thaumetopoea pityocampa* (Pine processionary moth, Tha p)), Thysanura (e.g., *Lepisma saccharina* (Silverfish, Lep s)), Siphonaptera (e.g., *Ctenocephalides felis felis* (Cat flea, Cte f)), Carnivora (e.g., *Canis familiaris* (dog, Can f), *Felis domesticus* (cat, Fel d)); Lagomorpha (e.g., *Oryctolagus cuniculus* (rabbit, Ory c), Perissodactyla: *Equus caballus* (domestic horse, Equ c)), Pleuronectiformes (e.g., *Lepidorhombus whiffiagonis* (Megrim, Whiff, Gallo, Lep w)), Rodentia (e.g., *Cavia porcellus* (guinea pig, Cav p), *Mus musculus* (mouse, Mus m), *Rattus norvegius* (rat, Rat n)); Coniferales: *Chamaecyparis obtusa* (Japanese cypress, Cha o), *Cupressus arizonica* (Cypress, Cup a), *Cryptomeria japonica* (Sugi, Cry j), *Cupressus sempervirens* (Common cypress, Cup s), *Juniperus ashei* (Mountain cedar, Jun a), *Juniperus oxycedrus* (Prickly juniper, Jun o), *Juniperus sabinoides* (Mountain cedar, Jun s), *Juniperus virginiana* (Eastern red cedar, Jun v)); Gentianales (e.g., *Catharanthus roseus* (Rosy periwinkle, Cat r)); Poales (e.g., *Anthoxanthum odoratum* (Sweet vernal grass, Ant o 1), *Cynodon dactylon* (Bermuda grass, Cyn d 1, Cyn d 7, Cyn d 12, Cyn d 15, Cyn d 22w, Cyn d 23, Cyn d 24), *Dactylis glomerata* (Orchard grass, Dae g 1, Dae g 2, Dae g 3, Dae g 4, Dae g 5), *Festuca pratensis* (Meadow fescue, Fes p 4)), *Holcus lanatus* (Velvet grass, Hol 11, Hol 15), *Hordeum vulgare* (Barley, Hor v 1, Hor v 5, Hor v 12, Hor v 15, Hor v 16, Hor v 17, Hor v 21), *Lolium perenne* (Rye grass, Lol p 1, Lol p 2, Lol p 3, Lol p 4, Lol p 5, Lol p 11), *Oryza sativa* (Rice, Ory s 1, Ory s 12), *Paspalum notarum* (Bahia grass, Pas n 1), *Phalaris aquatica* (Canary grass, Pha a 1, Pha a 5), *Phleum pratense* (Timothy, Phl p 1, Phl p 2, Phl p 4, Phl p 5, Phl p 6, Phl p 7, Phl p 11, Phl p 12, Phl p 13), *Poa pratensis* (Kentucky blue grass, Poa p 1, Poa p 5), *Secale cereale* (Rye, Sec c 1, Sec c 20), *Sorghum halepense* (Johnson grass, Sor h 1), *Triticum aestivum* (Wheat, Tri a 12, Tri a 14, Tri a 185, Tri a 19, Tri a 25, Tri a 26, Tri a 27, Tri a 28, Tri a 29, Tri a 30), *Zea mays* (Maize, Zea m 1, Zea m 12, Zea m 14, Zea m 25), Fagales: *Alnus glutinosa* (Alder, Aln g 1, Aln g 4), *Betula verrucosa* (Birch, Bet v 1, Bet v 2, Bet v 3, Bet v 4, Bet v 5, Bet v 6, Bet v 7), *Carpinus betuhxs* (Hornbeam, Car b 1)); Lamiales (e.g., *Fraxinus excelsior* (Ash, Fra e 1), *Ligustrum vulgare* (Privet, Lig v), *Syringa vulgaris* (Lilac, Syr v)); Malpighiales (e.g., *Hevea brasiliensis* (para rubber tree (latex), Hev b 1, Hev b 2, Hev b 3, Hev b 4, Hev b 5, Hev b 6, Hev b 7, Hev b 8, Hev b 9, Hev b 10, Hev b 11, Hev b 12, Hev b 13)); Proteales (e.g., *Platanus acerifolia* (London plane tree, Pla a 1, Pla a 2, Pla a 3), *Platanus orientalis* (Oriental plane, Pla or 1, Pla or 2, Pla or 3)).

In one embodiment, the inhaled allergen is selected from the group comprising or consisting of *Acarus siro* (Storage mite, Aca s 13), *Dermatophagoides farinae* (American house dust mite, Der f), *Dermatophagoides microceras* (House dust mite, Der m), *Dermatophagoides pteronyssinus* (European house dust mite, Der p), *Euroglyphus maynei* (House dust mite, Eur m), *Glycyphagus domesticus* (Storage mite, Gly d 2), *Polistes annularis* (Wasp, Pol a), *Polistes dominulus* (Mediterranean paper wasp, Pol d), *Polistes exclamans* (Wasp, Pol e), *Polistes fuscatus* (Wasp, Pol f), *Polistes gallicus* (Wasp, Pol g), *Polistes metricus* (Wasp, Pol m), *Polybia paulista* (Wasp, Pol p), *Polybia scutellaris* (Wasp, Pol s), *Felis domesticus* (cat, Fel d), Poales and *Betula verrucosa* (Birch, Bet v 1, Bet v 2, Bet v 3, Bet v 4, Bet v 5, Bet v 6, Bet v 7).

Examples of ingested allergens include, but are not limited to, allergens from Fungi Ascomycota, such as, for example, Dothideales (e.g., *Alternaria alternata* (Alternaria rot fungus, Alt a), *Cladosporium cladosporioides* (Cla c), *Cladosporium herbarum* (Cla h), *Curvularia lunata* (Cur 1), —Eurotiales: *Aspergillus flavus* (Asp fl), *Aspergillus fumigatus* (Asp f), *Aspergillus niger* (Asp n), *Aspergillus oryzae* (Asp o), *Penicillium brevicompactum* (Pen b), *Penicillium chrysogenum* (Pen ch), *Penicillium citrinum* (Pen c), *Penicillium oxalicum* (Pen o)), Hypocreales (e.g., *Fusarium culmorum* (Fus c)); Onygenales (e.g., *Trichophyton rubrum* (Tri r), *Trichophyton tonsurans* (Tri t), Saccharomycesales: *Candida albicans* (Yeast, Cand a), *Candida boidinii* (Yeast, Cand b)); Tuberculariales (e.g., *Epicoccum purpurascens* (Epi p)), allergens from Fungi Basidiomycota, such as, for example, Hymenomycetes (e.g., *Coprinus comatus* (Shaggy mane, Cop c), *Psilocybe cubensis* (Magic mushroom, Psi c), Urediniomycetes (e.g., *Rhodotorula mucilaginosa* (Yeast, Rho m)); Ustilaginomycetes (e.g., *Malassezia furfur* (Pityriasis versicolor infect. Agent, Mala f), *Malassezia sympodialis* (Mala s)); antibiotics (such as, for example, Penicillins, Cephalosporins, Aminosides, Quinolones, Macrolides, Tetracycline, Sulfamids); drugs (such as, for example, acetylsalicylic acid, vaccines, morphines and derivatives); vitamins such as, for example, vitamin K1; and food allergens (such as, for example, allergen from milk, egg, peanut, tree nut (walnut, cashew, etc.), fish, shellfish, soy, wheat, and carrot, apple, pear, avocado, apricot, peach).

In one embodiment, the ingested allergen is a food allergen.

In one embodiment, the food allergen is selected from the group comprising or consisting of allergen from milk, egg, peanut, tree nut (walnut, cashew, etc.), fish, shellfish, soy, wheat, and carrot, apple, pear, avocado, apricot, peach.

Examples of contact allergens include, but are not limited to, heavy metals (such as, for example, nickel, chrome, gold), latex, haptens such as, for example halothane, hydralazine.

In one embodiment, the allergen is selected from the group comprising or consisting of *Acarus siro* (Storage mite, Aca s 13), *Dermatophagoides farinae* (American house dust mite, Der f), *Dermatophagoides microceras* (House dust mite, Der m), *Dermatophagoides pteronyssinus* (European house dust mite, Der p), *Euroglyphus maynei* (House dust mite, Eur m), *Glycyphagus domesticus* (Storage mite, Gly d 2), *Polistes annularis* (Wasp, Pol a), *Polistes dominulus* (Mediterranean paper wasp, Pol d), *Polistes exclamans*

(Wasp, Pol e), *Polistes fuscatus* (Wasp, Pol f), *Polistes gallicus* (Wasp, Pol g), *Polistes metricus* (Wasp, Pol m), *Polybia paulista* (Wasp, Pol p), *Polybia scutellaris* (Wasp, Pol s), *Felis domesticus* (cat, Fel d), Poales and *Betula verrucosa* (Birch, Bet v 1, Bet v 2, Bet v 3, Bet v 4, Bet v 5, Bet v 6, Bet v 7) and food allergens.

The present invention also further relates to a method for increasing the efficacy and/or for decreasing the duration of a desensitization of a subject allergic to a specific allergen, wherein said subject is treated by desensitization, and is further administered with the immunogenic product, composition, pharmaceutical composition, medicament, or vaccine composition of the invention.

In one embodiment, in the methods of the present invention, the subject is administered first with the immunogenic product, composition, pharmaceutical composition, medicament, or vaccine composition of the invention, and second with the allergen.

In one embodiment, in the methods of the present invention, the subject is administered first with the allergen, and second with the immunogenic product, composition, pharmaceutical composition, medicament, or vaccine composition of the invention.

In another embodiment, in the method of the present invention, the subject receives a combined administration of the immunogenic product, composition, pharmaceutical composition, medicament, or vaccine composition of the invention, and of the allergen.

The present invention further relates to a composition, pharmaceutical composition, medicament or vaccine as described hereinabove, wherein said composition, pharmaceutical composition, medicament or vaccine further comprises at least one allergen.

In one embodiment, a therapeutically effective amount of at least one immunogenic product of the invention is administered or is to be administered to the subject. In one embodiment, the therapeutically effective amount corresponds to an amount of total proteins determined using a Bradford protein assay as well known in the art.

In one embodiment, the amount of the immunogenic product to be administered to the subject induces an immunoprotective response without significant adverse effects.

In one embodiment, the amount of the immunogenic product to be administered to the subject induces an allergen desensitization without significant adverse effects.

Optimal amounts of components for the immunogenic product of the invention can be ascertained by standard studies involving observation of appropriate immune responses in subjects. Following an initial vaccination, subjects can receive one or several booster immunizations adequately spaced.

In one embodiment, the treatment consists of a single dose or a plurality of doses over a period of time.

In one embodiment of the invention, the subject to be treated is administrated at least twice in a month with the therapeutically effective amount of immunogenic product as described here above.

In another embodiment of the invention, the subject to be treated is administrated twice in 1 month with a therapeutically effective amount of the immunogenic product of the invention. In this embodiment, the subject may be administrated once at day 0 and the second time between day 7 and day 28. In one embodiment, the subject is administrated once at day 0 and the second time at day 28.

In another embodiment of the invention, the subject to be treated is administrated three times in 1 month with a therapeutically effective amount of the immunogenic product of the invention. In this embodiment, the subject to be treated may be administrated once at day 0, the second time between day 7 and day 14 and the third time between day 21 and day 28. In one embodiment, the subject is administrated once at day 0, the second time at day 7 and the third time at day 28.

In another embodiment of the invention, the subject to be treated may be further administrated once every three months with the therapeutically effective amount of the immunogenic product of the invention.

In one embodiment of the invention, the subject to be treated is administrated three times in one month as described here above, and then further administered once every three months with the therapeutically effective amount of the immunogenic product of the invention.

In another embodiment of the invention, the subject to be treated may be further administrated with a therapeutically effective amount of the immunogenic product as described here above when the amount of antibodies against IL-4 is undetectable in a serum sample obtained from the subject.

In another embodiment of the invention, the subject to be treated may be further administrated with a therapeutically effective amount of the immunogenic product as described here above when the amount of antibodies against IL-13 is undetectable in a serum sample obtained from the subject.

In another embodiment of the invention, the subject to be treated may be further administrated with a therapeutically effective amount of the immunogenic product as described here above when the amount of antibodies against IL-4 and IL-13 are undetectable in a serum sample obtained from the subject.

EXAMPLES

The present invention is further illustrated by the following examples.

The present invention relates to an immunogenic product using $CRM_{197}$ as a carrier protein. The properties of the immunogenic product of the invention are illustrated by the following examples. In addition, the product of the invention was compared to immunogenic product made with KLH to distinguish the present invention from previous art and to show its superiority to previous art.

$CRM_{197}$ is a non-toxic form of diphtheria toxin without toxic activity due to a single base substitution, in its toxin domain, from glycine to glutamate in position 52 (Uchida et al. 1973 J Biol Chem). As an alternative, Keyhole Limpet Hemocyanin (KLH), a copper-containing protein that is found in arthropods and mollusca (Swaminathan et al. 2014), was also tested and compared to $CRM_{197}$.

The immunogenic products of the invention were produced using the manufacturing process developed below.

Figure 1:
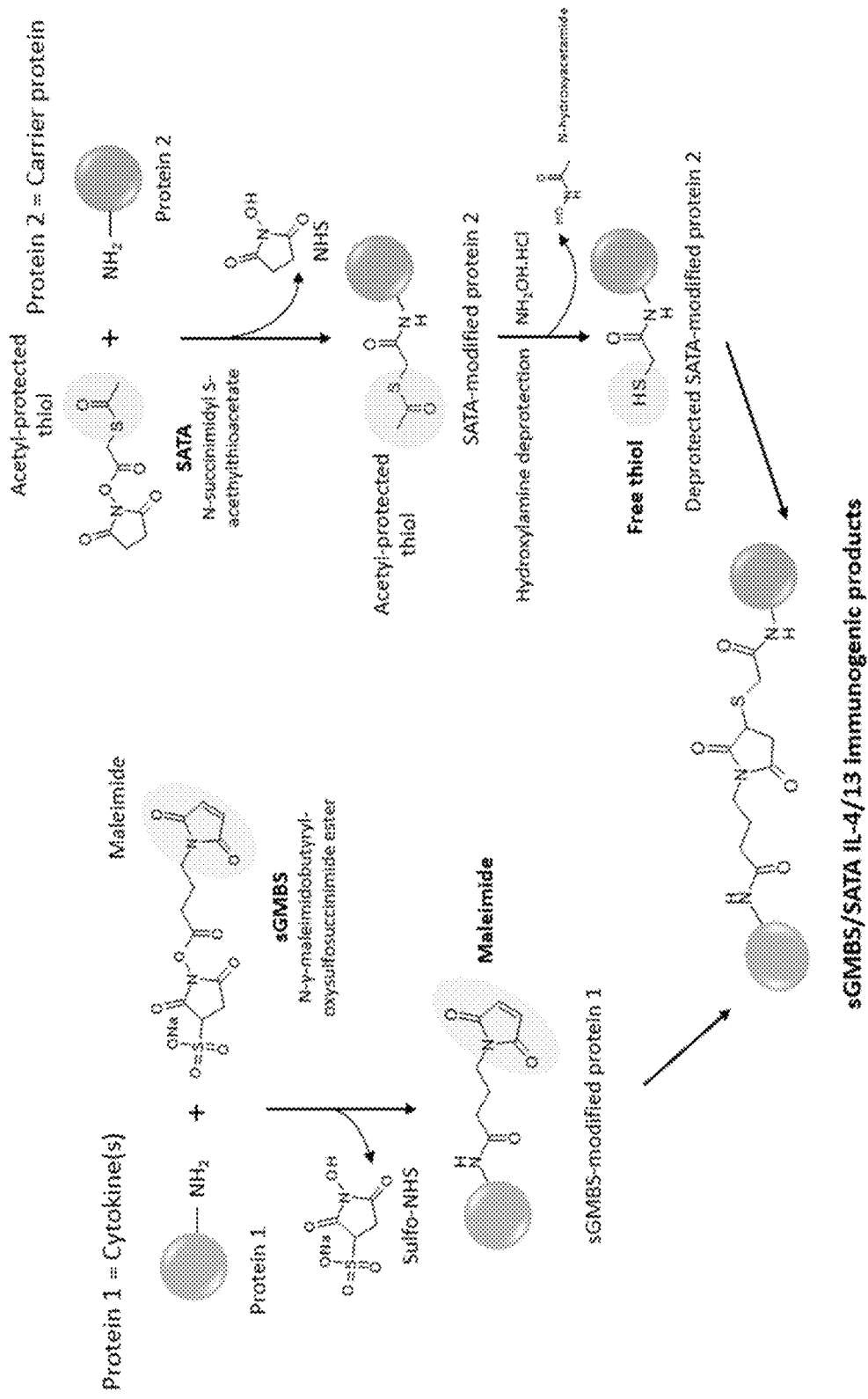
FIG. 1 is a scheme of the chemical conjugation of sGMBS-modified IL-4 or IL-13 and SATA-labeled carrier protein through thiol-maleimide addition for the manufacturing of the immunogenic products of the present invention.

A thiol-maleimide conjugation is employed for the preparation of IL-4 and IL-13 immunogenic products. Sulfhydryl moieties were introduced on the carrier protein $CRM_{197}$ with SATA and subsequent hydroxylamine deprotection, while the cytokine muIL-4 or muIL-13 were derivatized by sGMBS, a maleimide-containing agent. Both SATA and sGMBS are heterobifunctional crosslinkers containing a NHS-ester, which reacts with primary amines (such as ε-amino groups of lysine residues and protein N-termini). An overview of the immunogenic product synthesis via thiol-maleimide conjugation is provided in FIG. 1.

Example 1: Preparation of the Murine IL-4 and IL-13 Immunogenic Products of the Invention with the Two Carrier Proteins a) Carrier Protein Functionalization $CRM_{197}$ or KLH was diluted in the modification buffer comprising 70 mM sodium phosphate buffer, 150 mM NaCl, 5 mM EDTA (pH 7.2). SATA was diluted in DMSO to reach a 100 mM concentration. Then, SATA was added to $CRM_{197}$ or KLH and after 30 minutes of incubation on a nutator at room temperature, SATA in excess was removed using Zeba™ desalting spin column, according to the manufacturer's instructions.

Subsequently, hydroxylamine was diluted in the same buffer at 500 mM. Then, $CRM_{197}$-SATA or KLH-SATA was incubated with the hydroxylamine solution at a 50 mM final concentration, during 2 hours on a nutator at room temperature. Finally, the mixture was desalted and reagents in excess were removed using Zeba™ desalting spin column.

b) muIL-4 and muIL-13 Functionalization muIL-4 or muIL-13 was dissolved in modification buffer (70 mM sodium phosphate buffer, 150 mM NaCl, 5 mM EDTA, pH 7.2). sGMBS was diluted in modification buffer at 10 mM. Then, sGMBS was added to muIL-4 or muIL-13 and after one hour of incubation on a nutator at room temperature, sGMBS in excess was removed using Zeba™ desalting spin column.

c) Conjugation

After $CRM_{197}$, KLH, muIL-4 and muIL-13 functionalization, protein contents of each preparation were determined by Bradford assay.

Functionalized $CRM_{197}$ or functionalized KLH was added to functionalized muIL-4 or functionalized muIL-13 at a molar ratio of 1:2 (carrier: muIL-4 or carrier: muIL-13) and 1:20 respectively. The ratio 1:20 for KLH was chosen based on the difference of molecular weight between KLH and $CRM_{197}$ ($CRM_{197} \sim 58$ kDa vs KLH subunit used in this manufacturing $\sim 400$ kDa) and based on previous experience in making IFN immunogenic product, a vaccine currently evaluated in a phase IIb clinical trial in lupus patients (NCT02665364) allowing to mix similar quantity of cytokine and carrier in all manufacturings.

Individual immunogenic product preparations were incubated overnight at 4° C., on a nutator. The resulting immunogenic products were then concentrated using Amicon (3 kDa-cut-off membrane), 0.22 μm-filtered and kept at 4° C.

d) Control (Unconjugated Cytokines and $CRM_{197}$)

As controls, two mixtures (called unconjugated cytokines and $CRM_{197}$) were prepared without proteins functionalization:

muIL-4 and $CRM_{197}$ were mixed at a molar ratio of 1:2 ($CRM_{197}$:cytokine). The mix was prepared at 700 μg/mL, without using any coupling reagent.

muIL-13 and $CRM_{197}$ were mixed at a molar ratio of 1:2 ($CRM_{197}$:cytokine). The mix was prepared at 700 μg/mL, without using any coupling reagent.

Both mixtures were 0.22 μm-filtered and stored at 4° C.

e) Immunogenic Product Quantifications

Concentrations of muIL-4 immunogenic product and muIL-13 immunogenic product were determined by Coomassie Plus (Bradford) Protein Assay according to the manufacturer instructions.

Example 2: Antigenicity of the Murine Products

A sandwich ELISA was performed to evaluate the cytokine coupling to the carrier protein and also to evaluate whether epitopes are preserved during the manufacturing process.

Figure 2:
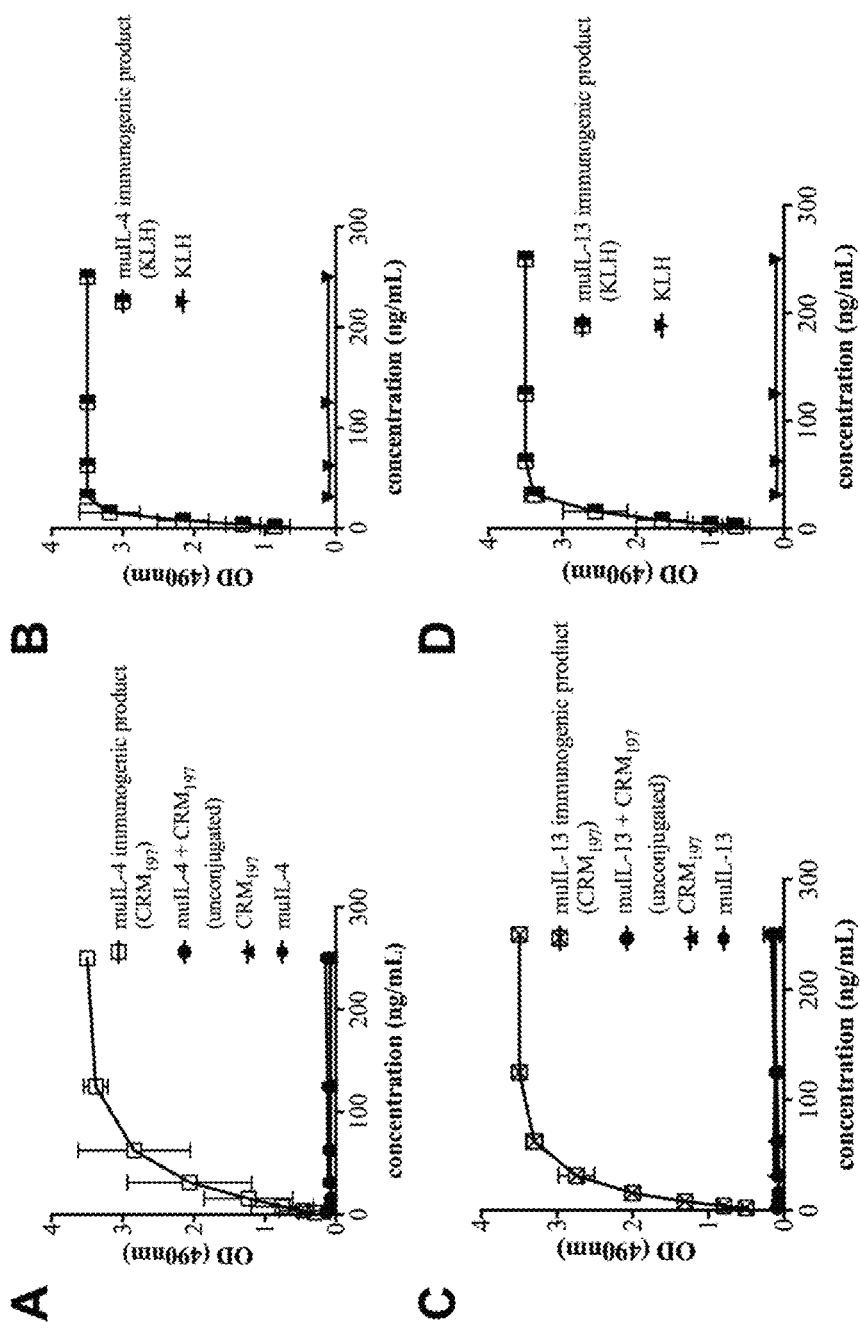
FIG. 2 is a combination of graphs showing the antigenicity of muIL-4 and muIL-13 immunogenic products. Capture was performed with anti-$CRM_{197}$ antibody (A, C) or anti-KLH antibody (B, D) and detection with biotinylated polyclonal anti-muIL-4 antibody (A, B) or biotinylated polyclonal anti-muIL-13 antibody (C, D). Represented OD values are OD means of duplicates.

Briefly, capture antibody (anti-carrier protein antibody) was coated in 96-well plates. After a blocking step with 2% (w/v) casein in PBS, immunogenic product samples were added and 2-fold serially diluted. After 90 minutes of incubation at 37° C., bound immunogenic products were detected using biotinylated anti-muIL-4 antibody (polyclonal goat IgG anti-muIL-4) or biotinylated anti-muIL-13 antibody (polyclonal goat IgG anti-muIL-13) and then revealed with streptavidin-HRP and OPD substrate. The enzymatic reaction was stopped with sulfuric acid and optical density (OD) was read at 490 nm. Results are shown in FIG. 2.

This test confirmed that the immunogenic products of the invention comprises muIL-4 or muIL-13 coupled to $CRM_{197}$ or KLH. Furthermore, these results confirm that the immunogenic products are antigenic (i.e. recognized by anti-muIL-4 or anti-muIL-13 antibodies).

Example 3: Immunogenicity of the Immunogenic Products

Immunogenic products were administered in mice as an emulsion with a squalene-based adjuvant. Immunogenic products were diluted with PBS to the desired concentration and dilutions were mixed with an equal volume of adjuvant.

Mice Immunization Protocol

Each Balb/c mouse received four intramuscular (i.m.) injections of immunogenic products (with $CRM_{197}$ or KLH) or controls such as PBS, the unconjugated cytokines with $CRM_{197}$ or $CRM_{197}$ alone, all emulsified (1:1) with a squalene-based adjuvant. Injections were performed on days 0, 7, 28 and 49 as detailed in Table 1 and FIG. 3. First immunization was performed at 7 weeks of age.

TABLE 1

Dose schedule of administrations

| Article | Number of mice per group | Day | Dose/ injection (μg) | Adjuvant |
| --- | --- | --- | --- | --- |
| muIL-4 immunogenic product ($CRM_{197}$) | 10 | 0/7/28/49 | 30/30/10/10 | Squalene oil-in-water adjuvant |
| muIL-4 immunogenic product (KLH) | 10 | 0/7/28/49 | 30/30/10/10 | |
| muIL-13 immunogenic product ($CRM_{197}$) | 10 | 0/7/28/49 | 30/30/10/10 | |
| muIL-13 immunogenic product (KLH) | 10 | 0/7/28/49 | 30/30/10/10 | |
| Unconjugated muIL-4 + $CRM_{197}$ | 5 | 0/7/28/49 | 30/30/10/10 | |
| Unconjugated muIL-13 + $CRM_{197}$ | 5 | 0/7/28/49 | 30/30/10/10 | |
| $CRM_{197}$ | 5 | 0/7/28/49 | 30/30/10/10 | |
| DPBS | 5 | 0/7/28/49 | — | |

Blood collections were performed before dosing and at days 39, 60 and 120. Serum samples were prepared after coagulation at room temperature and centrifugation to remove the clot. Mice were sacrificed by lethal anesthesia at day 120.

Determination of Anti-Cytokines and Anti-Carrier Proteins Antibodies Titers by ELISA Serum samples of immunized mice were assessed for the presence of anti-cytokines antibodies and anti-carrier protein antibodies by ELISA.

Briefly, muIL-4, muIL-13, $CRM_{197}$ or KLH were coated in 96-well plates. After blocking with casein, serum samples were added, and two-fold serially diluted. After incubation at 37° C., bound antibodies were detected with HRP-conjugated anti-mouse IgG and plates were revealed using OPD substrate. The reaction was stopped with sulfuric acid and absorbance at 490 nm was recorded.

Positive controls used for anti-muIL-4 antibody, anti-muIL-13 antibody, anti-KLH antibody and anti-$CRM_{197}$ antibody titers were respectively, the rat monoclonal anti-muIL-4 IgG1 antibody, the mouse monoclonal anti-muIL13 antibody, pool of sera collected from mice immunized with KLH and the anti-diphtheria toxin A mouse monoclonal IgG1.

Samples were analyzed starting at dilution 500 $dil^{-1}$ up to 256,000 $dil^{-1}$, except for pre-immune sera analyzed only at 500 $dil^{-1}$.

Anti-muIL-4, anti-muIL-13, anti-$CRM_{197}$ and anti-KLH titers were expressed as serum dilutions leading to half maximal OD.

Figure 4:
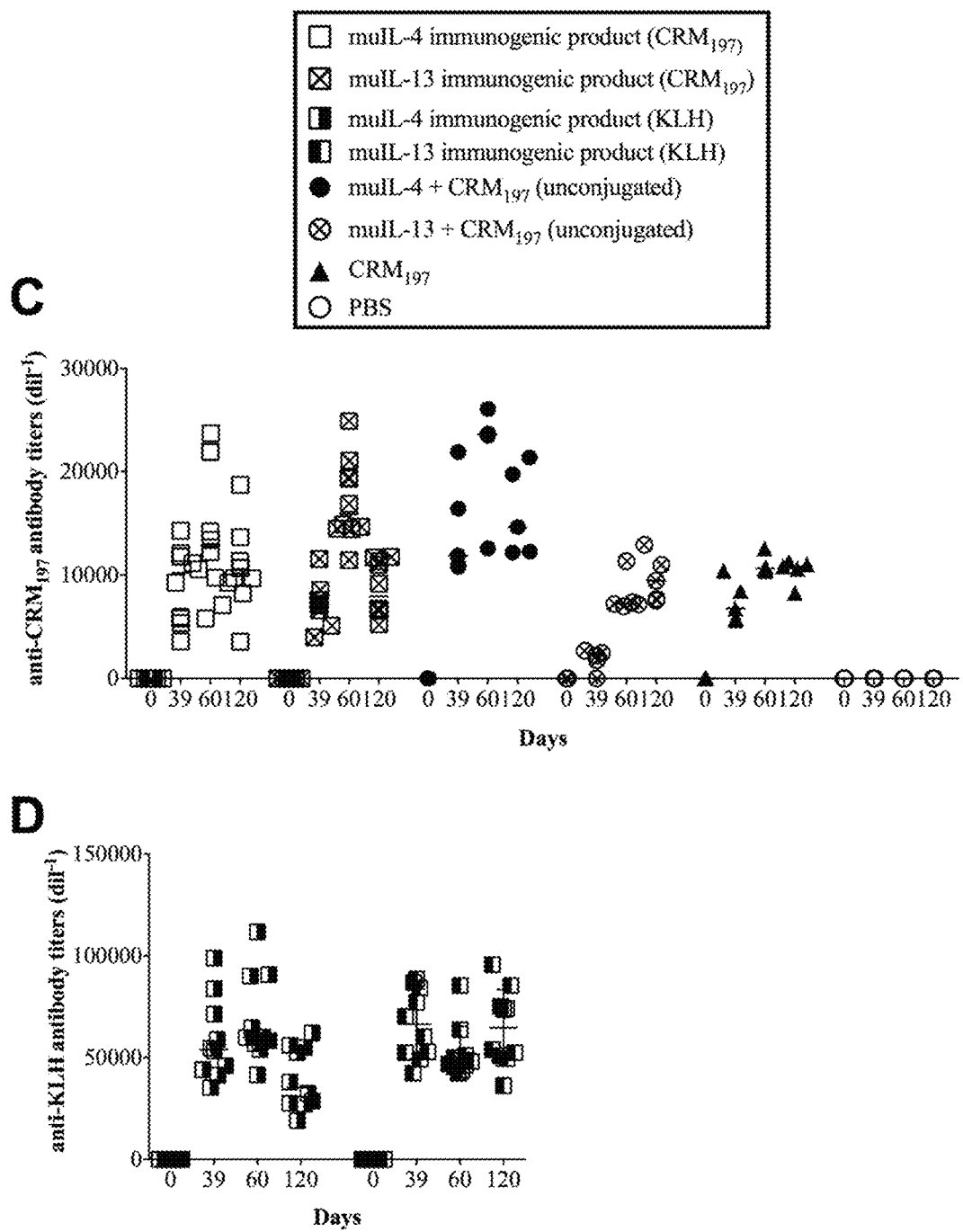
FIG. 4 is a combination of graphs showing anti-muIL-4 (A), anti muIL-13 (B), anti-$CRM_{197}$ (C) and anti-KLH (D) antibody titers in mice sera. Ten mice per group were used in immunogenic products groups and 5 mice in control groups. Bars represent median.

Results are presented in FIG. 4. In all groups treated with immunogenic products as well as for mice injected with adjuvanted DPBS or carrier protein or unconjugated preparations, no anti-muIL-4, no anti-muIL-13 no anti-KLH and no anti-$CRM_{197}$ were detected before dosing.

In addition, no anti-cytokine or anti-carrier antibodies were detected at any timepoint in mice receiving adjuvanted DPBS.

Anti-$CRM_{197}$ titers were detected in all groups treated with $CRM_{197}$ control at days 39, 60 and 120 as well as in group treated with unconjugated muIL-4+$CRM_{197}$ or with unconjugated muIL-13+$CRM_{197}$. Anti-muIL-4, anti-muIL-13 and anti-$CRM_{197}$ titers were detected in all groups treated with the immunogenic products made with $CRM_{197}$ at days 39, 60 and 120. Anti-muIL-4, anti-muIL-13 and anti-KLH titers were detected but not in all mice in all groups treated with immunogenic products made with KLH at days 39, 60 and 120. Of note, the level of anti-IL-4 antibodies were higher in mice immunized with immunogenic products made with $CRM_{197}$ than with the immunogenic products made with KLH.

potential neutralizing muIL-4 antibodies induced after immunogenic products injections will prevent CTLL-2 growth.

Serum samples were added at 1/200 final and positive control polyclonal anti-muIL-4 antibody at 1 µg/mL final, and were 2-fold serially diluted in 25 µL per well RPMI+ 10% (v/v) FBS in culture plates. muIL-4 was then added at 2 ng/mL final to serum samples and incubated for 1 hour at room temperature. Then 20,000 CTLL-2 cells were added to pre-incubated samples (serum or positive control plus muIL-4). Plates were incubated for 48 h at 37° ° C., 5% $CO_2$ in a humidified incubator. Cell viability was quantified by MTS/PMS assay. Forty microliters per well of MTS/PMS were added and after 4 h at 37° C., 5% $CO_2$ in a humidified incubator, OD was read at 490 nm.

$NC_{50}$ results were expressed as the serum dilution factor ($dil^{-1}$) neutralizing 50% of muIL-4 activity in presence of serum. The $NC_{50}$ is determined by interpolating the serum dilution resulting in a 50% of IL-4 activity on the abscissa axis. Of note, a mouse is considered as a responder in this experiment if $NC_{50} \geq 200$ $dil^{-1}$.

Figure 5:
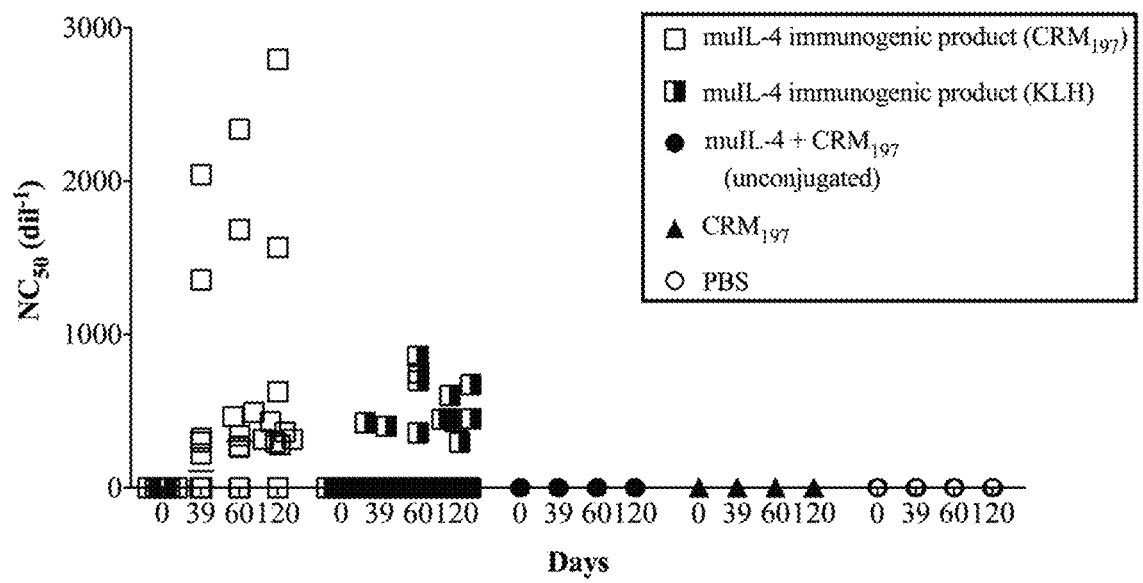
FIG. 5 is a graph showing the muIL-4 neutralizing capacities in mice sera. Ten mice per group were used in immunogenic products groups and 5 mice in control groups. Bars represent median.

None of the mouse exhibited anti-muIL-4 neutralizing antibodies before dosing (FIG. 5 and Table 2). In the control groups, no anti-muIL-4 antibodies having a neutralizing capacity were detected at any time point. For mice immunized with immunogenic product made with $CRM_{197}$, antibodies with neutralizing capacities against muIL-4 were detectable in 9 out of 10 mice. In contrast, in mice immunized with the immunogenic product made with KLH the level of anti-IL-4 neutralizing antibodies were lower at any time point than the one observed when $CRM_{197}$ was the carrier and fewer sera exhibited neutralizing antibodies (at best time point only 6 sera exhibited neutralizing capacity (at day 120)). These results demonstrated that treatment with muIL-4 immunogenic product made with $CRM_{197}$ was more immunogenic than the conjugated vaccine made with KLH.

TABLE 2

| | $NC_{50}$ responders towards IL-4 | | | | | | | | | | | |
|---|---|---|---|---|---|---|---|---|---|---|---|---|
| | muIL-4 immunogenic product ($CRM_{197}$) | | | | muIL-4 immunogenic product (KLH) | | | | muIL-4 + $CRM_{197}$ (unconjugated) | | | |
| | D0 | D39 | D60 | D120 | D0 | D39 | D60 | D120 | D0 | D39 | D60 | D120 |
| Responders (NC50 > 200 dil-1) | 0/10 | 5/10 | 7/10 | 9/10 | 0/10 | 2/10 | 4/10 | 6/10 | 0/5 | 0/5 | 0/5 | 0/5 |

| | $CRM_{197}$ | | | | PBS | | | |
|---|---|---|---|---|---|---|---|---|
| | D0 | D39 | D60 | D120 | D0 | D39 | D60 | D120 |
| Responders (NC50 > 200 dil-1) | 0/5 | 0/5 | 0/5 | 0/5 | 0/5 | 0/5 | 0/5 | 0/5 | muIL-4 Neutralization Bioassay

The antibodies induced by administrations of muIL-4 immunogenic products were further assessed for their anti-muIL-4 neutralizing capacities in a proliferative assay using CTLL-2 cells adapted from Soman et al, 2009. Briefly, CTLL-2 cells were grown in presence of IL-2 at 10 ng/mL final with RPMI supplemented with 2 mM glutamine, 1 mM sodium pyruvate, 1 mM HEPES, 100 units/mL penicillin, 100 µg/mL streptomycin and 10% (v/v) FBS. For neutralization bioassays, IL-2 was replaced by muIL-4. Therefore, muIL-13 Neutralization Bioassay Antibodies induced by administrations of muIL-13 immunogenic product were assessed for their neutralizing capacities by muIL-13 neutralization bioassay before dosing and at days 39, 60 and 120.

The neutralizing capacities of anti-muIL-13 antibodies were evaluated using a HEK-Blue™ IL-4/IL-13 reporter gene bioassay (InvivoGen #hkb-il413) by monitoring the activation of the STAT6 pathway. In response to this activation, this cell line produces secreted embryonic alkaline phosphatase (SEAP) which can be quantified using QUANTI-Blue™ (at λ=625 nm). Therefore, potential neutralizing muIL-13 antibodies induced after immunogenic products injections will prevent STAT6 pathway activation and can be evaluated.

Briefly, HEK-Blue™ IL-4/IL-13 cells were plated in an assay medium composed of DMEM GlutaMAX™ supplemented with 10% (v/v) FBS, 10 mM HEPES, 50 U/mL penicillin and 50 μg/mL streptomycin. Then a mix of muIL-13 (at 2 ng/mL final concentration) and two-fold serially diluted serum sample starting at 1/100 final or control antibody two fold serially diluted from 1 μg/mL final (polyclonal goat anti-muIL-13 antibody) were added to 40,000 HEK-Blue™ IL-4/IL-13 cells. Plates were incubated 24 h at 37° C., in a 5% $CO_2$ humidified incubator. Then, in new flat-bottom plates, 10 μL per well of cell supernatant were added to 90 μL per well of QUANTI-Blue™ and after 1 h at 37° C., in a 5% $CO_2$ humidified incubator, absorbances were read at 625 nm.

$NC_{50}$ results were expressed as the serum dilution factor ($dil^{-1}$) neutralizing 50% of muIL-13 activity in presence of serum. The $NC_{50}$ is determined by interpolating the serum dilution resulting in a 50% of muIL-13 activity on the abscissa axis. Of note, a mouse is considered as a responder in this experiment if $NC_{50} \geq 100$ $dil^{-1}$.

Figure 6:
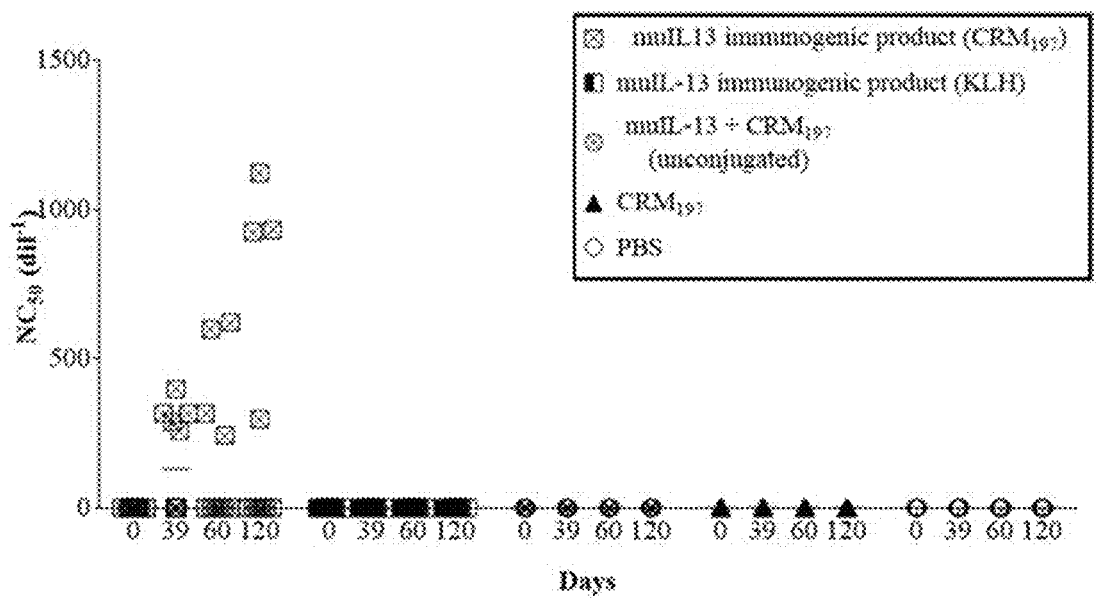
FIG. 6 is a graph showing muIL-13 neutralizing capacities in mice sera. Ten mice per group were used in immunogenic products groups and 5 mice in control groups. Bars represent median.

No muIL-13 neutralizing antibodies were detected before dosing in all groups as well as in control groups at any time point (FIG. 6 and Table 3). Mice treated with the immunogenic product made with $CRM_{197}$ produced antibodies with detectable neutralizing capacities against muIL-13 (FIG. 6 and Table 3). In mice immunized with immunogenic product made with KLH, no mice sera exhibited neutralizing antibodies against muIL-13. Of note, even if one mouse exhibited anti-muIL-13 antibodies as assessed by ELISA in the unconjugated muIL-13 and $CRM_{197}$ group (FIG. 4-B), these antibodies were not neutralizing antibodies. These results demonstrated that treatment with the immunogenic product made with $CRM_{197}$ is more immunogenic than the one made with KLH.

As expected, no neutralizing anti-muIL-4 and anti-muIL-13 antibodies were detected in the $CRM_{197}$ and DPBS control groups at any time point. In the control groups where the cytokines and $CRM_{197}$ were mixed without chemical functionalization (unconjugated), immunization did not elicit anti-muIL-4 and anti-muIL-13 neutralizing antibodies, highlighting that conjugation between cytokine and carrier protein is mandatory to break B cell self-tolerance against cytokines. Moreover, for mice immunized with the immunogenic product made with KLH no anti-IL-13 neutralizing antibodies was observed while for mice immunized with immunogenic product made with $CRM_{197}$, antibodies with neutralizing capacities against muIL-13 were detectable in 5 out of 10 mice. These results demonstrated that treatment with muIL-13 immunogenic product made with $CRM_{197}$ was more immunogenic than the conjugated vaccine made with KLH.

Example 4: Residual Activities of Immunogenic Products

Residual Activity of muIL-4 Immunogenic Products

The residual activities of muIL-4 immunogenic products were assessed as described below (adapted from Soman et al, 2009).

Briefly, CTLL-2 cells are grown with IL-2. Culture medium was constituted of RPMIc medium supplemented with IL-2 at 10 ng/ml final and 10% (v/v) FBS.

For residual activity bioassays, IL-2 was replaced by muIL-4. Immunogenic products (with $CRM_{197}$ or KLH) of the invention and muIL-4 control were two-fold serially diluted in RPMI+10% (v/v) FBS in 96-well plates beginning at 1000 ng/mL until 4 ng/mL for immunogenic products and 10 ng/mL until 0.04 ng/mL final for muIL-4. As a positive control, six wells with muIL-4 at 10 ng/mL were added and used as the maximum cell proliferation control. These samples are added to 20,000 CTLL-2 cells per well and plates were incubated for 48 h at 37° ° C., 5% $CO_2$ in a humidified incubator. Cell proliferation was quantified by MTS/PMS assay. Forty microliters per well of MTS/PMS were added and after 4 h at 37° C., 5% $CO_2$ in a humidified incubator, plates were read at 490 nm.

The effective dose 50 ($ED_{50}$) value corresponds to the amount of immunogenic product or cytokine resulting in 50% of maximum cell signal. The value is determined by interpolating the 50% of maximum cell signal onto the

TABLE 3

| | \multicolumn{4}{c|}{$NC_{50}$ responders towards IL-13} | | | | | | | |
|---|---|---|---|---|---|---|---|---|---|---|---|---|
| | \multicolumn{4}{c|}{muIL-13 immunogenic product ($CRM_{197}$)} | \multicolumn{4}{c|}{muIL-13 immunogenic product (KLH)} | \multicolumn{4}{c|}{muIL-13 + $CRM_{197}$ (unconjugated)} |
| | D0 | D39 | D60 | D120 | D0 | D39 | D60 | D120 | D0 | D39 | D60 | D120 |
| Responders (NC50 > 100 dil-1) | 0/10 | 5/10 | 4/10 | 5/10 | 0/10 | 0/10 | 0/10 | 0/10 | 0/5 | 0/5 | 0/5 | 0/5 |

| | \multicolumn{4}{c|}{$CRM_{197}$} | \multicolumn{4}{c|}{PBS} |
|---|---|---|---|---|---|---|---|---|
| | D0 | D39 | D60 | D120 | D0 | D39 | D60 | D120 |
| Responders (NC50 > 100 dil-1) | 0/5 | 0/5 | 0/5 | 0/5 | 0/5 | 0/5 | 0/5 | 0/5 | abscissa axis using the y=ax+b formula from the curve passing by the dilution points surrounding the 50% inflexion point.

The inactivation factor was calculated by dividing the $ED_{50}$ of the tested immunogenic product by the mean $ED_{50}$ of the muIL-4 control standard curves.

TABLE 4

$ED_{50}$ and inactivation factors

| Articles | $ED_{50}$ [ng · mL$^{-1}$] | muIL-4 control $ED_{50}$ [ng · mL$^{-1}$] | Inactivation factor |
|---|---|---|---|
| muIL-4 immunogenic product (CRM$_{197}$) | 620.3 | 1.67 | 370 |
| muIL-4 immunogenic product (KLH) | 21.5 | 1.03 | 21 |

As shown in Table 4, muIL-4 residual activity was more reduced in immunogenic product made with CRM$_{197}$ compared to the one prepared with KLH (much higher inactivation factor for muIL-4 immunogenic product prepared with $CRM_{197}$).

Residual Activity of muIL-13 Immunogenic Products

The residual activity of muIL-13 immunogenic products was monitored using HEK-Blue™ IL-4/IL-13 reporter cell line as described below.

Briefly, muIL-13 immunogenic products and muIL-13 control were two-fold serially diluted in assay medium (DMEM, 10% (v/v) FBS, 10 mM HEPES buffer, 50 U/mL penicillin, 50 μg/mL streptomycin) in round bottom plates beginning at 250 ng/mL and 10 ng/ml final, respectively. These mixes were added to 40,000 HEK-Blue™ IL-4/IL-13 cells per well. Plates were incubated 24 h at 37° ° C., in a 5% $CO_2$ humidified incubator. Then, in new flat bottom plates, 10 μL per well of culture supernatant were added to 90 μL per well of QUANTI-Blue™ and after 1 h at 37° ° C., in a 5% $CO_2$ humidified incubator, ODs were read at 625 nm.

The effective dose 50 ($ED_{50}$) value, corresponding to the amount of the immunogenic product (or IL-13) resulting in 50% of maximum signal recorded for the considered samples, is determined by interpolating the ODmax/2 values to the corresponding sample concentrations using a four parameter logistic (4PL) nonlinear regression from the whole dilution points.

The inactivation factors were calculated by dividing the $ED_{50}$ of the muIL-13 immunogenic products by the corresponding $ED_{50}$ of the muIL-13 control standard curves.

TABLE 5

| $ED_{50}$ and inactivation factors | | | |
|---|---|---|---|
| Articles | $ED_{50}$ [ng · mL$^{-1}$] | muIL-13 control $ED_{50}$ [ng · mL$^{-1}$] | Inactivation factor |
| muIL-13 immunogenic product ($CRM_{197}$) | 737 | 0.31 | 2369 |
| muIL-13 immunogenic product (KLH) | 297 | 0.41 | 723 |

As shown in Table 5, muIL-13 residual activity was more reduced in immunogenic product made with $CRM_{197}$ compared to the one prepared with KLH (much higher inactivation factor for muIL-13 immunogenic product prepared with $CRM_{197}$).

Intensity of the immune response against anti-IL-4 and anti-IL-13 was higher when the immunogenic product was made with $CRM_{197}$ compared the one made with KLH as a carrier. In addition, cytokines residual activities were more reduced in immunogenic product made with $CRM_{197}$ compared to those prepared with KLH. From these results, we decided to perform a proof of concept with the products of the invention made with $CRM_{197}$ as a carrier protein. In addition, in allergy, both IL-4 and IL-13 are involved, so we decided to introduce a group of mice that would receive an immunogenic product comprising both IL-4 and IL-13 conjugates with $CRM_{197}$. From now on, all the immunogenic products will be manufactured with $CRM_{197}$ as a carrier protein and their mixture will refer to Combo immunogenic product.

Example 5: Efficacy of the Immunogenic Product of the Invention in an Allergy Mouse Model Among all allergies, allergic asthma and food allergy are major public health problems now each affecting more than 300 million people worldwide. Allergies are considered to result from a breakdown of tolerance, resulting in type 2 immune responses characterized by the production of TH2 cytokines such as IL-4 and IL-13, high levels of IgE antibodies, and infiltration and expansion of immune cells (in particular mast cells, basophils, eosinophils and T cells) within the inflamed tissue.

House dust mite (HDM) is a major source of allergen that affects more than 50% of allergic patients (Meyer et al. 1994). In mice, repeated intranasal challenges with HDM reproduced key features of human chronic asthma including airway hyperresponsiveness (AHR), airflow obstruction, airway wall remodeling, mucus production and inflammatory responses in the lungs characterized by high levels of eosinophils.

Preparation of muIL-4/IL-13 Immunogenic Products a) $CRM_{197}$ Functionalization $CRM_{197}$ was diluted in the modification buffer comprising 70 mM sodium phosphate buffer, 150 mM NaCl, 5 mM EDTA (pH 7.2). SATA was diluted in DMSO to reach a 100 mM concentration. Then, SATA was added to $CRM_{197}$ and after 30 minutes of incubation on a nutator at room temperature, SATA in excess was removed using Zeba™ desalting spin column, according to the manufacturer's instructions.

Subsequently, hydroxylamine was diluted in the same buffer at 500 mM. Then, $CRM_{197}$-SATA was incubated with the hydroxylamine solution at a 50 mM final concentration, during 2 hours on a nutator at room temperature. Finally, the mixture was desalted and reagents in excess were removed using Zeba™ desalting spin column.

b) muIL-4 and muIL-13 Functionalization muIL-4 was dissolved in modification buffer (70 mM sodium phosphate buffer, 150 mM NaCl, 5 mM EDTA, pH 7.2). sGMBS was diluted in modification buffer at 10 mM. Then, sGMBS was added to muIL-4 and after one hour of incubation on a nutator at room temperature, sGMBS in excess was removed using Zeba™ desalting spin column.

muIL-13 was dissolved in modification buffer (70 mM sodium phosphate buffer, 150 mM NaCl, 5 mM EDTA, pH 7.2). sGMBS was diluted in modification buffer at 10 mM. Then, sGMBS was added to muIL-13 and after one hour of incubation on a nutator at room temperature, sGMBS in excess was removed using Zeba™ desalting spin column.

c) Conjugation After $CRM_{197}$, muIL-4 and muIL-13 functionalization, protein contents of each preparation were determined by Bradford assay.

Functionalized $CRM_{197}$ was added to functionalized muIL-4 or functionalized muIL-13 at a molar ratio of 1:2 (carrier:muIL-4) and 1:4 (or carrier:muIL-13). Individual immunogenic product preparations were incubated overnight at 4° C., on a nutator. The resulting immunogenic products were then concentrated using Amicon® (3 kDa-cut-off membrane), 0.22 μm-filtered and kept at 4° C.

d) Immunogenic Product Quantifications

Concentrations of muIL-4 immunogenic product and muIL-13 immunogenic product were determined by Coomassie Plus (Bradford) Protein Assay according to the manufacturer instructions.

muCombo Immunogenic Product Preparation

Independently synthesized muIL-4 immunogenic product and muIL-13 immunogenic product were mixed together in a 1-1 weight ratio after the concentration and 0.22 μm sterile-filtration steps and resulting muCombo immunogenic product was stored at 4° C.

Mice Immunization, Allergic Asthma Protocol and Blood Sampling

Figure 7:
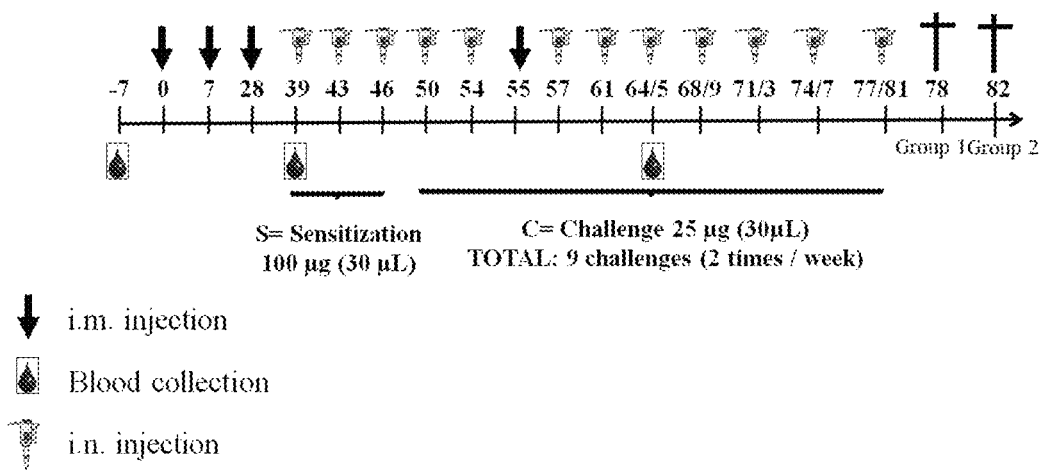
FIG. 7 is a study scheme of immunizations and asthma sensitization in Balb/c mice.

Each Balb/c mouse received four intramuscular (i.m.) injections of immunogenic products alone or muCombo immunogenic product or $CRM_{197}$ alone, as control, all emulsified with squalene-based adjuvant on days 0, 7, 28 and 55 as detailed in Table 6 and FIG. 7. First immunization was performed on mice at 7 weeks of age.

TABLE 6

Dose schedule of administrations

| Article | Number of mice per group | Days | Dose (μg) | Adjuvant |
|---|---|---|---|---|
| muIL-4 immunogenic product | 12 | 0/7/28/55 | 30/30/10/10 | Squalene oil-in-water adjuvant |
| muIL-13 immunogenic product | 12 | 0/7/28/55 | 30/30/10/10 | |
| muCombo immunogenic product | 12 | 0/7/28/55 | 30/30/10/10 | |
| $CRM_{197}$ | 12 | 0/7/28/55 | 15/15/5/5 | |

Thirty-nine days after first immunogenic product immunization, chronic airway inflammation was induced in mice by three intra nasal injections of 100 μg HDM from *Dermatophagoides farinae* (purchased from Greer) on days 39, 43 and 46. Starting on day 50, mice were challenged by intranasal injections with 25 μg HDM twice weekly (total of 9 challenges).

Blood collections were performed seven days before dosing, at days 39, 64 and 24 hours after the last HDM challenge (mice sacrifice). Serum samples were prepared as previously described and were stored at −20° C. until analysis.

In this study were evaluated:
Immunogenicity of the injected products by ELISA and bioassay,
Airway hyperresponsiveness (AHR) measured by whole body plethysmography,
Biological markers: circulating IgE levels in serum by ELISA, airway inflammation in lung and bronchoalveolar lavage (BAL) by FACS analysis and airway histology and inflammatory cell infiltration.

a) Immunogenicity of the Injected Products by ELISA and Bioassay

Antibody titers of anti-muIL-4 and anti-muIL-13 were measured by ELISA (as described above) from mice sera collected in the four treated groups.

Figure 8:
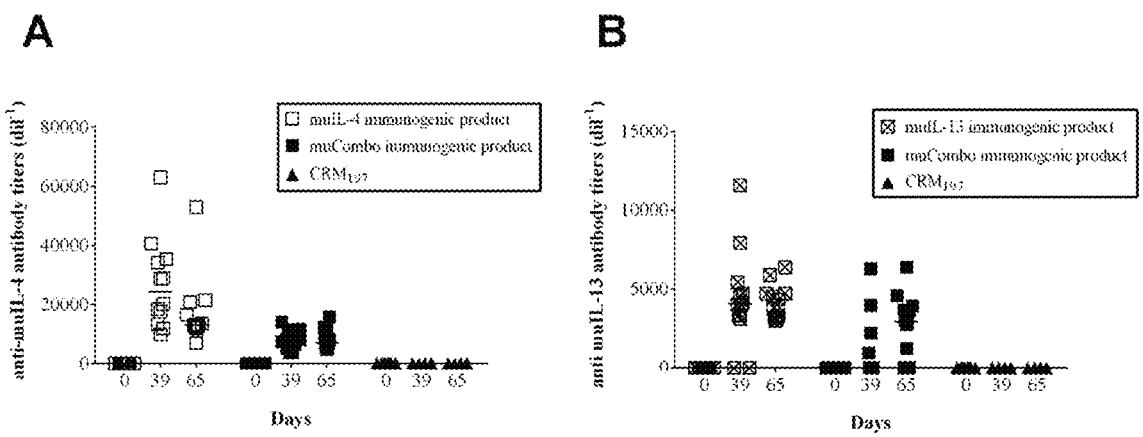
FIG. 8 is a combination of graphs showing anti-muIL-4 (A) and anti-muIL-13 (B) antibodies titers in mice sera. Twelve mice per group. Bars represent median.

No cytokine antibody titers were detected before dosing in all groups and in $CRM_{197}$ receiving group at all time points. Anti-muIL-4 antibody titers were detected in all mice at all time points after muIL-4 immunogenic product and muCombo immunogenic product immunization (FIG. 8-A). Higher levels were observed in mice receiving muIL-4 immunogenic product compared to muCombo immunogenic product. Anti-muIL-13 antibody titers were detected in mice starting at D39 and with 100% responding mice at D65 in muIL-13 immunogenic product group (FIG. 8-B). In muCombo immunogenic product group, anti-muIL-13 antibodies were also detected as soon as D39 and with 9 out of 12 responding mice at D65. Overall, higher antibody titers were observed in sera after immunization with muIL-4 and muIL-13 immunogenic products than with muCombo immunogenic product, as expected since mice in the muCombo group received half the individual immunogenic product dose (FIG. 14).

The neutralization activity of each immunogenic products was assessed in vitro using two different bioassays as described above. Of note, a mouse is considered as a responder in this experiment if $NC_{50}$ is $\geq 200$ $dil^{-1}$ for IL-4 and $\geq 100$ $dil^{-1}$ for IL-13.

High neutralizing capacities against muIL-4 were observed in mice immunized with muIL-4 immunogenic product and muCombo immunogenic product (FIG. 9-A and Table 7), n=11 out of 12 or n=9 out of 12 at least one time point, respectively.

TABLE 7

$NC_{50}$ responders towards IL-4.

| | muIL-4 immunogenic product | | | muCombo immunogenic product | | | $CRM_{197}$ | | |
|---|---|---|---|---|---|---|---|---|---|
| | D0 | D39 | D65 | D0 | D39 | D65 | D0 | D39 | D65 |
| Responders (NC50 > 200 dil-1) | 0/12 | 10/12 | 11/12 | 0/12 | 7/12 | 9/12 | 0/12 | 0/12 | 0/12 |

Interestingly, one year after immunization with muIL-4 or muCombo immunogenic product, anti-IL-4 antibodies were still detected in mice (data not shown).

Figure 9:
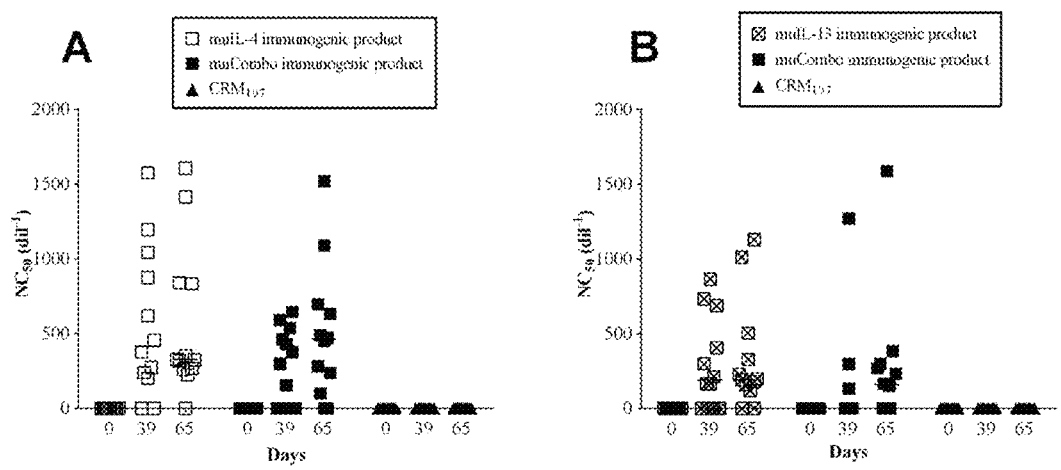
FIG. 9 is a combination of graphs showing muIL-4 (A) and muIL-13 (B) neutralizing capacities in mice sera. Twelve mice per group. Bars represent median.

Neutralizing capacities against muIL-13 in mice immunized with muIL-13 immunogenic product and muCombo immunogenic product were also induced with n=10 out of 12 or n=7 out of 12 at least one time point, respectively (FIG. 9-B and Table 8).

TABLE 8

| | NC₅₀ responders towards IL-13 | | | | | | | | |
|---|---|---|---|---|---|---|---|---|---|
| | muIL-13 immunogenic product | | | muCombo immunogenic product | | | CRM$_{197}$ | | |
| | D0 | D39 | D65 | D0 | D39 | D65 | D0 | D39 | D65 |
| Responders (NC50 > 100 dil-1) | 0/12 | 8/12 | 10/12 | 0/12 | 3/12 | 7/12 | 0/12 | 0/12 | 0/12 |

Interestingly, one year after immunization with muIL-13 or muCombo immunogenic product, anti-IL-13 antibodies were still detected in mice (data not shown).

Of note, co-injection of muIL-4 and/or muIL-13 and CRM$_{197}$ without prior chemical coupling did not elicit anti-IL-4 and anti-IL-13 antibodies, highlighting that conjugation between cytokine and carrier protein is mandatory to break B cell self-tolerance against cytokines.

Different classes (including in particular IgG1, IgG2a, IgG2b, IgG3, IgA, IgE and IgM) of anti-IL-4 and anti-IL-13 antibodies were produced after immunization, mostly IgG1 (data not shown).

b) Airway Hyperresponsiveness (AHR) Measured by Whole Body Plethysmography

Twenty-four hours after the last challenge, AHR was evaluated by whole body plethysmography. Responses to methacholine, a bronchoconstrictor agent, were measured in conscious mice.

Different doses of methacholine were administered by aerosol: 0 mg/mL, 3.5 mg/mL, 7 mg/mL and 14 mg/mL. Enhanced pause (Penh) has been used to evaluate changes in pulmonary function (Hamelmann et al., 1997). This measurement conceptualized the phase shift between the thoracic flow and the nasal flow curves: increased phase shift correlated with increased respiratory system resistance. Penh is calculated by the formula Penh=(Te/RT−1)×PEF/PIF, where Te is expiratory time, RT the relaxation time, PEF the peak expiratory flow, and PIF is peak inspiratory flow. Penh values were recorded during 5 minutes after each methacholine challenge and the maximum value during the period is reported in the graphic.

Figure 10:
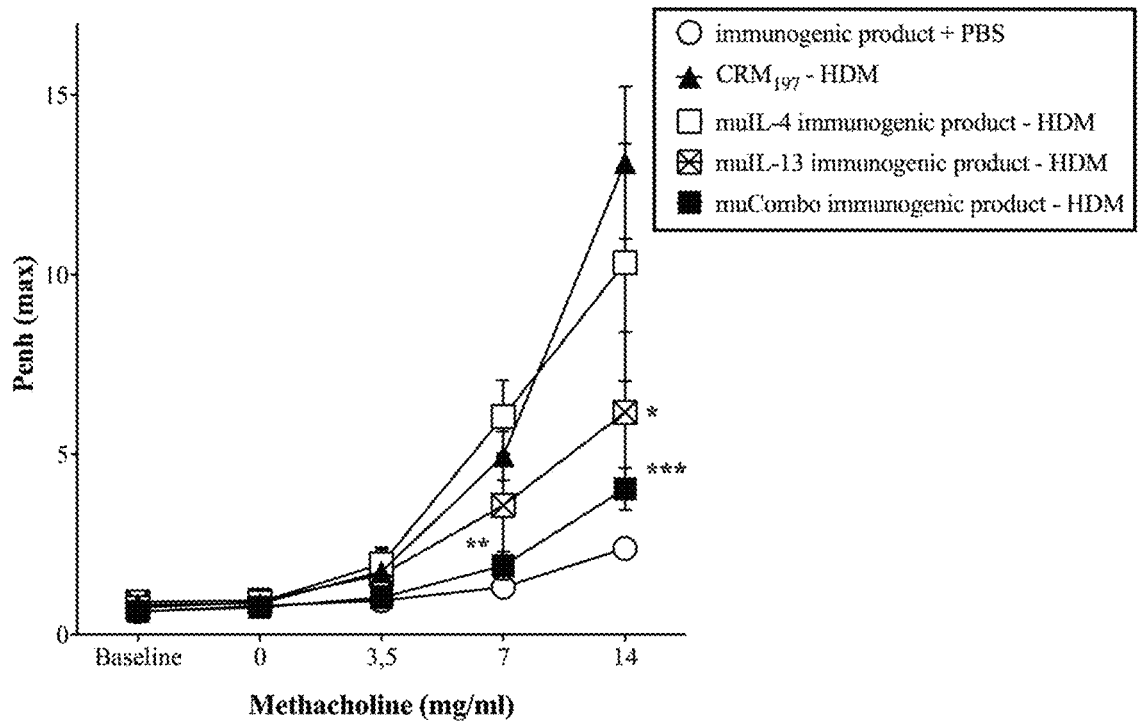
FIG. 10 is a graph showing an airway hyperresponsiveness to inhaled methacholine. Enhanced pause (Penh) values were measured by non-invasive whole body plethysmography. Data were obtained using 7-8 mice per group for HDM sensitized/challenged mice and n=16 for PBS controls. * or  or *: $P<0.5$ or 0.1 or 0.001 vs. $CRM_{197}$-HDM group, using unpaired Mann-Whitney U test.

A high bronchoconstriction in mice sensitized with HDM in CRM$_{197}$ control group was observed (FIG. 10). The bronchoconstriction was partially inhibited with muIL-13 immunogenic product and muIL-4 immunogenic product while it was almost abrogated in mice immunized with muCombo immunogenic product showing the high protective effect of the products of the invention. Indeed, the level of residual bronchoconstriction observed in the muCombo group was similar to the one observed in HDM-unsensitized mice (circle in FIG. 10).

These results were confirmed using invasive airway response measurements. Indeed, HDM-treated control mice exhibited significantly increased changes in lung resistance and elastance upon methacholine challenge, as compared to the PBS-treated control group while these two features were partially reduced in mice treated with muIL-4, muIL-13 or muCombo immunogenic product (data not shown).

Altogether, these results indicate that AHR can be blocked upon dual vaccination against IL-4 and IL-13.

c) Biological Markers

Circulating IgE Levels in Serum by ELISA

Figure 11:
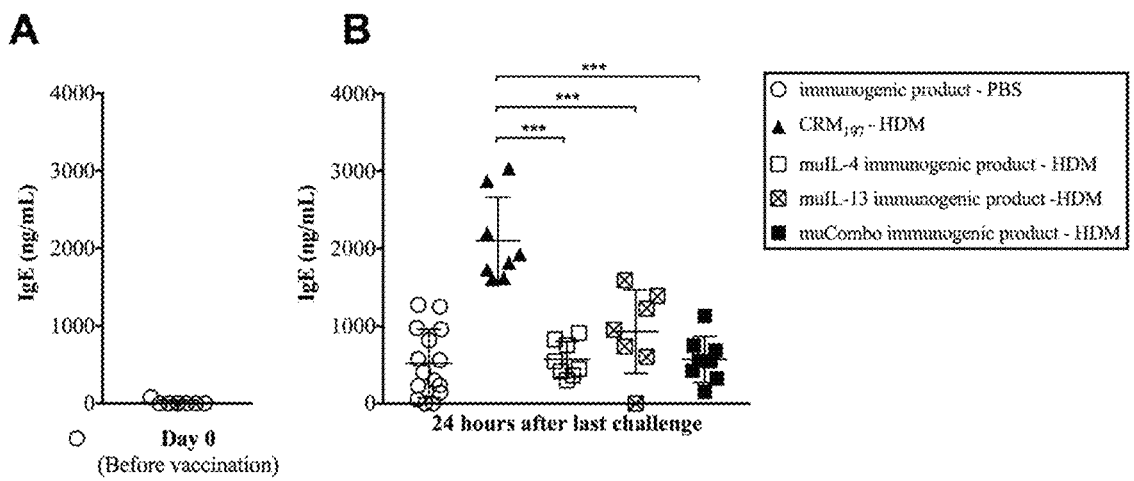
FIG. 11 is a combination of graphs showing the circulating IgE levels in serum collected before vaccination (A) and 24 hours after the last challenge with HDM or PBS (B). Data were obtained using 7-8 mice per group for HDM sensitized/ challenged mice and n=16 for PBS controls. ***: P<0.001 vs. $CRM_{197}$-HDM group, using unpaired Mann-Whitney U test.

Total circulating IgE levels were measured by ELISA following manufacturer's instructions (Mouse IgE ELISA Quantitation Set, Bethyl Labs E90-115) before immunogenic product vaccination and 24 hours after the last HDM challenge (FIG. 11).

No circulating IgE were detected before vaccination. Twenty-four hours after the last challenge with HDM, total circulating IgE were induced due to HDM sensitization (FIG. 11-B). The levels were reduced in all the immunogenic products receiving groups, demonstrating the protection effect of the products of the invention compared to CRM$_{197}$ immunized mice. Of note, similar results were obtained when only HDM-specific IgE were measured by ELISA (data not shown).

HDM-treated mice also present elevated levels of HDM-specific IgG antibodies. However, these levels were not affected by treatment with muIL-4 and/or muIL-13 immunogenic product (data not shown).

Airway Inflammation in Lung and Bronchoalveolar Lavage (BAL)

A detailed time-course analysis of cellular changes in lung and bronchoalveolar lavage (BAL) of mice sensitized with HDM or PBS was carried out.

Inflammatory cells from BAL were analyzed by FACS using the following antibodies (Table 9): CD45-FITC, Ly6G-PE, CD11b-VG, SiglecF-PECy7, B220-APC and CD3-APC according to manufacturer's instructions.

| Antibody | Provider-Catalog number (Clone) |
|---|---|
| Ly6G-PE | BD Pharmingen-561104 (Clone 1A8, Rat IgG$_{2a}$, κ) |
| CD3-APC | BD Pharmingen-561826 (Clone 145-2C11, Armenian Hamster IgG1, κ) |
| CD45-FITC | Miltenyi 130-110-658 (Clone REA737, recombinant human IgG1) |
| SiglecF-PECy7 | Miltenyi 130-112-334 (Clone REA798, recombinant human IgG1) |
| CD11b-VG | Miltenyi 130-110-559 (Clone REA713, recombinant human IgG1) |
| B220-APC | Miltenyi 130-102-259 (Clone RA3-6B2, rat IgG2a κ) |

In lung of control mice, chronic intranasal exposure to HDM resulted in significant increases in the numbers of CD45$^+$ cells infiltration of hematopoietic origin mainly constituted of eosinophils (CD45+, Ly6G−, CD11b+, SiglecF+), as compared to PBS-treated animals (data not shown). Interestingly, immunogenic products vaccination prevented eosinophils infiltration among CD45$^+$ infiltrating cells, especially in the muCombo immunogenic product group that exhibited a statistically significant decrease.

In bronchoalveolar lavage, HDM sensitization resulted in an inflammatory response characterized by CD45$^+$ cells infiltration of hematopoietic origin mainly constituted of eosinophils (CD45+, Ly6G−, CD11b+, SiglecF+) (FIG. 12). Interestingly, immunogenic products vaccination prevented eosinophils infiltration among CD45$^+$ infiltrating cells, especially in the muCombo immunogenic product group that exhibited a statistically significant decrease.

Interestingly, vaccination with immunogenic products of the invention had no effect on the level of eosinophils in the blood (data not shown), indicating that the reduced airway eosinophilia observed in vaccinated mice is a consequence of reduced eosinophil recruitment to the lungs rather than systemic effects on the numbers of eosinophils or eosinophil progenitors.

Airway Histology

The effects of sensitization and vaccination on airway was examined by histological analyses. Briefly, left lung was excised post mortem, fixed with 4% PFA for 24 h at room temperature, and preserved in 70% ethanol. Longitudinal sections were done and stained with:

Hematoxylin and Eosin (H&E) for assessment of leukocyte infiltration,

Toluidine Blue for quantification of mast cell numbers, or

Periodic acid Schiff (PAS) staining for assessment of goblet cells hyperplasia and mucus production.

Globally, these lung histological analyses confirm that vaccination with muIL-4, muIL-13 or muCombo immunogenic product in HDM-treated animals significantly reduced the numbers of leucocytes and intraepithelial mast cells, as compared to non-vaccinated HDM-treated animals (data not shown).

PAS histological analyses also confirm that vaccination with muIL-4, muIL-13 or muCombo immunogenic product in HDM-treated animals significantly reduced the goblet cell hyperplasia/mucus secretion, as compared to non-vaccinated HDM-treated animals (data not shown). These results support that the immunogenic products (in particular muIL-13 and muCombo immunogenic products) may control mucus hypersecretion induced by HDM sensitization.

In conclusion, we have demonstrated that the products of the invention made with $CRM_{197}$ were immunogenic and induced anti-cytokine neutralizing antibodies whether injected alone or in combination (muCombo immunogenic product). The presence of anti-cytokine neutralizing antibodies was associated with a reduction of HDM-induced AHR, measured by Penh value following methacholine inhalation. In addition, these anti-cytokine neutralizing antibodies were able to limit circulating IgE levels as well as mast cells number in lung and eosinophils infiltration in airways.

Consequently, these results demonstrate that the immunogenic products of the invention are capable to break B cell tolerance against IL-4 and IL-13 and suggest that these immunogenic products may represent promising new therapeutic strategies in the treatment of asthma and/or allergy, and in particular in the treatment of allergic asthma.

Interestingly, individual immunogenic products were active but superior beneficial effects on asthma and/or allergy symptoms (and in particular on allergic asthma symptoms) and biological markers were observed when the immunogenic products were combined (muCombo immunogenic product).

Example 6: Preparation of the Human Immunogenic Products of the Invention

The preparation of human IL-4 immunogenic product, IL-13 immunogenic product and Combo immunogenic product was carried out following the same manufacturing process as described above, using the human cytokines IL-4 and IL-13 instead of the murine cytokines.

Preparation of IL-4 and IL-13 Immunogenic Product a) $CRM_{197}$ Functionalization $CRM_{197}$ functionalization was performed as described for the murine product.

b) IL-4 and IL-13 Functionalization

IL-4 or IL-13 dissolved in the buffer (70 mM sodium phosphate buffer, 150 mM NaCl, 5 mM EDTA, pH 7.2) were reacted with sGMBS previously dissolved at a 10 mM concentration in buffer. After one hour of reaction at room temperature with mild agitation, excess sGMBS was removed by Zeba desalting column.

c) Conjugation

After $CRM_{197}$, IL-4 and IL-13 functionalization, protein contents of each preparation were determined by Bradford assay. Functionalized $CRM_{197}$ was added to functionalized IL-4 or functionalized IL-13 at a molar ratio of 1:4 (carrier:IL-4 or carrier:IL-13). Individual immunogenic product preparations were incubated overnight at 4° C. on a nutator. The conjugates were submitted to desalting column to remove potential impurities, such as remaining hydroxylamine, from previous steps. Resulting immunogenic product was concentrated and filtered through a 0.22 µm filter and stored at 4° C.

Preparation of Combo Immunogenic Product

Preparation of Combo immunogenic product can be performed using two different ways: by incubating both modified cytokines concomitantly with the modified carrier protein (simultaneous synthesis) or by mixing two independently synthesized IL-4 and IL-13 immunogenic products (mix preparation).

Combo Immunogenic Product Preparation Via Simultaneous Synthesis a) $CRM_{197}$ Functionalization $CRM_{197}$ functionalization was performed as described for the murine product.

b) IL-4 and IL-13 Functionalization

IL-4 or IL-13 functionalization was performed as described for individual immunogenic product preparation.

c) Conjugation

After $CRM_{197}$, IL-4 and IL-13 functionalization, protein contents of each preparation were determined by Bradford assay. All three modified proteins in phosphate buffer, 150 mM NaCl, 5 mM EDTA, pH 7.2 were mixed at a 2-2-1 molar ratio IL-4-IL-13-$CRM_{197}$. The reaction was carried out at 4° C. overnight. The conjugate was submitted to desalting column to remove potential impurities, such as remaining hydroxylamine, from previous steps. Resulting immunogenic product was concentrated and filtered through a 0.22 µm filter and stored at 4° C.

Combo Immunogenic Product Preparation Via Mix Preparation

Independently synthesized IL-4 and IL-13 immunogenic products were mixed together in a 1-1 weight ratio after the concentration and 0.22 µm sterile-filtration steps. Combo immunogenic product was stored at 4° C. until used.

Example 7: Antigenicity of the Human Product

A sandwich ELISA was performed to evaluate the cytokine coupling to the carrier protein and also evaluating whether epitopes are preserved during the manufacturing process. The protocol used was the same as described hereabove using biotinylated anti-human IL-4 and IL-13 antibodies.

Results are shown in FIG. 13. This test confirmed that the immunogenic product of the invention comprises IL-4 or IL-13 coupled to $CRM_{197}$. Furthermore, these results confirm that the immunogenic product is antigenic (i.e., recognized by anti-IL-4 or anti-IL-13 antibody), as well as in Combo immunogenic product.

Example 8: Immunogenicity of the Human Product

Mice Immunization Protocol

Each Balb/c mouse (10 mice per group) received four intramuscular (i.m.) injections of immunogenic product emulsified with squalene-based adjuvant on days 0, 7, 28 and 49 all performed at a 4 µg dose, as detailed in FIG. 14. First immunization was performed at 7 weeks of age. Blood collections were carried out before dosing, and at days 38, 59, 90 and 120. Serum samples were prepared after coagulation at room temperature and centrifugation to remove the clot.

Determination of Anti-IL4 and Anti-IL-13 Antibodies Titers by ELISA

Anti-cytokines antibody titers were measured by ELISA from mice sera collected in each group.

The determination of each antibody titers in sera after immunization with immunogenic products or combo-immunogenic product were assessed as described above by coating human IL-4 and IL-13 on the 96-well plates.

No cytokine antibody titers were detected before dosing in all groups. Anti-IL-4 antibody titers were detected in all mice at all time points after IL-4 immunogenic product and muCombo immunogenic product immunizations (FIG. 15-A). Similar levels were observed in mice receiving IL-4 immunogenic product and Combo immunogenic product, indicating that we might have reached the plateau of the immune response. Anti-IL-13 antibody titers were detected in all mice at all time points after immunization in IL-13 immunogenic product group (FIG. 15-B). In Combo immunogenic product group, anti-IL-13 antibodies were also detected as soon as D38 and in 8 out of 10 mice at D59. Higher anti-IL-13 antibody titers were observed in sera after immunization with IL-13 immunogenic product than with Combo immunogenic product, since mice in the Combo group received half the individual immunogenic product dose.

Determination of Neutralizing Capacities after Immunizations

Anti-IL-4 and anti-IL-13 neutralizing capacities were assessed using HEK-Blue™ IL-4/IL-13 reporter cell line as described above. Of note, in this experiment, a mouse is considered as a responder if $NC_{50}$ is $\geq 200$ $dil^{-1}$ for IL-4 and $\geq 100$ $dil^{-1}$ for IL-13.

High neutralizing capacities against IL-4 were observed in groups immunized with IL-4 immunogenic product and Combo immunogenic product with 100% of responding mice at all time points after immunization (FIG. 16-A and Table 10).

TABLE 10

| | $NC_{50}$ responders towards IL-4 | | | | | | | | | |
|---|---|---|---|---|---|---|---|---|---|---|
| | IL-4 immunogenic product | | | | | Combo immunogenic product | | | | |
| | D0 | D38 | D59 | D90 | D120 | D0 | D38 | D59 | D90 | D120 |
| Responders (NC50 > 200 dil-1) | 0/10 | 10/10 | 10/10 | 10/10 | 10/10 | 0/10 | 10/10 | 10/10 | 10/10 | 10/10 |

Antibodies with neutralizing capacities against IL-13 were also induced in mice immunized with IL-13 immunogenic product and Combo immunogenic product with 100% of responding mice at D59 (FIG. 16-B and Table 11).

TABLE 11

| | $NC_{50}$ responders towards IL-13 | | | | | | | | | |
|---|---|---|---|---|---|---|---|---|---|---|
| | IL-13 immunogenic product | | | | | Combo immunogenic product | | | | |
| | D0 | D38 | D59 | D90 | D120 | D0 | D38 | D59 | D90 | D120 |
| Responders (NC50 > 200 dil-1) | 0/10 | 9/10 | 10/10 | 9/10 | 9/10 | 0/10 | 9/10 | 10/10 | 10/10 | 10/10 |

Collectively, products of the invention were capable of inducing high anti-cytokines antibody titers with strong neutralizing capacities.

Residual Activity of Human Immunogenic Products

The residual activities of human IL-4 immunogenic product, IL-13 immunogenic product and Combo immunogenic product were monitored using HEK-Blue™ IL-4/IL-13 reporter cell line as described above for the residual activity of IL-4 and IL-13.

TABLE 12

$ED_{50}$ and inactivation factors towards IL-4

| Articles | $ED_{50}$ [ng · mL$^{-1}$] | IL-4 control $ED_{50}$ [ng · mL$^{-1}$] | Inactivation factor |
|---|---|---|---|
| IL-4 immunogenic product | 231 | 0.043 | 5287 |
| Combo immunogenic product | 382 | 0.043 | 8765 |

TABLE 13

$ED_{50}$ and inactivation factors towards IL-13

| Articles | $ED_{50}$ [ng · mL$^{-1}$] | IL-13 control $ED_{50}$ [ng · mL$^{-1}$] | Inactivation factor |
|---|---|---|---|
| IL-13 immunogenic product | 444 | 0.258 | 1848 |
| Combo immunogenic product | 268 | 0.258 | 1116 |

As shown in Table 12 and Table 13, inactivation factors towards IL-4 or IL-13 in the human immunogenic products were all greater than 1000 (and up to 8765), indicating that cytokines residual activities in the immunogenic products were reduced by a minimum of three orders of magnitude compared to native cytokines.

These highly reduced residual activities are an important element supporting the safety profile of the products of the invention.

Example 9: Therapeutic Efficacy of the Immunogenic Product of the Invention in a Mouse Model of Food Allergy Model Food allergy is a major health issue in westernized countries with increasing prevalence over the last decades and a lack of curative treatment. Several major food staples, including milk, peanut, soy and wheat can induce food allergic reactions. Food allergies reflect a failure of oral tolerance of innocuous food allergens, resulting in the development of a dysregulated Th2-immune response, the secretion of Th2 cytokines (mostly IL-4 and IL-13), the secretion of allergen specific-IgE and the recruitment of effector cells to the gastrointestinal (GI) tract.

The therapeutic efficacy of the immunogenic product of the invention in food allergy was investigated using IL-4raF709 mutant mice. IL-4raF709 mice carry a gain-of-function mutation in the IL-4 receptor (IL-4R) alpha chain that disrupts the binding of the Src homology domain 2 containing protein tyrosine phosphatase 1 (SHP-1) to the receptor subunit and leads to augmented signal transducer and activator of transcription 6 (STAT6) activation by IL-4 and IL-13. These mice exhibit enhanced Th2 cell responses and IgE production. Thus, this mutation is prototypic of a number of human IL-4Ralpha polymorphisms that promote receptor signaling and are associated with atopy.

Preparation of muIL-4/IL-13 and muCombo Immunogenic Products muIL-4, muIL-13 and muCombo immunogenic products are synthetized as described herein above.

Mice Immunization, Food Allergy Model, Anaphylaxis Response, Histological Analyses and Blood Sampling Each IL-4raF709 mutant mice were immunized with muIL-4, muIL-13 or muCombo immunogenic products or $CRM_{197}$, as a control, all emulsified with squalene-based adjuvant on days 0, 7, 28 and then boosted.

In parallel, mice were sensitized by oral gavage with either PBS or with 23 mg of Peanut (PE) butter, corresponding to 5 mg of peanut protein, suspended in 250 µl of 0.1 M sodium bicarbonate (pH 8.0). Mice were challenged with an enteral bolus of 450 mg peanut butter (100 mg protein), diluted in water (Burton et al., 2014).

Just after the challenge, core body temperature was followed during one hour as well as the onset of diarrhea.

A clinical score was also determined: 0, no clinical symptom; 1, repetitive mouth/ear scratching and ear canal digging with hind legs; 2, decreased activity, self-isolation, puffiness around eyes and/or mouth; 3, periods of motionless for more than one minute, lying prone on stomach; 4, no response to whisker stimuli, reduced or no response to prodding; 5, tremor convulsion or death.

Sections of intestinal tissues were collected for histological analyses (e.g., mast cell quantification).

Blood was also collected to study the level of inflammation (e.g., mast cell degranulation product), antibody levels (e.g., anti-cytokines titers, neutralizing capacities, allergen-specific-IgG and -IgE and total IgE).

Example 10: Therapeutic Efficacy of the Immunogenic Product of the Invention in a Mouse Model of Atopic Dermatitis Atopic dermatitis (AD) is a chronic or chronically relapsing, pruritic inflammatory skin disease. The incidence of AD has dramatically increased for the past three decades in industrialized countries. Immunological abnormalities of AD are generally characterized by sensitization with various allergens (e.g., foods, aeroallergens, microbes, and autoallergens), high serum IgE levels, and skin lesions with apoptotic keratinocytes and infiltration with immune cells that secrete Th2 cytokines such as IL-4, IL-5 and IL-13.

The therapeutic efficacy of the immunogenic products of the invention in AD was investigated by using an animal model in which repeated epicutaneous application of a house dust mite (HDM) extract and staphylococcal enterotoxin B induces eczematous skin lesions.

Preparation of muIL-4/IL-13 and muCombo Immunogenic Products muIL-4, muIL-13 and muCombo immunogenic products are synthetized as described herein above.

Mice Immunization, Atopic Dermatitis Induction, Clinical Severity Measurement, Histological Analyses and Blood Sampling Mice were immunized with muIL-4, muIL-13 or muCombo immunogenic products or $CRM_{197}$, as a control, all emulsified with squalene-based adjuvant.

In parallel, atopic dermatitis was induced as previously described in Ando et al. (J Invest Dermatol. 2013 December; 133(12):2695-2705). Briefly, solutions of 500 ng of Staphylococcal enterotoxin (SEB) and 10 µg of *Dermatophagoides farinae* extract (Der f is a house dust mite, HDM) were applied on a gauze pad placed on the shaved area. This portion of the back skin was occluded with a Tegaderm™ Transparent Dressing using bandages. Three days later, the dressings were replaced with a new one. After an additional 4 days had passed, the dressings were removed and the mice were kept without treatment for the next week. The one-week Der f/SEB treatment was repeated two more times, thus mice were the subjected to three cycles of such treatment.

Clinical severity was scored by an investigator who did not know the identities of mice 2 days after removing the dressings in the last cycle. Clinical scores were based on the severity (0, no symptoms; 1, mild; 2, intermediate; 3, severe) of four possible symptoms (redness, bleeding, eruption, and scaling). Maximum possible score is 12.

Mice were euthanized immediately after scoring, back skin specimens corresponding to the treated areas were obtained for histological analyses of epidermal thickness and eosinophilia. Blood was also collected to study the level of inflammation and antibody levels (e.g., anti-cytokines titers, neutralizing capacities, allergen-specific-IgG and -IgE and total IgE).

Example 11: Therapeutic Efficacy of the Immunogenic Product of the Invention in a Mouse Model of Chronic Obstructive Pulmonary Disease (COPD)

COPD is characterized by the progressive airflow limitation commonly associated with exaggerated inflammatory responses to inhaled irritants, which leads to the chronic obstructive bronchitis and the destruction of lung parenchyma, termed emphysema.

Several animal models of COPD have been established to elucidate possible mechanisms underlying the initiation and progression of COPD. Here, a protease-induced model was used to assess the therapeutic efficacy of the immunogenic product of the invention in COPD.

Preparation of muIL-4/IL-13 and muCombo Immunogenic Products muIL-4, muIL-13 and muCombo immunogenic products are synthetized as described herein above.

Mice Immunization, Atopic Dermatitis Induction, Leukocyte Quantification and Histological Analyses Mice were immunized with muIL-4, muIL-13 or muCombo immunogenic products or $CRM_{197}$, as a control, all emulsified with squalene-based adjuvant.

In parallel, intranasal instillation of elastolytic enzymes, such as porcine pancreatic elastase was used to trigger COPD-like symptoms such as, for example, emphysema formation. Briefly, BALB/c mice were intranasally treated with 0.6 U porcine pancreatic elastase in 30 μL of PBS (Shibata et al. *Proc Natl Acad Sci USA*. 2018 Dec. 18; 115(51):13057-13062).

In a first experiment, mice were euthanized on day 5 for assessment of leukocytes: Number of leukocytes (e.g., monocytes, macrophages, neutrophils, T cells, B cells and eosinophils) was quantified by flow cytometry in bronchoalveolar lavage (BAL) fluids and single cell suspensions of lung cells. An additional assessment of leukocyte infiltration in the lungs was performed by histological examinations of lung tissues previously stained with hematoxylin and eosin (H&E). Blood was also collected to study the level of inflammation and antibody levels (e.g., anti-cytokines titers, neutralizing capacities).

In a second experiment, mice were sacrificed on day 21 after elastase treatment for assessment of lung emphysema by histology in H&E-stained lung tissue sections, using mean linear intercept (MLI) as an indicator of lung airspace enlargement. Blood was also collected to study the level of inflammation and antibody levels (e.g., anti-cytokines titers, neutralizing capacities, allergen-specific-IgG and -IgE and total IgE).

Example 12: Therapeutic Efficacy of the Immunogenic Product of the Invention in a Mouse Model of Pulmonary Fibrosis Pulmonary fibrosis represents a broad spectrum of diseases that are characterized by different degrees of lung inflammation, excessive proliferation of lung fibroblasts, and increased lung collagen content.

The therapeutic efficacy of the immunogenic product of the invention in pulmonary fibrosis was investigated using an animal model in which bleomycin (BLM) administration in lungs leads to secretion of proinflammatory cytokines and chemokines, recruitment of leukocytes, increased collagen production, remodeling, and fibrosis lung inflammation.

Preparation of muIL-4/IL-13 and muCombo Immunogenic Products muIL-4, muIL-13 and muCombo immunogenic products are synthetized as described herein above.

Mice immunization, pulmonary fibrosis induction, leukocyte quantification and histological analyses Mice were immunized with muIL-4, muIL-13 or muCombo immunogenic products or $CRM_{197}$, as a control, all emulsified with squalene-based adjuvant.

In parallel, pulmonary fibrosis was induced in C57BL/6 mice as described previously by Reber et al. (J Immunol 2014 Feb. 15; 192(4):1847-54). Briefly, pulmonary fibrosis was induced by intranasal (i.n.) administration of BLM hydrochloride (0.1 mg in 25 μl PBS; 12.5 μl/nostril).

Body weight was monitored 5 times per week until the end of the experiment and mice were euthanized 7 days or 14 days after BLM treatment for assessment of lung fibrosis.

Number of leukocytes (e.g., monocytes, macrophages, neutrophils, T cells, B cells and eosinophils) was quantified by flow cytometry in bronchoalveolar lavage (BAL) fluids and single cell suspensions of lung cells.

Histological examinations of lung tissues stained with hematoxylin and eosin (for assessment of leukocyte infiltration), masson trichrome (for assessment of fibrosis), or toluidine blue (for assessment of mast cell numbers) were performed.

Blood was also collected to study the level of inflammation and antibody levels (e.g., anti-cytokines titers, neutralizing capacities).

The invention claimed is:

1. An immunogenic product comprising at least one cytokine conjugated with a carrier protein, wherein the at least one cytokine is IL-13 or a fragment thereof comprising at least 50 amino acids from IL-13, and wherein the carrier protein is $CRM_{197}$, and wherein the immunogenic product is obtained by a method comprising steps of:
   a) contacting the at least one cytokine with N-[γ-maleimidobutyryloxy]-succinimide ester (sGMBS);
   b) contacting the carrier protein with N-succinimidyl-S-acetylthioacetate (SATA), to generate a carrier-SATA complex; and
   c) contacting the sGMBS-cytokine complex obtained at step (a) with the carrier-SATA complex obtained at step (b).

2. The immunogenic product according to claim 1, wherein the $CRM_{197}$ is further coupled with IL-4.

3. A composition comprising at least one immunogenic product comprising at least one cytokine conjugated with a carrier protein, wherein the at least one cytokine is IL-13 or a fragment thereof comprising at least 50 amino acids from IL-13, and wherein the carrier protein is $CRM_{197}$, and wherein the immunogenic product is obtained by a method comprising steps of:
   a) contacting the at least one cytokine with N-[γ-maleimidobutyryloxy]-succinimide ester (sGMBS);
   b) contacting the carrier protein with N-succinimidyl-S-acetylthioacetate (SATA), to generate a carrier-SATA complex; and
   c) contacting the sGMBS-cytokine complex obtained at step (a) with the carrier-SATA complex obtained at step (b).

4. The composition according to claim 3, comprising a mixture of at least two immunogenic products comprising at least one cytokine conjugated with a carrier protein, wherein the at least one cytokine is IL-13 or a fragment thereof comprising at least 50 amino acids from IL-13, and wherein the carrier protein is $CRM_{197}$.

5. The composition according to claim 3, comprising a mixture of an immunogenic product comprising IL-4 and $CRM_{197}$ with an immunogenic product comprising IL-13 and $CRM_{197}$.

6. The composition according to claim 4, comprising a mixture of an immunogenic product comprising IL-4 and $CRM_{197}$ with an immunogenic product comprising IL-13 and $CRM_{197}$ at a weight ratio ranging from about 10:1 to about 1:10.

7. The composition according to claim 3, further comprising at least one pharmaceutically acceptable excipient and/or at least one adjuvant.

8. The composition according to claim 3, being an emulsion.

* * * * *

SEQUENCE LISTING

<160> NUMBER OF SEQ ID NOS: 8

<210> SEQ ID NO 1
<211> LENGTH: 535

```
<212> TYPE: PRT
<213> ORGANISM: Artificial Sequence
<220> FEATURE:
<223> OTHER INFORMATION: CRM197

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380
```

```
Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
            450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
            485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
            530                 535

<210> SEQ ID NO 2
<211> LENGTH: 129
<212> TYPE: PRT
<213> ORGANISM: Homo sapiens
<220> FEATURE:
<223> OTHER INFORMATION: Human IL-4

<400> SEQUENCE: 2

His Lys Cys Asp Ile Thr Leu Gln Glu Ile Ile Lys Thr Leu Asn Ser
1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
            115                 120                 125

Ser

<210> SEQ ID NO 3
<211> LENGTH: 22
<212> TYPE: PRT
<213> ORGANISM: Homo sapiens
<220> FEATURE:
<223> OTHER INFORMATION: Fragment of Human IL-4

<400> SEQUENCE: 3

Ala Gln Gln Phe His Arg His Lys Gln Leu Ile Arg Phe Leu Lys Arg
1               5                   10                  15
```

Leu Asp Arg Asn Leu Trp
            20

<210> SEQ ID NO 4
<211> LENGTH: 120
<212> TYPE: PRT
<213> ORGANISM: Mus musculus
<220> FEATURE:
<223> OTHER INFORMATION: Murine IL-4

<400> SEQUENCE: 4

His Ile His Gly Cys Asp Lys Asn His Leu Arg Glu Ile Ile Gly Ile
1               5                   10                  15

Leu Asn Glu Val Thr Gly Glu Gly Thr Pro Cys Thr Glu Met Asp Val
            20                  25                  30

Pro Asn Val Leu Thr Ala Thr Lys Asn Thr Thr Glu Ser Glu Leu Val
        35                  40                  45

Cys Arg Ala Ser Lys Val Leu Arg Ile Phe Tyr Leu Lys His Gly Lys
    50                  55                  60

Thr Pro Cys Leu Lys Lys Asn Ser Ser Val Leu Met Glu Leu Gln Arg
65                  70                  75                  80

Leu Phe Arg Ala Phe Arg Cys Leu Asp Ser Ser Ile Ser Cys Thr Met
                85                  90                  95

Asn Glu Ser Lys Ser Thr Ser Leu Lys Asp Phe Leu Glu Ser Leu Lys
            100                 105                 110

Ser Ile Met Gln Met Asp Tyr Ser
        115                 120

<210> SEQ ID NO 5
<211> LENGTH: 108
<212> TYPE: PRT
<213> ORGANISM: Canis
<220> FEATURE:
<223> OTHER INFORMATION: Canine IL-4

<400> SEQUENCE: 5

His Asn Phe Asn Ile Thr Ile Lys Glu Ile Ile Lys Met Leu Asn Ile
1               5                   10                  15

Leu Thr Ala Arg Asn Asp Ser Cys Met Glu Leu Thr Val Lys Asp Val
            20                  25                  30

Phe Thr Ala Pro Lys Asn Thr Ser Asp Lys Glu Ile Phe Cys Arg Ala
        35                  40                  45

Ala Thr Val Leu Arg Gln Ile Tyr Thr His Asn Cys Ser Asn Arg Tyr
    50                  55                  60

Leu Arg Gly Leu Tyr Arg Asn Leu Ser Ser Met Ala Asn Lys Thr Cys
65                  70                  75                  80

Ser Met Asn Glu Ile Lys Lys Ser Thr Leu Lys Asp Phe Leu Glu Arg
                85                  90                  95

Leu Lys Val Ile Met Gln Lys Lys Tyr Tyr Arg His
            100                 105

<210> SEQ ID NO 6
<211> LENGTH: 122
<212> TYPE: PRT
<213> ORGANISM: Homo sapiens
<220> FEATURE:
<223> OTHER INFORMATION: Human IL-13

<400> SEQUENCE: 6

Leu Thr Cys Leu Gly Gly Phe Ala Ser Pro Gly Pro Val Pro Pro Ser

-continued

```
              1               5                  10                  15
            Thr Ala Leu Arg Glu Leu Ile Glu Glu Leu Val Asn Ile Thr Gln Asn
                            20                  25                  30

Gln Lys Ala Pro Leu Cys Asn Gly Ser Met Val Trp Ser Ile Asn Leu
                            35                  40                  45

Thr Ala Gly Met Tyr Cys Ala Ala Leu Glu Ser Leu Ile Asn Val Ser
                            50                  55                  60

Gly Cys Ser Ala Ile Glu Lys Thr Gln Arg Met Leu Ser Gly Phe Cys
            65                              70                  75                  80

Pro His Lys Val Ser Ala Gly Gln Phe Ser Ser Leu His Val Arg Asp
                                    85                  90                  95

Thr Lys Ile Glu Val Ala Gln Phe Val Lys Asp Leu Leu Leu His Leu
                                    100                 105                 110

Lys Lys Leu Phe Arg Glu Gly Arg Phe Asn
                            115                 120

<210> SEQ ID NO 7
<211> LENGTH: 110
<212> TYPE: PRT
<213> ORGANISM: Mus musculus
<220> FEATURE:
<223> OTHER INFORMATION: Murine IL-13

<400> SEQUENCE: 7

Pro Val Pro Arg Ser Val Ser Leu Pro Leu Thr Leu Lys Glu Leu Ile
            1               5                   10                  15

Glu Glu Leu Ser Asn Ile Thr Gln Asp Gln Thr Pro Leu Cys Asn Gly
                            20                  25                  30

Ser Met Val Trp Ser Val Asp Leu Ala Ala Gly Gly Phe Cys Val Ala
                            35                  40                  45

Leu Asp Ser Leu Thr Asn Ile Ser Asn Cys Asn Ala Ile Tyr Arg Thr
                            50                  55                  60

Gln Arg Ile Leu His Gly Leu Cys Asn Arg Lys Ala Pro Thr Thr Val
            65                              70                  75                  80

Ser Ser Leu Pro Asp Thr Lys Ile Glu Val Ala His Phe Ile Thr Lys
                                    85                  90                  95

Leu Leu Ser Tyr Thr Lys Gln Leu Phe Arg His Gly Pro Phe
                            100                 105                 110

<210> SEQ ID NO 8
<211> LENGTH: 113
<212> TYPE: PRT
<213> ORGANISM: Canis
<220> FEATURE:
<223> OTHER INFORMATION: Canine IL-13

<400> SEQUENCE: 8

Ser Pro Ser Pro Val Thr Pro Ser Pro Thr Leu Lys Glu Leu Ile Glu
            1               5                   10                  15

Glu Leu Val Asn Ile Thr Gln Asn Gln Ala Ser Leu Cys Asn Gly Ser
                            20                  25                  30

Met Val Trp Ser Val Asn Leu Thr Ala Gly Met Tyr Cys Ala Ala Leu
                            35                  40                  45

Glu Ser Leu Ile Asn Val Ser Asp Cys Ser Ala Ile Gln Arg Thr Gln
                            50                  55                  60

Arg Met Leu Lys Ala Leu Cys Ser Gln Lys Pro Ala Ala Gly Gln Ile
            65                              70                  75                  80
```

-continued

```
Ser Ser Glu Arg Ser Arg Asp Thr Lys Ile Glu Val Ile Gln Leu Val
                85                  90                  95

Lys Asn Leu Leu Thr Tyr Val Arg Gly Val Tyr Arg His Gly Asn Phe
            100                 105                 110

Arg
```